United States Patent
Bazan et al.

(10) Patent No.: US 11,713,318 B2
(45) Date of Patent: Aug. 1, 2023

(54) SHORT CONJUGATED OLIGOELECTROLYTES AND USES THEREOF

(71) Applicant: The Regents Of The University Of California, Oakland, CA (US)

(72) Inventors: Guillermo Bazan, Santa Barbara, CA (US); Zichao Zhang, Goleta, CA (US); Alex Moreland, Santa Barbara, CA (US); Michael J. Mahan, Santa Barbara, CA (US); Douglas M. Heithoff, Santa Barbara, CA (US); Jakkarin Limwongyut, Goleta, CA (US); Chenyao Nie, Goleta, CA (US)

(73) Assignee: The Regents Of The University Of California, Oakland, CA (US)

( * ) Notice: Subject to any disclaimer, the term of this patent is extended or adjusted under 35 U.S.C. 154(b) by 87 days.

(21) Appl. No.: 17/040,320

(22) PCT Filed: Mar. 21, 2019

(86) PCT No.: PCT/US2019/023411
§ 371 (c)(1),
(2) Date: Sep. 22, 2020

(87) PCT Pub. No.: WO2019/183381
PCT Pub. Date: Sep. 26, 2019

(65) Prior Publication Data
US 2021/0017179 A1  Jan. 21, 2021

Related U.S. Application Data

(60) Provisional application No. 62/647,181, filed on Mar. 23, 2018.

(51) Int. Cl.
| | |
|---|---|
| C07D 471/08 | (2006.01) |
| A61P 31/04 | (2006.01) |
| C07C 217/62 | (2006.01) |
| C07C 279/08 | (2006.01) |
| C07C 309/24 | (2006.01) |
| C07D 401/14 | (2006.01) |

(52) U.S. Cl.
CPC ............ C07D 471/08 (2013.01); A61P 31/04 (2018.01); C07C 217/62 (2013.01); C07C 279/08 (2013.01); C07C 309/24 (2013.01); C07D 401/14 (2013.01)

(58) Field of Classification Search
CPC .................................................. C07D 471/08
See application file for complete search history.

(56) References Cited

U.S. PATENT DOCUMENTS

| 4,482,680 A | 11/1984 | Sheldon et al. |
| 2004/0192968 A1 | 9/2004 | Bazan et al. |
| 2005/0214952 A1 | 9/2005 | Stupp et al. |
| 2014/0242148 A1 | 8/2014 | Whitten et al. |
| 2017/0164614 A1 | 6/2017 | Whitten et al. |

FOREIGN PATENT DOCUMENTS

| CN | 104224775 A | 12/2014 |
| GB | 726260 A | 3/1955 |
| WO | WO 2005/056499 | 6/2005 |

OTHER PUBLICATIONS

Yan, Chem. Sci. (2016) &:5714-5722.*
West (Solid-State Chemistry and Its Applications, 1984, John Wiley & Sons.*
J. G. Cannon, Chapter Nineteen in Burger's Medicinal Chemistry and Drug Discovery, Fifth Edition, vol. I: Principles and Practice, Wiley-Interscience 1995.*
Venkatesh, J. Pharm. Sci. 89, 145-154 (2000) (p. 146.*
Liu et al., "Conjugated oligoelectrolyte represses hydrogen oxidation by *Geobacter sulfurreducens* in microbial electrolysis cells" Bioelectrochemistry (2015) 106:379-382.
Pubchem CID 102513185, created Dec. 28, 2015.
Yan et al., "Influence of molecular structure on the antimicrobial function of phenylenevinylene conjugated oligoelectrolytes" Chem. Sci. (2016) &:5714-5722.
International Search Report and Written Opinion dated Aug. 2, 2019 for PCT Application No. PCT/US2019/023411, filed Mar. 21, 2019.
Gwozdizinska et al., "Phenylenevinylene conjugated oligoelectrolytes as fluorescent dyes for mammalian cell imaging" Chemical Communications (2014) 50(94):14859-14861.
Nag et al., "pH-responsive water soluble smart vesicles containing a bis(styryl)benzene derivative for two-photonmicroscopy imaging" Journal of Materials Chemistry (2012) 22(5):1977-1984.
Written Opinion and Search Report dated Apr. 6, 2022 for SG Application No. 11202009242R, filed Sep. 21, 2020.
International Preliminary Report on Patentability dated Sep. 29, 2020 for PCT Application No. PCT/US2019/023411, filed Mar. 21, 2019.
Extended European Search Report dated Feb. 23, 2022 for EP Application No. 19772107.9, filed Mar. 21, 2019.
Office Action dated Oct. 28, 2022 for Chinese Application No. 201980031110.5, filed Mar. 21, 2019.

* cited by examiner

*Primary Examiner* — Nizal S Chandrakumar
(74) *Attorney, Agent, or Firm* — Knobbe Martens Olson & Bear LLP

(57) ABSTRACT

Compositions and methods of making and using thereof are provided with a specific antimicrobial activity and efficacy toward Gram-positive and Gram-negative bacteria and low levels of toxicity toward mammalian cells. The compositions include water-soluble molecules characterized by a hydrophobic interior fragment and side groups containing cationic groups. A class of these molecules is provided with variations in the length of the internal conjugated segment and in other molecular features, which impact the efficacy and toxicity. The substituents on the cationic functional group, the structural variations on the solubilizing group, and the length of the conjugated segment are important features affecting the antimicrobial property and the non-toxicity to mammalian cells of the composition.

7 Claims, 13 Drawing Sheets

|  | MIC (µg/mL, *E. coli* K12) | Percent Cell Viability (Hep G2 at 128 µg/mL) |
|---|---|---|
| Formula O | 16 | 71 |
| Formula Q | 4 | 91 |
| Formula AA | 2 | 75 |

FIG. 17C

SHORT CONJUGATED OLIGOELECTROLYTES AND USES THEREOF

CROSS REFERENCE TO RELATED APPLICATIONS

This application is a U.S. National Phase Application of PCT International Application No. PCT/US2019/023411, filed on Mar. 21, 2019, designating the United States of America and published in the English language, which claims priority to U.S. Provisional Application No. 62/647,181, filed Mar. 23, 2018. The disclosures of the above-referenced applications are hereby expressly incorporated by reference in their entireties.

STATEMENT OF GOVERNMENT INTEREST

This invention was made with Government support under Grant No. W911NF-09-D-0001 awarded by Department of the Army. The Government has certain rights in this invention.

BACKGROUND

Field

This application relates to antimicrobial or bactericidal conjugated oligoelectrolyte compounds (COEs), and more specifically to molecules with a high efficacy toward both Gram-negative and Gram-positive bacteria and a low toxicity toward mammalian cells.

Description

Human health has benefited from the development of antimicrobial prophylaxis and therapeutics. For example, the first antibiotic, penicillin, was introduced in 1940. However, Abraham and coworkers found cultures of staphylococci developed resistance after continuous subculture in the presence of penicillin. Methicillin was introduced in 1959 to overcome increasing bacterial resistance to not only penicillin, but also streptomycin, tetracycline and erythromycin. Unfortunately, 18 strains of *S. aureus* were reported to exhibit resistance to methicillin within two years. In attempts to solve this problem, new antibiotics continued to be developed, including vancomycin, which constitutes a last resort for treating methicillin-resistant *S. aureus* infections. However, a vancomycin-resistant strain of *S. aureus* was also reported in 2002.

The ability of microbes to develop antimicrobial resistance underlies the emergence of drug resistant strains whose infections are increasingly difficult to treat, resulting in increased hospitalization times with significant negative economic implications. New molecular systems to treat multidrug resistant strains that do not elicit microbial resistance are thus a research priority attracting significant scientific and healthcare interest SUMMARY The following embodiments and aspects thereof are described and illustrated in conjunction with compositions and methods which are meant to be exemplary and illustrative, not limiting in scope.

Some embodiments described herein relate to a compound of Formula 1, Formula 2, Formula 3, Formula 4, Formula 5, Formula 6 and/or Formula 7, or a pharmaceutically acceptable isomer, racemate, hydrate, solvate, isotope, or salt of any of the foregoing. Other embodiments described herein relate to a compound of Formula (I), Formula (II), Formula (III), Formula (IV) and/or Formula (V), or a pharmaceutically acceptable isomer, racemate, hydrate, solvate, isotope, or salt of any of the foregoing, as provided in the section entitled "Further Formulae."

Some embodiments, described herein relate to a pharmaceutical composition that can include an effective amount of a compound described herein, such as a compound of Formula 1, Formula 2, Formula 3, Formula 4, Formula 5, Formula 6, Formula 7, Formula (I), Formula (II), Formula (III), Formula (IV) and/or Formula (V), or a pharmaceutically acceptable isomer, racemate, hydrate, solvate, isotope, or salt of any of the foregoing; and a pharmaceutically acceptable carrier, diluent, or excipient, wherein Formula (I), Formula (II), Formula (III), Formula (IV) and Formula (V), or a pharmaceutically acceptable isomer, racemate, hydrate, solvate, isotope, or salt of any of the foregoing, are as provided in the section entitled "Further Formulae."

Some embodiments described herein relate to a method of treating, reducing the severity of, and/or slowing the progression of a bacterial infection in a subject in need thereof, that can include administering an effective amount of a compound of Formula 1, Formula 2, Formula 3, Formula 4, Formula 5, Formula 6 and/or Formula 7, or a pharmaceutically acceptable isomer, racemate, hydrate, solvate, isotope, or salt of any of the foregoing, or a pharmaceutically acceptable composition comprising the same. Other embodiments described herein relate to a method of treating, reducing the severity of, and/or slowing the progression of a bacterial infection in a subject in need thereof, that can include administering an effective amount of a compound of Formula (I), Formula (II), Formula (III), Formula (IV) and/or Formula (V), or a pharmaceutically acceptable isomer, racemate, hydrate, solvate, isotope, or salt of any of the foregoing, or a pharmaceutically acceptable composition comprising the same, Formula (I), Formula (II), Formula (III), Formula (IV) and Formula (V), or a pharmaceutically acceptable isomer, racemate, hydrate, solvate, isotope, or salt of any of the foregoing, wherein Formula (I), Formula (II), Formula (III), Formula (IV) and Formula (V), or a pharmaceutically acceptable isomer, racemate, hydrate, solvate, isotope, or salt of any of the foregoing, are as provided in the section entitled "Further Formulae." In some embodiments, the bacterial infection is a drug resistant bacterial infection.

Provided herein are COEs, compositions based on conjugated oligoelectrolytes (COEs) and methods of making and using thereof along with specific antimicrobial activity and efficacy toward Gram-positive and Gram-negative bacteria and low levels of toxicity toward mammalian cells. The compounds include water-soluble molecules characterized by a hydrophobic interior fragment and side groups containing charged groups, such as cationic groups.

Other features and advantages of the application will become apparent from the following detailed description, taken in conjunction with the accompanying drawings, which illustrate, by way of example, various features of embodiments of the application.

BRIEF DESCRIPTION OF THE DRAWINGS

Exemplary embodiments are illustrated in referenced figures. It is intended that the embodiments and figures disclosed herein are to be considered illustrative rather than restrictive.

FIGS. 17A-C depict the cytotoxicity and antimicrobial profiles of selected Formulae grouped to highlight specific structure-property trends.

DETAILED DESCRIPTION

Figure 1:
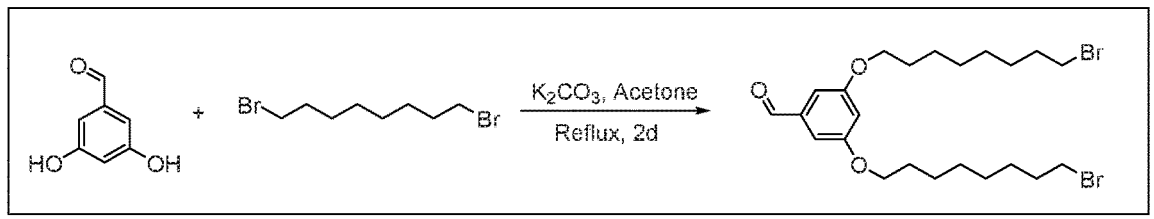
FIG. 1 depicts a schematic of the synthesis of 3,5-bis((8-bromooctyl)oxy)benzaldehyde.

All references cited herein, including all of the U.S. patents, U.S. patent application publications, U.S. patent applications, foreign patents, foreign patent applications and non-patent publications referred to in this specification and/or listed in the Application Data Sheet, are incorporated by reference in their entirety, unless indicated otherwise. It is not an admission that any of the aforementioned documents are prior art or relevant to the present application, or that any publication specifically or implicitly referenced is prior art.

Unless defined otherwise, technical and scientific terms used herein have the same meaning as commonly understood by one of ordinary skill in the art. Singleton et al., *Dictionary of Microbiology and Molecular Biology* 3$^{rd}$ ed., Revised, J. Wiley & Sons (New York, N.Y. 2006); March, *Advanced Organic Chemistry Reactions, Mechanisms and Structure* 7$^{th}$ ed., J. Wiley & Sons (New York, N.Y. 2013); and Sambrook and Russel, Molecular Cloning. *A Laboratory Manual* 4$^{th}$ ed., Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* 2$^{nd}$ ed. (Cold Spring Harbor Press, Cold Spring Harbor N.Y., 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85: 5879-5883 (1988); Ward et al., Nature 334: 544-54 (1989); Tomlinson I. and Holliger P. (2000) Methods Enzymol, 326, 461-479; Holliger P. (2005) Nat. Biotechnol. September; 23(9):1126-36).

One skilled in the art will recognize many methods and materials similar or equivalent to those described herein, which could be used in the practice of the present application. Indeed, the present application is in no way limited to the methods and materials described. For purposes of the present application, the following terms are defined below.

Unless otherwise indicated, the term "alkyl" means a straight chain and/or branched hydrocarbon having from 1 to 20 (e.g., 1 to 10 or 1 to 4) carbon atoms, i.e., $C_1$-$C_{20}$ (including any integer number of carbon atoms between 1 and 20). Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl.

Unless otherwise indicated, the term "alkenyl" means a straight chain and/or branched hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkynyl" means a straight chain and/or branched having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "alkylene" or "alkylene chain" refers to a straight or branched divalent hydrocarbon chain consisting solely of carbon and hydrogen, which is saturated or unsaturated (i.e., contains one or more double and/or triple bonds), and having from one to twenty carbon atoms, e.g., methylene, ethylene, propylene, n-butylene, ethenylene, propenylene, n-butenylene, propynylene, n-butynylene, and the like. The alkylene chain is attached via a single or double bond.

As used herein, the term "arylene" is used as understood by those skilled in the art, and refers to a divalent aryl group that is derived from an aryl group as provided herein, wherein two hydrogen as removed.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)CH$_3$.

Unless otherwise indicated, the term "aryl" means a monocyclic or multicyclic (e.g., bicyclic or tricyclic) ring system composed of carbon and hydrogen atoms, wherein the aryl has a fully delocalized pi-electron system throughout all the rings. An aryl moiety may comprise multiple rings bound or fused together. Examples of aryl moieties include, but are not limited to, anthracenyl, azulenyl, naphthyl, phenanthrenyl, and phenyl.

Unless otherwise indicated, the term "arylalkyl" or "arylalkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyridinium, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" or "heterocyclyl" refers to a non-aromatic monocyclic or polycyclic ring or ring system comprised of carbon, hydrogen and at least one heteroatom (e.g., N, O or S). A heterocycle may comprise multiple (i.e., two or more) rings fused or bound together. The fused heterocyclyls can be fused via two adjacent atoms. The fused heterocyclyls can also be bridged heterocyclyls, wherein the rings are fused via non-adjacent atoms. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

As used herein and unless otherwise indicated, the term "hydroxyalkyl" refers to an alkyl that is substituted with 1 or more hydroxy groups. Examples of hydroxyalkyl groups can have one of the following structures: —$(CH_2)_{1-4}$—OH and —$(CH_2)_{1-4}$—CH(OH)$CH_2)_{1-4}$—OH.

As used herein and unless otherwise indicated, the term "aminoalkyl" refers to an alkyl that is substituted with 1 or more amino groups. Examples of aminoalkyl groups can have one of the following structures: —$(CH_2)_{1-4}$—$NH_2$ and —$(CH_2)_{1-4}$—CH($NH_2$)—$(CH_2)_{1-4}$—$NH_2$.

As used herein, the π (pi) system of a molecule is used as understood by those skilled in the art. The (pi) system of a molecule is formed by the interaction of unhybridized p atomic orbitals on atoms that have $sp^2$- and sp-hybridization. The interaction that results in π bonding takes place between p orbitals that are adjacent by virtue of a σ bond joining the atoms and takes the form of side-to-side overlap of p orbitals.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol or the like. Hydrates are formed when the solvent is water or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, T. W. and Wuts, P. G. Mi, *Protective Groups in Organic Synthesis* ($3^{rd}$ ed., John Wiley & Sons: 1999); Larock, R. C., *Comprehensive Organic Transformations* ($2^{nd}$ ed., John Wiley & Sons: 1999).

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or —NHC(O)alkyl), amidinyl (—C(NH)NHalkyl or —C(NR)NH$_2$), amine (primary, secondary and tertiary such as alkylamino, arylamino, arylalkylamino; quaternary tetralkylammonium), aroyl, aryl, heteroaryl, heteroarylalkyl, aryloxy, azo, carbamoyl (—NHC(O)O-alkyl- or —OC(O)NH-alkyl), carbamyl (e.g., —C(O)NH$_2$, as well as —C(O)NH-alkyl, —C(O)NH-aryl, and —C(O)NH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxo, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHC(O)NH-alkyl-). Substitutions are optionally functionalized with one or more functional groups of hydroxyl, thiol, thioether, ketone, aldehyde, ester, ether, amine, imine, amide, nitro, carboxylic acid, disulfide, carbonate, isocyanate, carbodiimide, carboalkoxy, peroxo, anhydride, carbamate, and halogen.

Various embodiments of the present application are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The present description is not intended to be exhaustive nor limit the present application to the precise form disclosed and many modifications and variations are possible in the light of the above teachings. The embodiments described serve to explain the principles of the present application and its practical application and to enable others skilled in the art to utilize the present application in various embodiments and with various modifications as are suited to the particular use contemplated. Therefore, it is intended that the present application not be limited to the particular embodiments disclosed herein. Rather the various embodiments are meant to be illustrative and descriptive.

While particular embodiments of the present application have been shown and described, it will be obvious to those skilled in the art that, based upon the teachings herein, changes and modifications may be made without departing from this application and its broader aspects and, therefore, the appended claims are to encompass within their scope all such changes and modifications as are within the true spirit and scope of this application. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present application, or embodiments thereof, may alternatively be described using alternative terms such as "consisting of" or "consisting essentially of."

Therefore, it is an objective of the present application to provide compositions with an antimicrobial activity at a dosage range that is nontoxic to mammalian cells.

It is another objective of the present application to provide a method of treating bacterial infection in a mammalian subject, such as a subject that requires treatment for a bacterial infection, wherein the bacterial infection has developed resistance to typical drug treatment strategies.

Conjugated oligoelectrolytes (COEs) are a class of molecules that have been studied in bioelectrochemical systems, such as microbial fuel cells and electrobiosynthesis platforms. Twelve COEs with phenylenevinylene (PV) repeat units were examined with respect to their microbial membrane disrupting properties as a function of chemical structure. However, the toxicity toward mammalian cells has not been studied previously, which prevents the identification of COE candidates that are specifically promising for antimicrobial drug design.

Short COE molecules and their modifications are provided to increase their interactions with cells. In various embodiments, increasing the hydrophobic content enhances the interaction of the COE molecules with microbial cell walls and/or microbial membranes. In some embodiments, the disclosed COEs exhibit significant antimicrobial efficacy against both Gram-negative and Gram-positive bacteria relative to common antibiotics, while displaying minimal toxicity toward RAW264.7 murine macrophages, relative to all COE variations reported previously. To some specific microbes (such as PA ATCC 10145, MRSA USA300, MRSA MT3315), the COEs described herein, such as COE2-2hexyl, show superior efficacy relative to conventional antibiotics.

Formulae

Conjugated oligoelectrolytes (COEs) are provided to intercalate into cell membranes. In some embodiments, the COEs have a general structure of Formula 1:

(Formula 1)

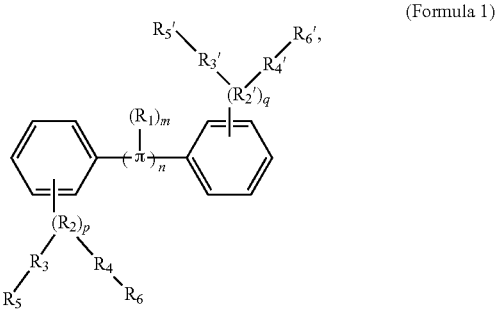

wherein π represents a pi conjugation structure, with exemplary structure as follows:

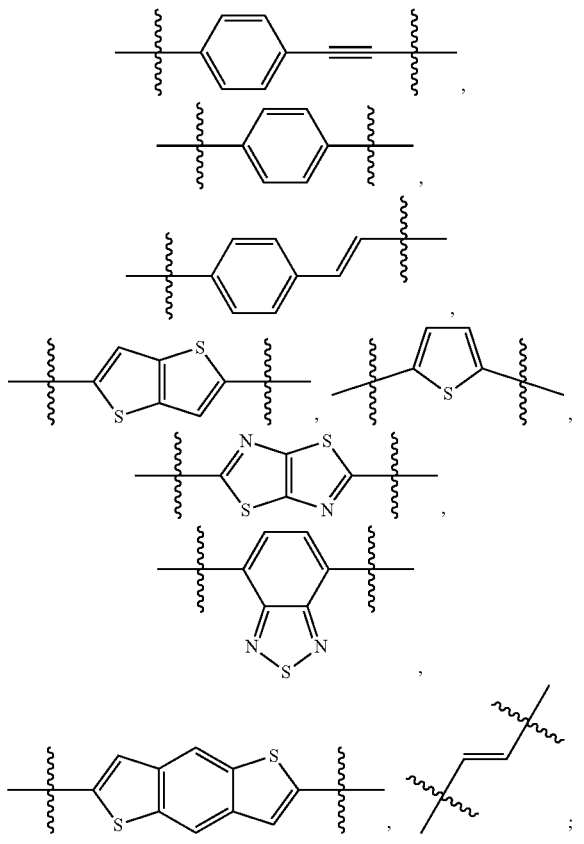

and where n is 0, 1, 2, 3, 4, 5, 6, 7, 8, 9, or 10; m is 0, 1, 2, 3 or 4 and in which $R_1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl or aryl; p and q are, independently, 1, 2, 3, 4 or 5 and in which $R_2$ and $R_{2'}$ are, independently, $C_1$-$C_{20}$ alkynyl chain, —O—, —S—, —CO—, —COO—, —OCO—, —SO—, —SO$_2$—, —N— or —NCO—, and wherein $R_3$, $R_{3'}$, $R_4$ and $R_{4'}$ are the same or different and constitute a straight-chain, branched or cyclic, substituted or unsubstituted $C_1$-$C_{20}$ alkyl, $C_2$-$C_{20}$ alkenyl, $C_2$-$C_{20}$ alkynyl or aryl; $R_5$, $R_{5'}$, $R_6$ and $R_{6'}$ are the same or different pendant group, which could be cationic, include but not limited to ammonium, pyridinium and phosphonium, or anionic, such as —CO$_2^-$, —SO$_3^-$; and one or more of the unsubstituted aromatic carbon atoms may be replaced by nitrogen, oxygen, and/or sulfur atoms.

In some embodiments, the COEs can have a general structure of Formula 2:

(Formula 2)

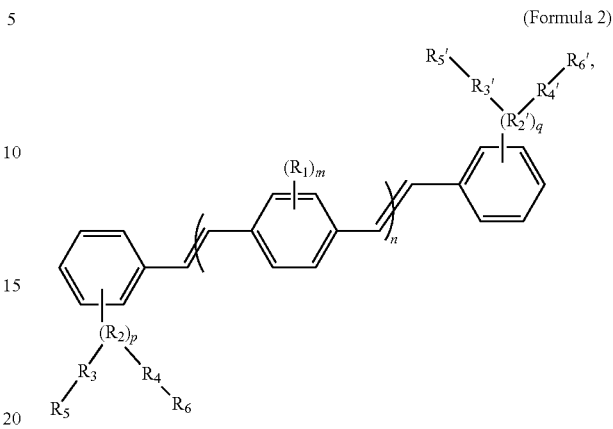

where n is 0, 1, 2, 3, 4, 5, 6, 7, 8, 9, or 10; m is 0, 1, 2, 3 or 4 and in which $R_1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl or aryl, optionally two or more $R_1$ combine to form a cyclic or aromatic group; p and q are, independently, 1, 2, 3, 4 or 5 and in which $R_2$ and $R_{2'}$ are, independently, $C_1$-$C_{20}$ alkynyl chain, —O—, —S—, —CO—, —COO—, —OCO—, —SO—, —SO$_2$—, —N— or —NCO—, and wherein $R_3$, $R_{3'}$, $R_4$ and $R_{4'}$ are the same or different and constitute a straight-chain, branched or cyclic, substituted or unsubstituted $C_1$-$C_{20}$ alkyl, $C_2$-$C_{20}$ alkenyl, $C_2$-$C_{20}$ alkynyl or aryl; $R_5$, $R_{5'}$, $R_6$ and $R_{6'}$ are the same or different pendant group, which could be cationic, include but not limited to ammonium, pyridinium and phosphonium, or anionic, such as —CO$_2^-$, —SO$_3^-$; chemical bonds depicted with one solid line parallel to one dashed line encompass both single and double (e.g., aromatic) bonds, if valences permit; and one or more of the unsubstituted aromatic carbon atoms may be replaced by nitrogen, oxygen, and/or sulfur atoms. The repeating core unit in the parenthesis with a subscript, n, may be optionally replaced with any of the following core structures:

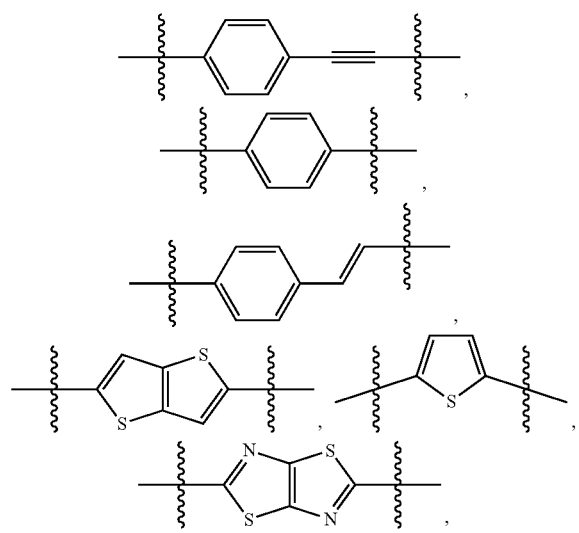

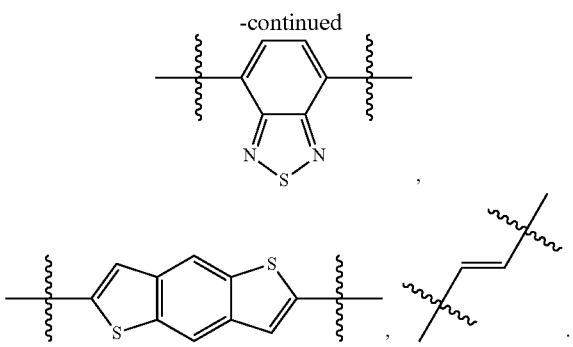

In other embodiments, the COEs can have a structure of Formula 3,

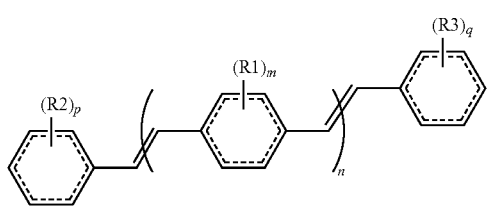

(Formula 3)

where n is 0, 1, 2, 3, 4, 5, 6, 7, 8, 9, or 10; m is 0, 1, 2, 3 or 4 and in which $R_1$ is, independently, an electron withdrawing group or an electron donating group, optionally two or more $R_1$ combine to form a cyclic or aromatic group; p and q are, independently, 1, 2, 3, 4 or 5 and in which $R_2$ and $R_3$ are, independently, —X($R_4$) wherein —X— represents a single bond, —O—, —S—, —CO—, —COO—, —OCO—, —SO—, —SO$_2$—, —N($R_5$)— or —N($R_5$)CO—, and wherein $R_4$ and $R_5$ are the same or different and constitute a straight-chain, branched or cyclic, substituted or unsubstituted $C_1$-$C_{20}$ alkyl, $C_2$-$C_{20}$ alkenyl, $C_2$-$C_{20}$ alkynyl or aryl; chemical bonds depicted with one solid line parallel to one dashed line encompass both single and double (e.g., aromatic) bonds, if valences permit; and one or more of the unsubstituted aromatic carbon atoms may be replaced by nitrogen and/or sulfur atoms. In various embodiments, at least one of $R_4$ and $R_5$ is substituted $C_1$-$C_{20}$ alkyl, $C_2$-$C_{20}$ alkenyl, $C_2$-$C_{20}$ alkynyl or aryl, where the substitution includes a cationic group. In further embodiments, the cationic group is a quaternary ammonium or a pyridinium cationic group, which is optionally further substituted with $C_1$-$C_{20}$ alkyl, $C_2$-$C_{20}$ alkenyl, $C_2$-$C_{20}$ alkynyl or aryl. The counter ions to the cationic group may be a charge compensating anion, including but not limited to halides (I$^-$, Br$^-$, Cl$^-$, or F$^-$), organic anion, BIm$_4^-$, B(ArF)$_4^-$. The counter ions to the anionic group could be alkaline metal, Na$^+$, K$^+$, Ca$^{2+}$, or organic cation, tetralkyl ammoniums, pyridiums. In some aspects, these COEs have a structural Formula 3-a:

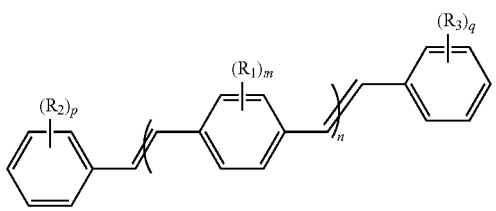

In some embodiments, the COEs have a structure of Formula 3-a, wherein n is 0, 1, 2, 3, 4, 5 or 6; m is 0, 1, 2, 3 or 4; $R_1$ is F (fluorine atom); p=q=1, 2, 3, 4 or 5 and $R_2$=$R_3$=—X($R_4$), wherein —X— represents a single bond, —O—, —S—, —CO—, —COO—, —OCO—, —SO—, —SO$_2$—, —N($R_5$)— or —N($R_5$)CO—, and wherein $R_4$ and $R_5$ are the same or different and constitute a substituted $C_1$-$C_{20}$ alkyl, $C_2$-$C_{20}$ alkenyl, $C_2$-$C_{20}$ alkynyl or aryl, and the substitution is a quaternary ammonium, a pyridinium cationic group, a imidazolium cationic group or a pyrrolidinium cationic group, which is optionally substituted with a $C_1$-$C_{20}$ alkyl, $C_2$-$C_{20}$ alkenyl, $C_2$-$C_{20}$ alkynyl or aryl.

In some embodiments, m can be 0. In other embodiments, m can be 1. In still other embodiments, m can be 2. In yet still other embodiments, m can be 3. In some embodiments, m can be 4. When m is 1 or 4 greater, each $R_1$ can be independently a substituted or unsubstituted $C_1$-$C_{20}$ alkyl, $C_2$-$C_{20}$ alkenyl, $C_2$-$C_{20}$ alkynyl, aryl, alkoxy, amine, or thioether.

In some embodiments, n can be 0. In other embodiments, n can be 1. In still other embodiments, n can be 2.

In some embodiments, p can be 1, 2 or 3; and q can be 1, 2 or 3. In some embodiments, p and q can be each be 1. In other embodiments, p and q can be each be 2. In still other embodiments, p and q can be each be 3.

As provided herein, $R_2$ and $R_3$ can be each —X($R_4$). In some embodiments, including those of the previous paragraph, $R_2$ and $R_3$ can be each —O($R_4$). When $R_2$ and $R_3$ are each —O($R_4$), then each $R_4$ can be a substituted $C_1$-$C_{20}$ alkyl. For example, $R_2$ and $R_3$ are each —O($R_4$), then each $R_4$ can be a substituted $C_3$-$C_{10}$ alkyl; or $R_2$ and $R_3$ are each —O($R_4$), then each $R_4$ can be a substituted $C_4$-$C_8$ alkyl.

The compositions having a general structure of Formula 3-a have an oligophenylenevinylene π-conjugated structure. In various embodiments, the composition preferentially inhibits bacterial over mammalian cell growth, such that they are bactericidal yet safe to mammalian cells.

In some embodiments, the COEs of Formula 3-a have different numbers for p and q (each independently selected from 1, 2, 3, 4 and 5), and/or different chemical moieties for $R_2$ and $R_3$, each independently being —X($R_4$), wherein —X— represents a single bond, —O—, —S—, —CO—, —COO—, —OCO—, —SO—, —SO$_2$—, —N($R_5$)— or —N($R_5$)CO—, and wherein $R_4$ and $R_5$ are the same or different and constitute a substituted $C_1$-$C_{20}$ alkyl, $C_2$-$C_{20}$ alkenyl, $C_2$-$C_{20}$ alkynyl or aryl, and the substitution is a quaternary ammonium or a pyridinium cationic group, wherein the quaternary ammonium or pyridinium is optionally substituted with a $C_1$-$C_{20}$ alkyl, $C_2$-$C_{20}$ alkenyl, $C_2$-$C_{20}$ alkynyl or aryl.

In various embodiments, the COEs have a structure of Formula 4, wherein n is 0, 1, 2, 3, 4, 5 or 6; m is 0, 1, 2, 3 or 4 and in which R is, independently, an electron withdrawing group or an electron donating group, optionally two or more $R_1$ combine to form a cyclic or aromatic group; x and u represent the numbers of substitutions on the phenyl group and are, independently, 1, 2, 3, 4, or 5; $R_6$ and $R_7$ are, independently, —O—, —S—, —C(O)—, —C(O)O—, —OC(O)—, —S(O)—, —S(O)$_2$—, —N—, —NC(O)—, —C(O)N—; y and v represent the numbers of substitutions on $R_7$ and $R_6$, respectively, and are, independently, 1 for O and 1 or 2 for N; $R_8$ and $R_9$ are, independently, $C_1$-$C_{20}$ alkyl, $C_2$-$C_{20}$ alkenyl, $C_2$-$C_{20}$ alkynyl or aryl; N$^\oplus$ each represents a quaternary ammonium or a pyridinium cationic group; z and w represent the numbers of substitutions on N$^\oplus$ and are, independently, 0, 1, 2, 3, 4 or 5, if valences permit; $R_{10}$ and $R_{11}$ are, independently, $C_1$-$C_{20}$ alkyl, $C_2$-$C_{20}$ alkenyl, $C_2$-$C_{20}$ alkynyl or aryl; and the counter ions is I⁻, Br⁻, Cl⁻, F⁻, organic anion, BIm$_4^-$ or B(ArF)$_4^-$.

Formula 4

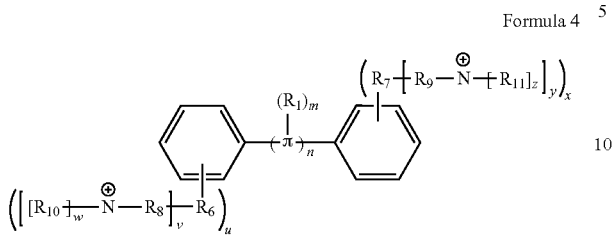

In some embodiments, π can be aryl or heteroaryl. For example, π can be a phenyl, a monocyclic heteroaryl or a bicyclic heteroaryl. In some embodiments, n can be

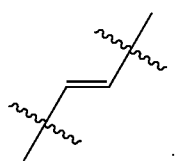 [SMILES: */C=C/*]

In some embodiments π can be

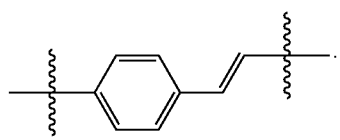 [SMILES: */C=C/c1ccc(*)cc1]

In some embodiments, π can be

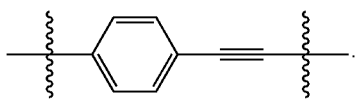

In some embodiments, π can be

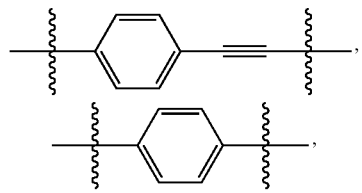

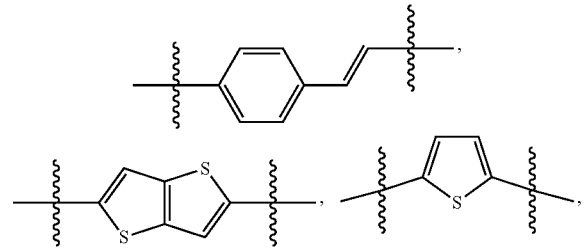

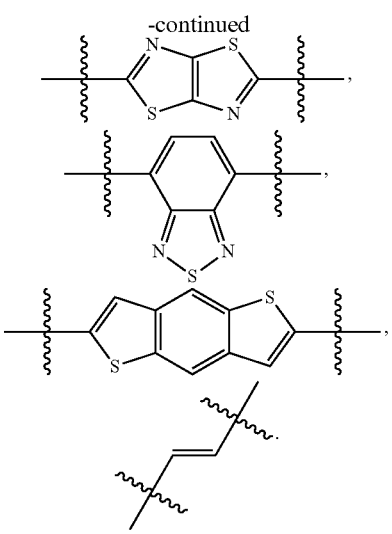

In some embodiments, n can be 1. In some embodiments, when n is 1, then π can be

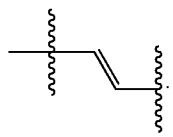 [SMILES: */C=C/*]

In other embodiments, n can be 3. In some embodiments, when n is 3, then π can be

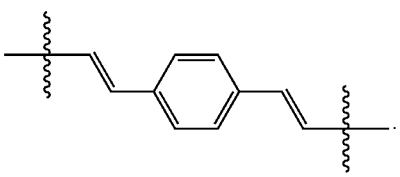 [SMILES: */C=C/c1ccc(/C=C/*)cc1]

In still other embodiments, n can be 5. In some embodiments when n is 5, then π can be

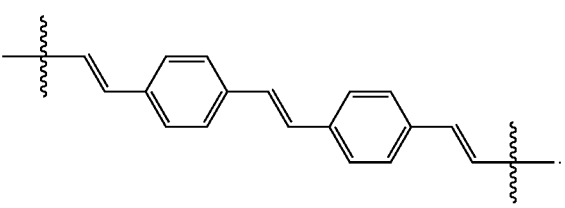 [SMILES: */C=C/c1ccc(/C=C/c2ccc(/C=C/*)cc2)cc1]

In some embodiments, m can be 0. In other embodiments, m can be 1. In still other embodiments, m can be 2. In yet still other embodiments, m can be 3. In some embodiments, m can be 4. When m is 1 or 4 greater, each R$_1$ can be independently a substituted or unsubstituted C$_1$-C$_{20}$ alkyl, C$_2$-C$_{20}$ alkenyl, C$_2$-C$_{20}$ alkynyl, aryl, alkoxy, amine, or thioether.

The phenyl rings shown in Formula 4 can be substituted multiple times. In some embodiments, x can be 2. In other embodiments, x can be 3. In some embodiments, u can be 2.

In other embodiments, u can be 3. The phenyl group can be substituted at the meta-positions and/or the para-positions. When x and u are each 2 and each phenyl group is substituted at the meta-positions, Formula 4 can have the structure

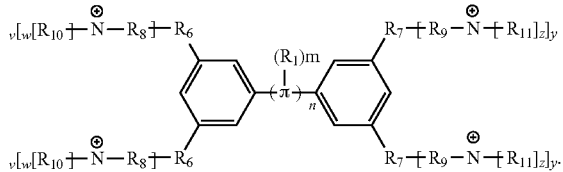

Further, when x and u are each 3 and each phenyl group is substituted at the meta- and para-positions, Formula 4 can have the structure

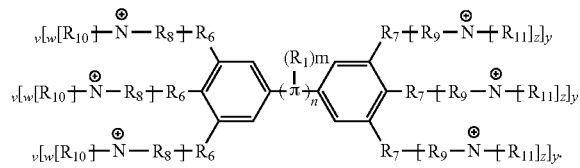

In some embodiments, $R_6$ and $R_7$ are, independently, O or N. In some embodiments, each $R_7$ can be O; and y and v can be each 1. In other embodiments, each $R_7$ can be N; and y and v can be each 2. In other embodiments, when each $R_7$ can be O; x and u can be 2; and y and v can be each 1, Formula 4 can have the structure:

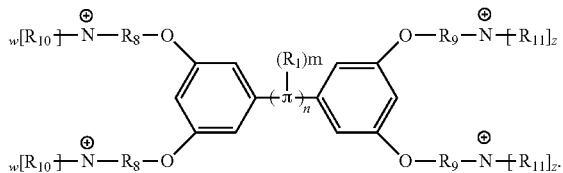

In other embodiments, when each $R_7$ can be O; x and u can be 3; and y and v can be each 1, Formula 4 can have the structure:

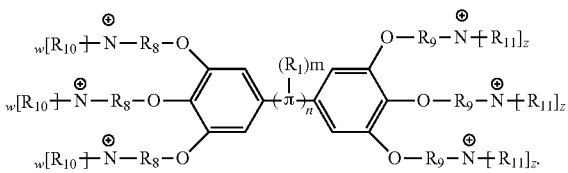

In still other embodiments, when each $R_7$ can be N; x and u can be 1; and y and v can be each 2, Formula 4 can have the structure:

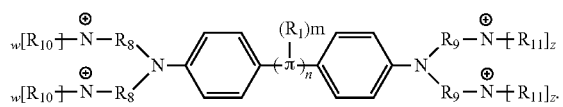

In some embodiments, $R_8$ and $R_9$ can be each $C_1$-$C_{20}$ alkyl. In some embodiments, $R_8$ and $R_9$ can be each $C_2$-$C_{10}$ alkyl. In other embodiments, $R_8$ and $R_9$ can be each $C_3$-$C_8$ alkyl. In still other embodiments, $R_8$ and $R_9$ can be each $C_4$-$C_6$ alkyl.

In some embodiments, each z can be 3. In some embodiments, each w can be 3. In some embodiments, each z and each w can be 3. As provided herein, $R_{10}$ and $R_{11}$ are, independently, $C_1$-$C_{20}$ alkyl, $C_2$-$C_{20}$ alkenyl, $C_2$-$C_{20}$ alkynyl or aryl. In some embodiments, $R_{10}$ can be $C_1$-$C_{20}$ alkyl. In some embodiments, $R_{11}$ can be $C_1$-$C_{20}$ alkyl. In some embodiments $R_{10}$ and $R_{11}$ can be $C_1$-$C_{20}$ alkyl. For example, $R_{10}$ and $R_{11}$ can be methyl, ethyl, n-propyl, isopropyl, n-butyl, isobutyl, tert-butyl, pentyl (branched or straight chained) or hexyl (branched or straight chained). In some embodiments, each z and each w can be 3; and each $R_{10}$ and each $R_{11}$ can be $C_1$-$C_{20}$ alkyl such as those described herein. In some embodiments, each z and each w can be 3; and each $R_{10}$ and each $R_{11}$ can be $C_1$-$C_6$ alkyl. In some embodiments, each z and each w can be 3; and each $R_{10}$ and each $R_{11}$ can be methyl. In other embodiments, each z and each w can be 3; and each $R_{10}$ and each $R_{11}$ can be $C_2$-$C_6$ alkyl (for example, ethyl, n-propyl, isopropyl, n-butyl, isobutyl, tert-butyl, pentyl (branched or straight chained) or hexyl (branched or straight chained)).

In further embodiments, the COEs of Formula 4 have identical chemical moieties on both ends of the oligophenylenevinylene. That is, $R_6$=$R_7$, $R_8$=$R_9$, $R_{10}$=$R_1$, x=u, y=v, and z=w. In some embodiments, n is an integer between 0 and 3, between 0 and 2, or is 0 or 1.

In some embodiments, the COEs have a structural Formula 5:

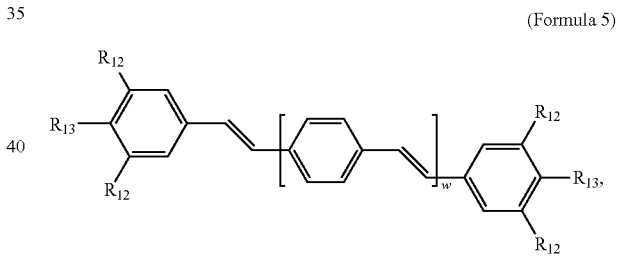

(Formula 5)

wherein each $R_{12}$ is independently —O—$R_{14}$—N($R_{15}$)$_3$ or —O—$R_{14}$-$R_{17}$; each $R_{13}$ is independently H or $R_{12}$; $R_{14}$ and $R_{16}$ are independently $C_2$-$C_{10}$ alkyl; each $R_{15}$ is independently H, $C_1$-$C_{10}$ alkyl, hydroxyalkyl, aminoalkyl,

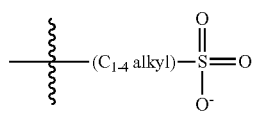

or —(($CH_2$)$_2$—O)$_{1-4}$—$CH_3$, or two $R_{15}$ are taken together with the nitrogen to which they are attached to form a monocyclic N-linked heterocyclyl or a bicyclic N-linked heterocyclyl; $R_{17}$ is an unsubstituted or substituted N-linked pyridinyl, —($C_2$-$C_3$ alkyl)N($R_{18}$)$_3$ or —NH—(=NH)NH$_2$; each $R_{18}$ is independently $C_2$-$C_{10}$ alkyl, hydroxyalkyl, aminoalkyl,

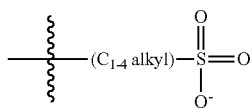

or —((CH$_2$)$_2$—O)$_{1-4}$—CH$_3$; w is 0, 1 or 2; and the counter ions include I$^-$, Br$^-$, Cl$^-$, F$^-$, organic anion, BIm$_4^-$ or B(ArF)$_4^-$.

The linkage between the phenyl rings and the terminal group (for example, N(R$_{15}$)$_3$ and R$_{17}$) can vary. For example, the alkyl can be 2 to 10 carbons in length. When R$_{12}$ is —O—R$_{14}$—N(R$_{15}$)$_3$, the alkyl can be a C$_2$-C$_{10}$ alkyl. In some embodiments, R$_{14}$ can be —(CH$_2$)$_2$—. In other embodiments, R$_{14}$ can be —(CH$_2$)$_3$—. In still other embodiments, R$_{14}$ can be —(CH$_2$)$_4$—. In yet still other embodiments, R$_{14}$ can be —(CH$_2$)$_5$—. In some embodiments, R$_{14}$ can be —(CH$_2$)$_6$—. In other embodiments, R$_{14}$ can be —(CH$_2$)$_7$—. In still other embodiments, R$_{14}$ can be —(CH$_2$)$_8$—. In yet still embodiments, R$_{14}$ can be —(CH$_2$)$_9$—. In some embodiments, R$_{14}$ can be —(CH$_2$)$_{10}$—. In some embodiments, one or more of the hydrogens of the R$_{14}$ groups can be substituted with one or more —OH, —NH$_2$, —SO$_3^-$, C$_1$-C$_{20}$ alkyl, or —N$^+$(CH$_3$)$_2$R$_{7a}$, wherein R$_{7a}$ can be C$_1$-C$_{20}$ alkyl.

In some embodiments, each R$_{12}$ can be independently —O—R$_{14}$—N(R$_{15}$)$_3$. The terminal group of N(R$_1$)$_3$ can be various substituents. In some embodiments, each R$_{15}$ can be the same. In other embodiments, each R$_{15}$ can be different. In some embodiments, each R$_{15}$ can be independently C$_1$-C$_{10}$ alkyl. As an example, each R$_{15}$ can be methyl. As other examples, each R$_{15}$ can be C$_2$-C$_{10}$ alkyl. In some embodiments, each R$_{15}$ can be C$_2$-C$_8$ alkyl. In other embodiments, each R$_{15}$ can be C$_4$-C$_6$ alkyl. In still other embodiments, each R$_{15}$ can be H.

Alternatively, two R$_{15}$ can be taken together with the nitrogen to which they are attached to form a monocyclic N-linked heterocyclyl or a bicyclic N-linked heterocyclyl. In some embodiments, two R$_{15}$ can be taken together with the nitrogen to which they are attached to form a monocyclic N-linked heterocyclyl; and the remaining R$_{15}$ can be C$_1$-C$_{10}$ alkyl. The monocyclic N-linked heterocyclyl can be 5-membered or a 6-membered monocyclic N-linked heterocyclyl. Examples of monocyclic N-linked heterocyclyls include:

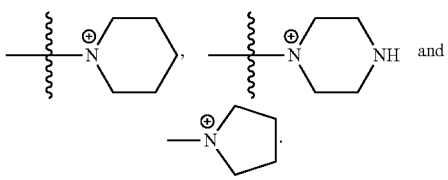

The monocyclic N-linked heterocyclyl, including those specific monocyclic N-linked heterocyclyls, can be unsubstituted or substituted. When substituted, the non-hydrogen group can replace any hydrogen of the monocyclic N-linked heterocyclyl. In some embodiments, two R$_{15}$ can be taken together with the nitrogen to which they are attached to form a monocyclic N-linked heterocyclyl described herein, and the remaining R$_{15}$ can be methyl.

In other embodiments, two R$_{15}$ can be taken together with the nitrogen to which they are attached to form a bicyclic N-linked heterocyclyl; and the remaining R$_{15}$ can be C$_1$-C$_{10}$ alkyl. The bicyclic N-linked heterocyclyl can be a fused-bicyclic N-linked heterocyclyl, such as a bridged-bicyclic N-linked heterocyclyl. The size of the bicyclic N-linked heterocyclyl can vary. In some embodiments, the bicyclic N-linked heterocyclyl can be a 7- or 8-membered bicyclic N-linked heterocyclyl. Some examples of bicyclic N-linked heterocyclyls include

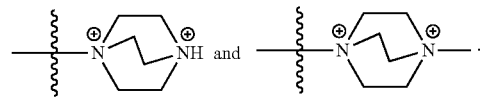

The bicyclic N-linked heterocyclyl, including those specific bicyclic N-linked heterocyclyls, can be unsubstituted or substituted. When substituted, the non-hydrogen group can replace any hydrogen of the monocyclic N-linked heterocyclyl.

In addition to those R$_{15}$ groups described herein, various R$_{15}$ group can be present. In some embodiments, one or more R$_{15}$ groups can be hydroxyalkyl. As described herein, one or more hydroxy groups can be present on a hydroxyalkyl. In some embodiments, the hydroxyalkyl can be —(CH$_2$)$_{1-4}$—OH. In other embodiments, the hydroxyalkyl can be

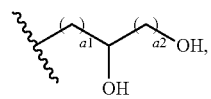

wherein a1 and a2 can be independently 1 or 2. In other embodiments, one or more R$_{15}$ groups can be aminoalkyl, such as a —(CH$_2$)$_{1-4}$—NH$_2$. In still other embodiments, one or more R$_{15}$ groups can be.

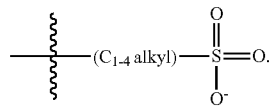

In yet still other embodiments, one or more R$_{15}$ groups can be —((CH$_2$)$_2$—O)$_{1-4}$—CH$_3$. For example, when an R$_{15}$ group is —((CH$_2$)$_2$—O)$_{1-4}$—CH$_3$, one or more R$_{15}$ groups can be

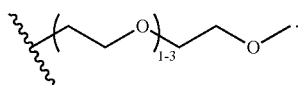

As described herein, one or more R$_{15}$ groups can be hydroxyalkyl, aminoalkyl,

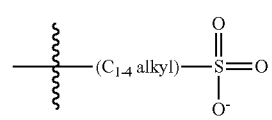

or —((CH$_2$)$_2$—O)$_{1-4}$—CH$_3$. For example, one or more R$_{15}$ groups can be hydroxyalkyl, aminoalkyl,

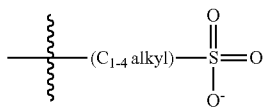

or —((CH$_2$)$_2$—O)$_{1-4}$—CH$_3$; and the remaining R$_{15}$ groups can be C$_1$-C$_{10}$ alkyl. In some embodiments, one R$_{15}$ group can be hydroxyalkyl, aminoalkyl,

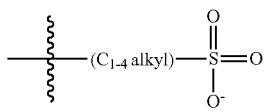

or —((CH$_2$)$_2$—O)$_{1-4}$—CH$_3$; and two R$_{15}$ groups can be independently C$_1$-C$_{10}$ alkyl. In other embodiments, two R$_{15}$ groups can be hydroxyalkyl, anminoalkyl,

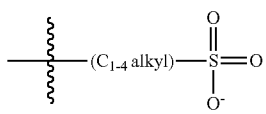

or —((CH$_2$)$_2$—O)$_{1-4}$—CH$_3$; and one R$_{15}$ group can be C$_1$-C$_{10}$ alkyl. In some embodiments, two R$_{15}$ groups can be hydroxyalkyl, aminoalkyl,

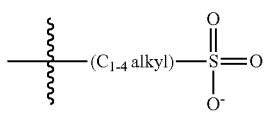

or —((CH$_2$)$_2$—O)$_{1-4}$—CH$_3$; and one R$_{15}$ group can be C$_4$-C$_6$ alkyl. In some embodiments, two R$_{15}$ groups can be hydroxyalkyl, aminoalkyl,

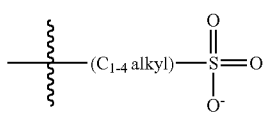

or —((CH$_2$)$_2$—O)$_{1-4}$—CH$_3$; and one R$_{15}$ group can be C$_1$-C$_4$ alkyl.

As provided herein, in some embodiments, each R$_{12}$ can be independently —O—R$_{14}$-R$_{17}$, wherein R$_{17}$ can be an unsubstituted or substituted N-linked pyridinyl, —(C$_2$-C$_3$ alkyl)N(R$_{15}$)$_3$ or —NH—(=NH)NH$_2$. In some embodiments, R$_{14}$ can be a C$_2$-C$_{10}$ alkyl as described in paragraph [0083]. In some embodiments, R$_{17}$ can be an unsubstituted N-linked pyridinyl. In other embodiments, R$_{17}$ can be a substituted N-linked pyridinyl. When the N-linked pyridinyl is substituted, the pyridinyl can be substituted one or more times with a substituent independently selected from an electron-donating group and electron-withdrawing group. In some embodiments, N-linked pyridinyl can be substituted with a substituent selected from a substituted or unsubstituted C$_1$-C$_{20}$ alkyl, C$_2$-C$_{20}$ alkenyl, C$_2$-C$_{20}$ alkynyl, aryl, alkoxy, amine, or thioether. In some embodiments, R$_{17}$ can be —(C$_2$-C$_3$ alkyl)N(R$_{18}$)$_3$. For example, R$_{17}$ can be —(CH$_2$)$_2$N(R$_{18}$)$_3$ or —(CH$_2$)$_3$N(R$_{18}$)$_3$.

The R$_{18}$ groups can vary as described herein. In some embodiments, each Rig can be the same. In other embodiments, each R$_{18}$ can be different. In some embodiments, each R$_{18}$ can be independently C$_1$-C$_{10}$ alkyl. In some embodiments, each R$_{18}$ can be methyl. In other embodiments, each R$_{18}$ can be C$_2$-C$_{10}$ alkyl. In some embodiments, each R$_{18}$ can be C$_2$-C$_8$ alkyl. In other embodiments, each R$_{18}$ can be C$_4$-C$_6$ alkyl.

As with R$_{15}$, two R$_{18}$ can be taken together with the nitrogen to which they are attached to form a monocyclic N-linked heterocyclyl or a bicyclic N-linked heterocyclyl. In some embodiments, two R$_{18}$ can be taken together with the nitrogen to which they are attached to form a monocyclic N-linked heterocyclyl; and the remaining R$_{18}$ can be C$_1$-C$_{10}$ alkyl. The monocyclic N-linked heterocyclyl can be 5-membered or a 6-membered monocyclic N-linked heterocyclyl, such as those described herein. The monocyclic N-linked heterocyclyl can be unsubstituted or substituted. In some embodiments, two R$_{18}$ can be taken together with the nitrogen to which they are attached to form a monocyclic N-linked heterocyclyl described herein, and the remaining R$_{18}$ can be methyl.

In other embodiments, two R$_{18}$ can be taken together with the nitrogen to which they are attached to form a bicyclic N-linked heterocyclyl; and the remaining R$_{18}$ can be C$_1$-C$_{10}$ alkyl. The bicyclic N-linked heterocyclyl can be a fused-bicyclic N-linked heterocyclyl, such as a bridged-bicyclic N-linked heterocyclyl. The size of the bicyclic N-linked heterocyclyl can vary. In some embodiments, the bicyclic N-linked heterocyclyl can be a 7- or 8-membered bicyclic N-linked heterocyclyl. The bicyclic N-linked heterocyclyl can be unsubstituted or substituted. When substituted, the non-hydrogen group can replace any hydrogen of the monocyclic and/or bicyclic N-linked heterocyclyls. The following are examples monocyclic N-linked heterocyclyls and bicyclic N-linked heterocyclyls formed when two R$_{18}$ can be taken together with the nitrogen to which they are attached:

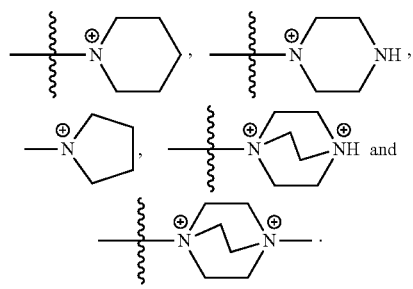

In some embodiments, one or more R$_{18}$ groups can be hydroxyalkyl. As described herein, one or more hydroxy groups can be present on a hydroxyalkyl. In some embodiments, the hydroxyalkyl can be —(CH$_2$)$_{14}$—OH or

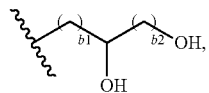

wherein b1 and b2 can be independently 1 or 2. In other embodiments, one or more R$_1$ groups can be aminoalkyl, such as a —(CH$_2$)$_{1-4}$—NH$_2$. In still other embodiments, one or more R$_{18}$ groups can be

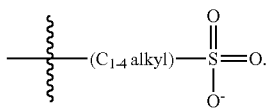

In yet still other embodiments, one or more $R_{18}$ groups can be —$((CH_2)_2—O)_{1-4}$—$CH_3$, such as

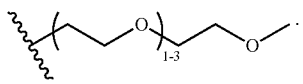

As described herein, one or more $R_{18}$ groups can be hydroxyalkyl, aminoalkyl,

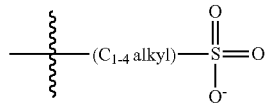

or —$((CH_2)_2—O)_{1-4}$—$CH_3$. For example, one or more $R_{18}$ groups can be hydroxyalkyl, aminoalkyl,

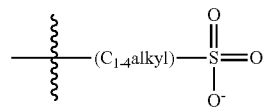

or —$((CH_2)_2—O)_{1-4}$—$CH_3$; and the remaining $R_{18}$ groups can be $C_1$-$C_{10}$ alkyl. In some embodiments, one $R_{18}$ group can be hydroxyalkyl, aminoalkyl,

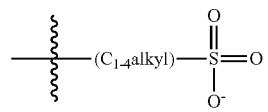

or —$((CH_2)_2—O)_{1-4}$—$CH_3$; and two $R_{18}$ groups can be independently $C_1$-$C_{10}$ alkyl. In other embodiments, two $R_{18}$ groups can be hydroxyalkyl, aminoalkyl,

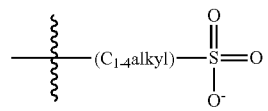

or —$((CH_2)_2—O)_{1-4}$—$CH_3$; and one $R_{15}$ group can be $C_1$-$C_{10}$ alkyl. In some embodiments, two $R_{15}$ groups can be hydroxyalkyl, aminoalkyl,

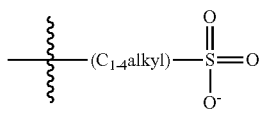

or —$((CH_2)_2—O)_{1-4}$—$CH_3$; and one $R_{18}$ group can be $C_4$-$C_6$ alkyl. In some embodiments, two $R_{18}$ groups can be hydroxyalkyl, aminoalkyl,

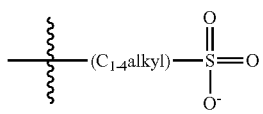

or —$((CH_2)_2—O)_{1-4}$—$CH_3$; and one $R_{15}$ group can be $C_1$-$C_4$ alkyl.

As described herein, w can be 0, 1 or 2. In some embodiments, when w is 0, the compound of Formula 5 can have the structure:

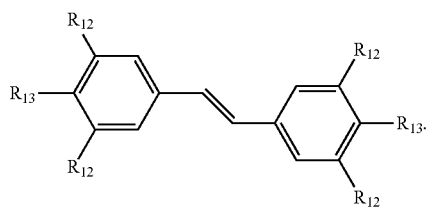

In other embodiments, when w is 1, the compound of Formula 5 can have the structure:

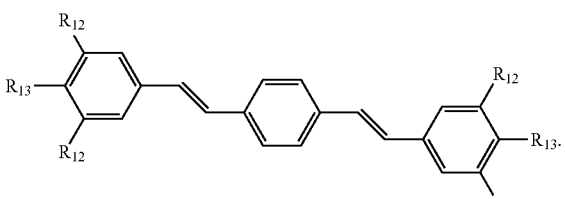

In still other embodiments, when w is 2, the compound of Formula 5 can have the structure:

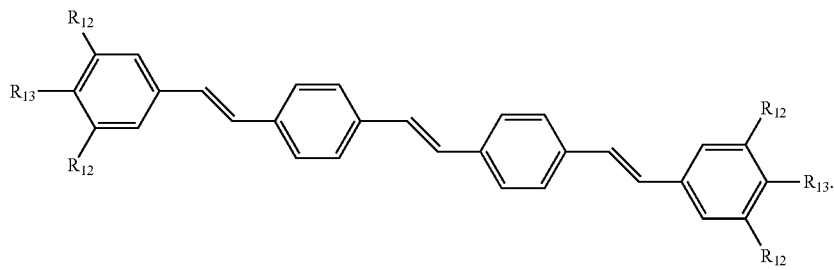

In some embodiments, when each $R_{12}$ is —O—$R_{14}$—N($CH_3$)$_3$ and $R_{13}$ is H, then $R_{14}$ is not $C_3$ or $C_6$ alkyl.

In some embodiments, when $R_{12}$ is -O—$R_{14}$-$R_{17}$, then $R_{17}$ cannot be —NH—(=NH)$NH_2$. In some embodiments, when $R_{14}$ is $C_3$ alkyl, then $R_{15}$ cannot be methyl. In some embodiments, when $R_{12}$ is O—$R_{14}$-$R_{17}$, then $R_{17}$ cannot be an unsubstituted or substituted N-linked pyridinyl. In some embodiments, each $R_{15}$ cannot be methyl. In some embodiments, including those of this paragraph, $R_{14}$ cannot be $C_3$ alkyl. In some embodiments, including those of this paragraph, $R_{14}$ cannot be $C_6$ alkyl. In some embodiments, $R_1$ cannot be halide, such as F. In some embodiments, $R_1$ cannot be alkoxy. In some embodiments, $R_1$ cannot be cyano.

In some embodiments, the COEs have a structural Formula 6:

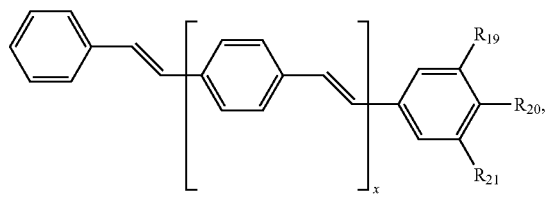

(Formula 6)

wherein $R_{19}$, $R_{20}$ and $R_{21}$ are independently —O—$R_{22}$—N($R_{23}$)$_3$ or —O—$R_{24}$-$R_{25}$; each $R_{22}$ and each $R_{24}$ is independently $C_2$-$C_{10}$ alkyl; each $R_{23}$ is independently H, $C_1$-$C_{10}$ alkyl, hydroxyalkyl, aminoalkyl,

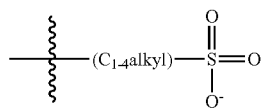

or —(($CH_2$)$_2$—O)$_{1-4}$—$CH_3$, or two $R_{23}$ are taken together with the nitrogen to which they are attached to form a monocyclic N-linked heterocyclyl or a bicyclic N-linked heterocyclyl; $R_{25}$ is an unsubstituted or substituted N-linked pyridinyl, —($C_{2-3}$ alkyl)N($R_{26}$)$_3$ or —NH—(=NH)$NH_2$; each $R_{26}$ is independently $C_2$-$C_{10}$ alkyl, hydroxyalkyl, aminoalkyl,

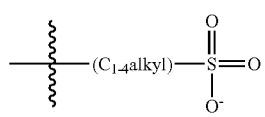

or —(($CH_2$)$_2$—O)$_{1-4}$—$CH_3$; x is 0, 1 or 2; and the counter ions include I$^-$, Br$^-$, Cl$^-$, F$^-$, organic anion, BIm$_4^-$ or B(ArF)$_4^-$.

In some embodiments, each of $R_{19}$, $R_{20}$ and $R_{21}$ can be independently —O—$R_{22}$—N($R_{23}$)$_3$. As described herein, $R_{22}$ can be $C_2$-$C_{10}$ alkyl. In some embodiments, $R_{22}$ can be —($CH_2$)$_2$—. In other embodiments, $R_{22}$ can be —($CH_2$)$_3$—. In still other embodiments, $R_{22}$ can be —($CH_2$)$_4$—. In yet still other embodiments, $R_{22}$ can be —($CH_2$)$_5$—. In some embodiments, $R_{22}$ can be —($CH_2$)—. In other embodiments, $R_{22}$ can be —($CH_2$)$_7$—. In still other embodiments, $R_{22}$ can be —($CH_2$)$_8$—. In yet still other embodiments, $R_{22}$ can be —($CH_2$)$_9$—. In some embodiments, $R_{22}$ can be —($CH_2$)$_{10}$—. In some embodiments, one or more of the hydrogens of the $R_{22}$ groups can be substituted with one or more —OH, —$NH_2$, —$SO_3^-$—, $C_1$-$C_{20}$ alkyl, or —N($CH_3$)$_2R_{7b}$, wherein $R_{7b}$ can be $C_1$-$C_{20}$ alkyl.

The terminal group of N($R_{23}$)$_3$ can be a variety of substituents. In some embodiments, each $R_{23}$ can be the same. In other embodiments, each $R_{23}$ can be different. In some embodiments, each $R_{23}$ can be independently $C_1$-$C_{10}$ alkyl. As an example, each $R_{23}$ can be methyl. As other examples, each $R_{23}$ can be $C_2$-$C_{10}$ alkyl. In some embodiments, each $R_{23}$ can be $C_2$-$C_8$ alkyl. In other embodiments, each $R_{23}$ can be $C_4$-$C_6$ alkyl. In still other embodiments, each $R_{23}$ can be H.

Alternatively, two $R_{23}$ can be taken together with the nitrogen to which they are attached to form a monocyclic N-linked heterocyclyl or a bicyclic N-linked heterocyclyl. Examples of monocyclic and bicyclic heterocyclyls are described herein, including those described with respect to $R_{15}$. In some embodiments, two $R_{23}$ can be taken together with the nitrogen to which they are attached to form a monocyclic N-linked heterocyclyl; and the remaining $R_{23}$ can be $C_1$-$C_{10}$ alkyl. The monocyclic N-linked heterocyclyl can be 5-membered or a 6-membered monocyclic N-linked heterocyclyl.

In other embodiments, two $R_{23}$ can be taken together with the nitrogen to which they are attached to form a bicyclic N-linked heterocyclyl; and the remaining $R_{23}$ can be $C_1$-$C_{10}$ alkyl. The bicyclic N-linked heterocyclyl can be a fused-bicyclic N-linked heterocyclyl, such as a bridged-bicyclic N-linked heterocyclyl. The size of the bicyclic N-linked heterocyclyl can vary. In some embodiments, the bicyclic N-linked heterocyclyl can be a 7- or 8-membered bicyclic N-linked heterocyclyl. In some embodiments, two $R_{23}$ can be taken together with the nitrogen to which they are attached to form a monocyclic N-linked heterocyclyl or a bicyclic N-linked heterocyclyl described herein, and the remaining $R_{23}$ can be methyl. Examples of N-linked heterocyclyls include:

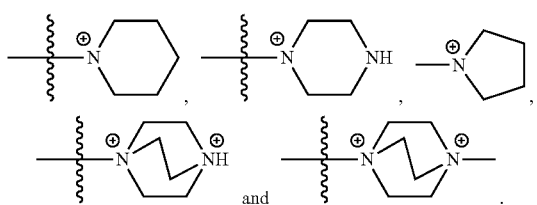

and

The monocyclic N-linked heterocyclyl and bicyclic N-linked heterocyclyls can be unsubstituted or substituted. When substituted, the non-hydrogen group can replace any hydrogen of the monocyclic and/or bicyclic N-linked heterocyclyls.

Further various $R_{23}$ group can be present and include hydroxyalkyl, aminoalkyl,

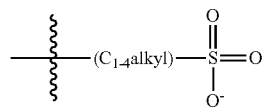

and —(($CH_2$)$_2$—O)$_{1-4}$—$CH_3$. In some embodiments, one or more $R_{23}$ groups can be hydroxyalkyl. As described herein, one or more hydroxy groups can be present on a hydroxyalkyl. In some embodiments, the hydroxyalkyl can be —(CH$_2$)$_4$—OH. In other embodiments, the hydroxyalkyl can be

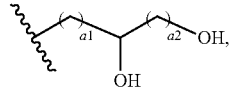

wherein a1 and a2 can be independently 1 or 2. In other embodiments, one or more R$_{23}$ groups can be aminoalkyl, such as a —(CH$_2$)$_{1-4}$—NH$_2$. In still other embodiments, one or more R$_{23}$ groups can be

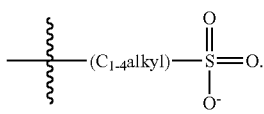

In yet still other embodiments, one or more R$_{23}$ groups can be —((CH$_2$)$_2$—O)$_1$—CH$_3$. For example, when an R$_{23}$ group is —((CH$_2$)$_2$—O)$_{1-4}$—CH$_3$, one or more R$_{23}$ groups can be

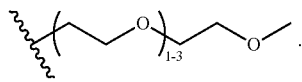

In some embodiments, one or more R$_{23}$ groups can be hydroxyalkyl, aminoalkyl,

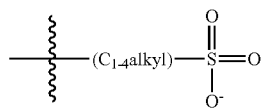

or —((CH$_2$)$_2$—O)$_{1-4}$—CH$_3$; and the remaining R$_{23}$ groups can be C$_1$-C$_{10}$ alkyl. In some embodiments, one R$_{23}$ group can be hydroxyalkyl, aminoalkyl,

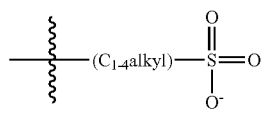

or —((CH$_2$)$_2$—O)$_{1-4}$—CH$_3$; and two R$_{23}$ groups can be independently C$_1$-C$_{10}$ alkyl. In other embodiments, two R$_{23}$ groups can be hydroxyalkyl, aminoalkyl,

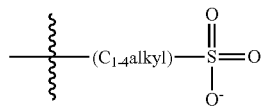

or —((CH$_2$)$_2$—O)$_{1-4}$—CH$_3$; and one R$_{23}$ group can be C$_1$-C$_{10}$ alkyl. In some embodiments, two R$_{23}$ groups can be hydroxyalkyl, aminoalkyl,

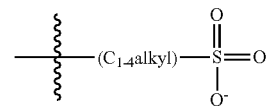

or —((CH$_2$)$_2$—O)$_{1-4}$—CH$_3$; and one R$_{23}$ group can be C$_4$-C$_6$ alkyl. In some embodiments, two R$_{23}$ groups can be hydroxyalkyl, aminoalkyl,

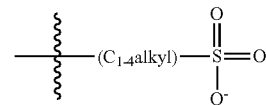

or —((CH$_2$)$_2$—O)$_{1-4}$—CH$_3$; and one R$_{23}$ group can be C$_1$-C$_4$ alkyl.

In some embodiments, each of R$_{19}$, R$_{20}$ and R$_{21}$ can be independently —O—R$_{24}$-R$_{25}$. The terminal R$_{25}$ group can be the various groups described herein, and include an unsubstituted or substituted N-linked pyridinyl, —(C$_2$-C$_3$ alkyl)N(R$_{26}$)$_3$ or —NH—(=NH)NH$_2$. In some embodiments, R$_{24}$ can be a C$_2$-C$_{10}$ alkyl as described in paragraph [0083] with respect to R$_{14}$. For example, R$_{24}$ can be —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$— or —(CH$_2$)$_{10}$—. In some embodiments, one or more of the hydrogens of the R$_{24}$ groups can be substituted with one or more —OH, —NH$_2$, —SO$_3^-$, C$_1$-C$_{20}$ alkyl, or —N(CH$_3$)$_2$R$_7$, wherein R$_{7c}$ can be C$_1$-C$_{20}$ alkyl.

In some embodiments, R$_{25}$ can be an unsubstituted N-linked pyridinyl. In other embodiments, R$_{25}$ can be a substituted N-linked pyridinyl. A variety of substituents can be present on a substituted N-linked pyridinyl, and include a substituent independently selected from an electron-donating group and electron-withdrawing group. In some embodiments, N-linked pyridinyl can be substituted with a substituent selected from a substituted or unsubstituted C$_1$-C$_{20}$ alkyl, C$_2$-C$_{20}$ alkenyl, C$_2$-C$_{20}$ alkynyl, aryl, alkoxy, amine, or thioether. The number of substituents present on a substituted N-linked pyridinyl can also vary. For example, the substituted N-linked pyridinyl can be substituted 1, 2, 3, or 4 times. In some embodiments, each of R$_{19}$, R$_{20}$ and R$_{21}$ can be —(C$_2$-C$_3$ alkyl)N(R$_{26}$)$_3$. For example, each of R$_{19}$, R$_{20}$ and R$_{21}$ can be —(CH$_2$)$_2$N(R$_{26}$)$_3$ or —(CH$_2$)$_3$N(R$_{26}$)$_3$.

The R$_{26}$ groups can vary as described herein. In some embodiments, each R$_{26}$ can be the same. In other embodiments, each R$_{26}$ can be different. In some embodiments, each R$_{26}$ can be independently C$_1$-C$_{10}$ alkyl. In some embodiments, each R$_{26}$ can be methyl. In other embodiments, each R$_{26}$ can be C$_2$-C$_{10}$ alkyl. In some embodiments, each R$_{26}$ can be C$_2$-C$_8$ alkyl. In other embodiments, each R$_{26}$ can be C$_4$-C$_6$ alkyl.

As described herein, x can be 0, 1 or 2. In some embodiments, when x is 0, the compound of Formula 6 can have the structure:

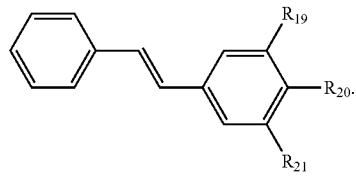

In other embodiments, when x is 1, the compound of Formula 6 can have the structure:

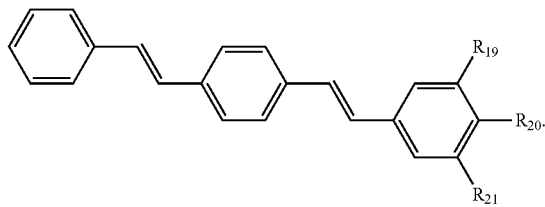

In still other embodiments, when x is 2, the compound of Formula 6 can have the structure:

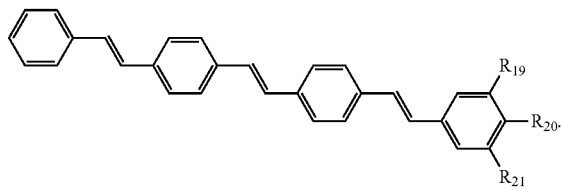

In some embodiments, when $R_{22}$ is $C_3$ alkyl, then $R_{24}$ cannot be methyl. In some embodiments, when one or more of $R_{19}$, $R_{20}$ and $R_{21}$ is —O—$R_{24}$-$R_{25}$, then $R_{25}$ cannot be an unsubstituted or substituted N-linked pyridinyl. In some embodiments, each $R_{24}$ cannot be methyl. In some embodiments, including those of this paragraph, $R_{22}$ cannot be $C_3$ alkyl. In some embodiments, including those of this paragraph, $R_{22}$ cannot be $C_6$ alkyl. In some embodiments, including those of this paragraph, $R_{24}$ cannot be $C_3$ alkyl. In some embodiments, including those of this paragraph, $R_{24}$ cannot be $C_6$ alkyl.

In other embodiments, the COEs have a structural Formula 7:

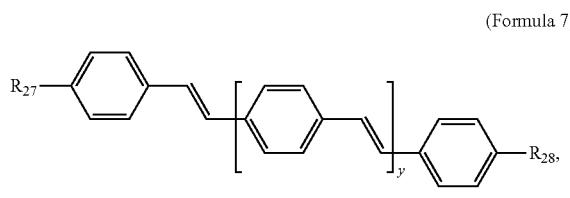

(Formula 7)

wherein $R_{27}$ and $R_{15}$ are independently —N—($R_{29}$)—N($R_{30}$)$_3$; $R_{29}$ is $C_2$-$C_{10}$ alkyl; each $R_{30}$ is independently H, $C_1$-$C_{10}$ alkyl, $C_1$-$C_{20}$ alkyl, $C_2$-$C_{20}$ alkenyl, $C_2$-$C_{20}$ alkynyl, aryl, hydroxyalkyl, aminoalkyl,

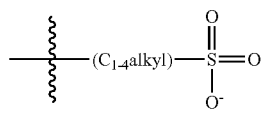

or —((CH$_2$)$_2$—O)$_{1-4}$—CH$_3$, or two $R_{30}$ are taken together with the nitrogen to which they are attached to form a monocyclic N-linked heterocyclyl or a bicyclic N-linked heterocyclyl; y is 1 or 2; and the counter ions include I$^-$, Br$^-$, Cl$^-$, F$^-$, organic anion, BIm$_4^-$ or B(ArF)$_4^-$.

In some embodiments, $R_{29}$ can be a $C_2$-$C_{10}$ alkyl as described in paragraph [0083] with respect to $R_{14}$. Various $R_{30}$ groups can be present on a COE of Formula 7. In some embodiments, each $R_{30}$ can be the same. In other embodiments, each $R_{30}$ can be different. In some embodiments, each $R_{30}$ can be independently $C_1$-$C_{10}$ alkyl. In some embodiments, each $R_{30}$ can be methyl. In other embodiments, each $R_{30}$ can be $C_2$-$C_{10}$ alkyl. In some embodiments, each $R_{30}$ can be $C_2$-$C_8$ alkyl. In other embodiments, each $R_{30}$ can be $C_4$-$C_6$ alkyl. In some embodiments, each $R_{30}$ can be H.

In some embodiments, $R_{30}$ can be $C_2$-$C_{20}$ alkenyl. In some embodiments, $R_{30}$ can be $C_2$-$C_{10}$ alkenyl. In some embodiments, $R_{30}$ can be $C_4$-$C_6$ alkenyl. In other embodiments, $R_3$ can be $C_2$-$C_{20}$ alkynyl, including, but not limited to, $C_2$-$C_{10}$ alkynyl or $C_4$-$C_6$ alkynyl. In still other embodiments, $R_{30}$ can be aryl, such as phenyl.

As described herein, two $R_{30}$ can be taken together with the nitrogen to which they are attached to form a monocyclic N-linked heterocyclyl or a bicyclic N-linked heterocyclyl. Examples of monocyclic and bicyclic heterocyclyls are described herein. In some embodiments, two $R_{30}$ can be taken together with the nitrogen to which they are attached to form a monocyclic N-linked heterocyclyl; and the remaining $R_{30}$ can be $C_1$-$C_{10}$ alkyl. The monocyclic N-linked heterocyclyl can be 5-membered or a 6-membered monocyclic N-linked heterocyclyl. In other embodiments, two $R_{30}$ can be taken together with the nitrogen to which they are attached to form a bicyclic N-linked heterocyclyl; and the remaining $R_{30}$ can be $C_1$-$C_{10}$ alkyl. The bicyclic N-linked heterocyclyl can be a fused-bicyclic N-linked heterocyclyl, such as a bridged-bicyclic N-linked heterocyclyl. The size of the bicyclic N-linked heterocyclyl can vary. In some embodiments, the bicyclic N-linked heterocyclyl can be a 7- or 8-membered bicyclic N-linked heterocyclyl. In some embodiments, two $R_{30}$ can be taken together with the nitrogen to which they are attached to form a monocyclic N-linked heterocyclyl or a bicyclic N-linked heterocyclyl described herein, and the remaining $R_{30}$ can be methyl. Examples of N-linked heterocyclyls include:

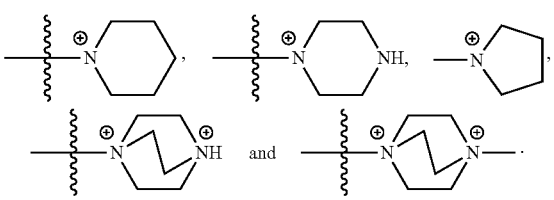

The monocyclic N-linked heterocyclyl and bicyclic N-linked heterocyclyls can be unsubstituted or substituted. When substituted, the non-hydrogen group can replace any hydrogen of the monocyclic and/or bicyclic N-linked heterocyclyls.

Further various $R_{30}$ group can be present and include hydroxyalkyl, aminoalkyl,

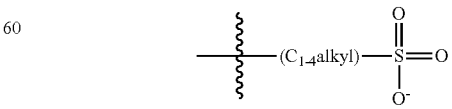

and —((CH$_2$)$_2$—O)$_{1-4}$—CH$_3$. In some embodiments, one or more $R_{30}$ groups can be hydroxyalkyl. As described herein, one or more hydroxy groups can be present on a hydroxyalkyl. In some embodiments, the hydroxyalkyl can be —$(CH_2)_{1-4}$—OH. In other embodiments, the hydroxyalkyl can be

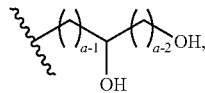

wherein a1 and a2 can be independently 1 or 2. In other embodiments, one or more $R_{30}$ groups can be aminoalkyl, such as a —$(CH_2)_{1-4}$—$NH_2$. In still other embodiments, one or more $R_{30}$ groups can be

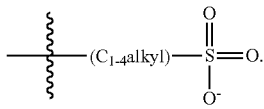

In yet still other embodiments, one or more $R_{30}$ groups can be —$((CH_2)_2$—O$)_{1-4}$—$CH_3$. For example, when an $R_{30}$ group is —$((CH_2)_2$—O$)_{1-4}$—$CH_3$, one or more $R_{23}$ groups can be

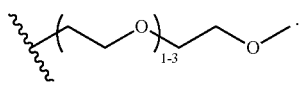

In some embodiments, one or more $R_{30}$ groups can be hydroxyalkyl, aminoalkyl,

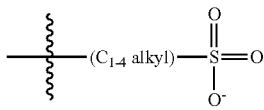

or —$((CH_2)_2$—O$)_{1-4}$—$CH_3$; and the remaining $R_{30}$ groups can be $C_1$-$C_{10}$ alkyl. In some embodiments, one $R_{30}$ group can be hydroxyalkyl, aminoalkyl,

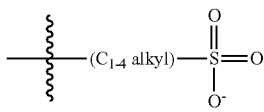

or —$((CH_2)_2$—O$)_{1-4}$—$CH_3$; and two $R_{23}$ groups can be independently $C_1$-$C_{10}$ alkyl. In other embodiments, two $R_{23}$ groups can be hydroxyalkyl, aminoalkyl,

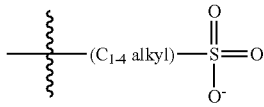

or —$((CH_2)_2$—O$)_{1-4}$—$CH_3$; and one $R_{30}$ group can be $C_1$-$C_{10}$ alkyl. In some embodiments, two $R_{23}$ groups can be hydroxyalkyl, aminoalkyl,

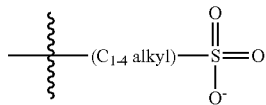

or —$((CH_2)_2$—O$)_{1-4}$—$CH_3$; and one $R_{30}$ group can be $C_4$-$C_6$ alkyl. In some embodiments, two $R_{30}$ groups can be hydroxyalkyl, aminoalkyl,

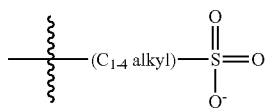

or —$((CH_2)_2$—O$)_{1-4}$—$CH_3$; and one $R_{30}$ group can be $C_1$-$C_4$ alkyl.

In some embodiments, y can be 1. In other embodiments, y can be 2.

In some embodiments, $R_{29}$ cannot be $C_6$ alkyl. In some embodiments, each $R_{30}$ cannot be methyl. In some embodiments, two $R_{30}$ cannot be taken together with the nitrogen to which they are attached to form a monocyclic N-linked heterocyclyl, such as morpholinyl. In some embodiments, y cannot be 1. In other embodiments, y cannot be 2. In some embodiments, including those of this paragraph, $R_{29}$ cannot be $C_3$ alkyl. In some embodiments, including those of this paragraph, $R_{29}$ cannot be $C_6$ alkyl. In some embodiments, a COE of Formula 7 cannot be Formula VV. In some embodiments, a compound described herein cannot be a compound of Formula 7.

Further formulae that described compounds herein are provided below in the section entitled "Further Formulae." For each of the following formulae, each variable pertains only to this section entitled "Further Formulae."

Further Formulae

In some embodiments, a compound is provided having the structure of Formula (I):

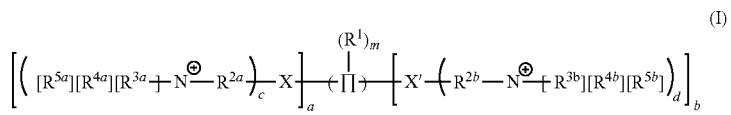

or a pharmaceutically acceptable isomer, racemate, hydrate, solvate, isotope, or salt thereof, wherein:

$\Pi$ is a $\Pi_n^k$ pi conjugated system wherein n is the number of conjugated centers and k is the number of electrons in the pi conjugated system;

n is 3-40;

k is 3-40;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —S(O)$_2$—, —N—, —NC(O)—, —C(O)N—, or a bond;

$N^\oplus$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^3$ and an adjacent $R^{4a}$ and $R^{5b}$, at each occurrence, independently, or one $R^{3b}$ and an adjacent $R^{4b}$ and $R^{5b}$, at each occurrence, independently, together with the atoms to which they are attached, form an 8-14 membered fused or bridged heterocycle;

wherein $R^{3a}$, $R^{3b}$, $R^{4a}$, $R^{4b}$, $R^{5a}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl;

a is 0-5;

b is 1-5;

c is 1-2; and d is 1-2.

In some embodiments, a can be 0 and b can be 1-5. In another embodiment, a can be 1-5 and b can be 1-5.

In some embodiments, Π can be a pi conjugated system comprising $π_p$, wherein π is a repeating pi conjugation structure and p is 0-10. In some embodiments, p can be 0-5. In another embodiment, p can be 0, 1, 2, or 3.

In some embodiments, a compound is provided having the structure of Formula or a pharmaceutically acceptable isomer, racemate, hydrate, solvate, isotope, or salt thereof, wherein:

π is a repeating pi conjugation structure;

p is 0-10; and ring A and ring A' are each, independently, optionally substituted aryl or optionally substituted heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —S(O)$_2$—, —N—, —NC(O)—, —C(O)N—, or a bond;

$N^\oplus$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or at least one $R^{3a}$, and an adjacent $R^1$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl;

a is 1-5;

b is 1-5;

c is 1-2; and d is 1-2.

In some embodiments, a compound is provided having the structure of Formula (II-A):

$$\left[\left([R^{5a}][R^{4a}][R^{3a}]{-}N^\oplus{-}R^{2a}\right)_c{-}X\right]_a \quad \underset{A}{\overset{(R^1)_m}{\bigcirc}}{-}(\pi)_p{-}\underset{A'}{\bigcirc} \quad \left[X'{-}\left(R^{2b}{-}N^\oplus{-}[R^{3b}][R^{4b}][R^{5b}]\right)_d\right]_b \quad (II)$$

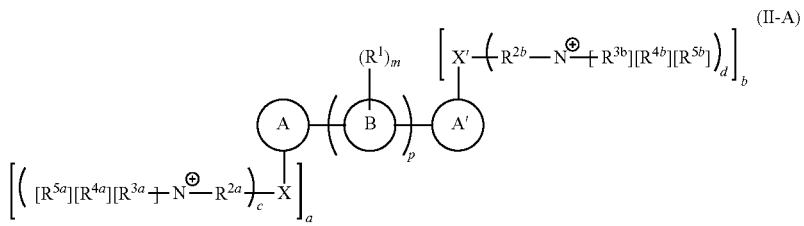

(II-A)

or a pharmaceutically acceptable isomer, racemate, hydrate, solvate, isotope, or salt thereof, wherein:

p is 0-10; and ring A and ring A' are each, independently, optionally substituted aryl or optionally substituted heteroaryl;

ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —S(O)$_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein $R^7$ is $C_1$-$C_{20}$ alkyl;

a is 1-5;

b is 1-5;

c is 1-2; and d is 1-2.

In some embodiments, a compound is provided having the structure of Formula (II-B):

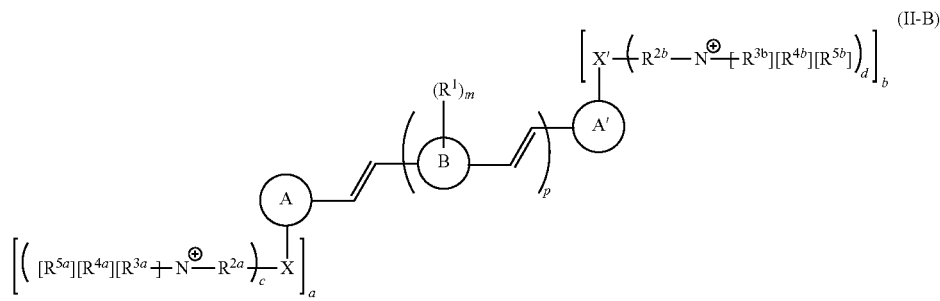

(II-B)

or a pharmaceutically acceptable isomer, racemate, hydrate, solvate, isotope, or salt thereof, wherein:

p is 0-10; and ring A and ring A' are each, independently, optionally substituted aryl or optionally substituted heteroaryl;

ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —S(O)$_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^3$ and an adjacent $R^{4a}$ and $R^{5a}$, at each occurrence, independently, or one $R^{3b}$ and an adjacent $R^b$ and R, at each occurrence, independently, together with the atoms to which they are attached, form an 8-14 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl;

a is 1-5;
b is 1-5;
c is 1-2; and
d is 1-2.

In some embodiments, a compound is provided having the structure of Formula (II-C):

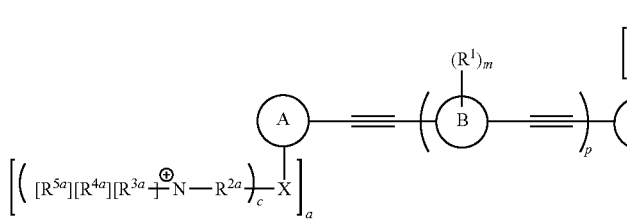

(II-C)

or a pharmaceutically acceptable isomer, racemate, hydrate, solvate, isotope, or salt thereof, wherein:

p is 0-10; and ring A and ring A' are each, independently, optionally substituted aryl or optionally substituted heteroaryl;

ring B is aryl or heteroaryl;

m is 0-12;

R$^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —S(O)$_2$—, —N—, —NC(O)—, —C(O)N—, or a bond;

N$^⊕$ represents an ammonium, quaternary ammonium, imidazolium, or pyrrolidinium cationic group;

R$^{2a}$ and R$^{2b}$ are, independently, and at each occurrence, $C_1$-$C_{20}$ alkylene, arylene, or a bond;

R$^{3a}$ and R$^{3b}$ are at each occurrence, independently, H, $C_1$-$C_{20}$ alkyl, $C_2$-$C_{20}$ alkenyl, $C_2$-$C_{20}$ alkynyl, or aryl;

R$^{4a}$ and R$^{4b}$ are at each occurrence, independently, H, $C_1$-$C_{20}$ alkyl, $C_2$-$C_{20}$ alkenyl, $C_2$-$C_{20}$ alkynyl, or aryl;

R$^{5a}$ and R$^{5b}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or at least one R$^{3a}$, and an adjacent R$^{4a}$, at each occurrence, or at least one R$^{3b}$ and an adjacent R$^{4b}$, at each occurrence, together with the N to which they are attached, form a 5-8 membered monocyclic heterocycle;

or at least one R$^{3a}$ and an adjacent R$^{4a}$ and R$^{5a}$, at each occurrence, independently, or one R$^{3b}$ and an adjacent R$^{4b}$ and R$^{5b}$, at each occurrence, independently, together with the atoms to which they are attached, form an 8-14 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl;

a is 1-5;
b is 1-5;
c is 1-2; and
d is 1-2.

In some embodiments, a compound is provided having the structure of Formula (II):

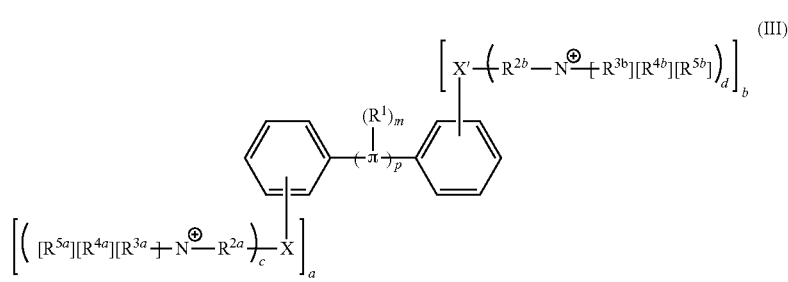

(III)

or a pharmaceutically acceptable isomer, racemate, hydrate, solvate, isotope, or salt thereof, wherein:

π is a repeating pi conjugation structure;
p is 0-10; and
m is 0-12;

R$^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —S(O)$_2$—, —N—, —NC(O)—, —C(O)N—, or a bond;

N$^⊕$ represents an ammonium, quaternary ammonium, imidazolium, or pyrrolidinium cationic group;

R$^{2a}$ and R$^{2b}$ are, independently, and at each occurrence, $C_1$-$C_{20}$ alkylene, arylene, or a bond;

R$^{3a}$ and R$^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or at least one $R^a$, and an adjacent $R^1$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl;

a is 1-5;
b is 1-5;
c is 1-2; and
d is 1-2.

In some embodiments, a compound is provided having the structure of Formula (III-A):

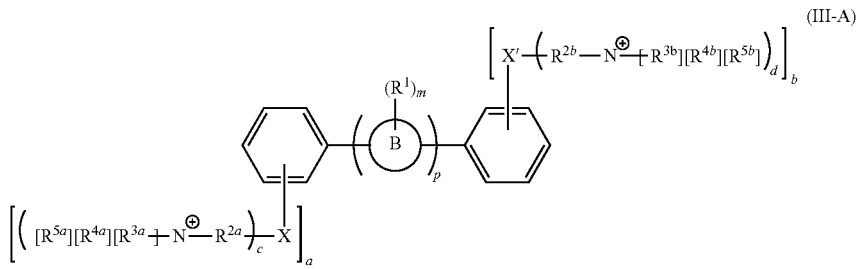

(III-A)

or a pharmaceutically acceptable isomer, racemate, hydrate, solvate, isotope, or salt thereof, wherein:
p is 0-10; and
ring B is aryl or heteroaryl;
m is 0-12;
$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;
X and X' are, independently, and at each occurrence, —O—, —S—, —C(O)—, —C(O)O—, —OC(O)—, —S(O)—, —S(O)$_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^3$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered bicyclic heterocycle;

wherein $R^{3a}$, $R^{3b}$, $R^{4a}$, R, $R^{5a}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl;

a is 1-5;
b is 1-5;
c is 1-2; and
d is 1-2.

In some embodiments, a compound is provided having the structure of Formula (III-B):

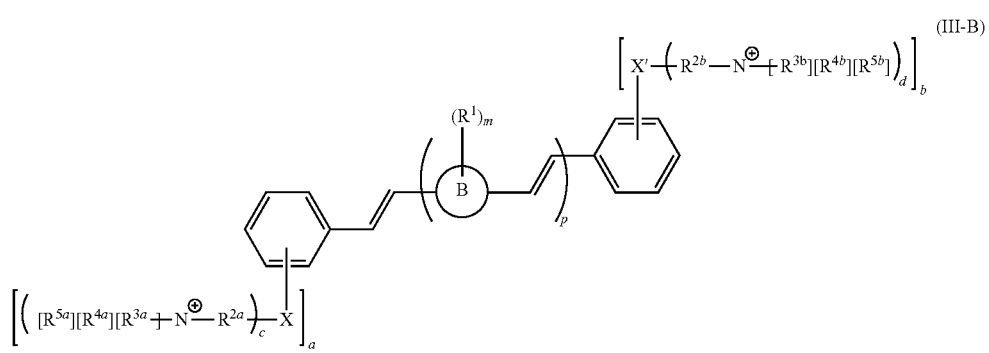

(III-B)

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —S(O)$_2$—, —N—, —NC(O)—, —C(O)N—, or a bond; $N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{5a}$ and $R^{5b}$, at each occurrence, independently, together with the atoms to which they are attached, form an 8-14 membered bicyclic heterocycle; wherein $R^{3a}$, $R^{3b}$, $R^{4a}$, $R^{4b}$, $R^{5a}$, or $R^{5b}$ are each, independently, optionally substituted with one or more —OH, —NH$_2$, —S(O)$_2$OH, $C_1$-$C_2$ alkyl, or —N$^+$(CH$_3$)$_2$R$^7$, wherein $R^7$ is $C_1$-$C_{20}$ alkyl;

a is 1-5;

b is 1-5;

c is 1-2; and d is 1-2.

In some embodiments, a compound is provided having the structure of Formula (III-C):

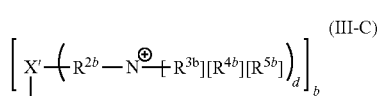

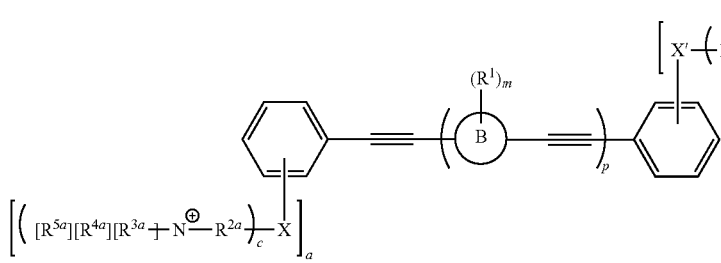

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —S(O)$_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^3$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered bicyclic heterocycle; wherein $R^{3a}$, $R^{3b}$, $R^{4a}$, $R^{4b}$, $R^{5a}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein $R^7$ is $C_1$-$C_{20}$ alkyl;

a is 1-5;

b is 1-5;

c is 1-2; and d is 1-2.

In some embodiments, c at each occurrence can be 1; d at each occurrence can be 1; and X and X' are, at each occurrence, can be 0.

In some embodiments, a compound is provided wherein a and b are each 2 and having the structure of Formula (IV):

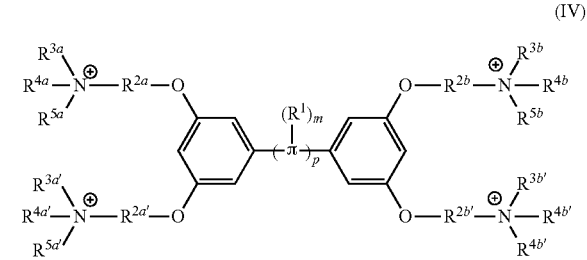

or a pharmaceutically acceptable isomer, racemate, hydrate, solvate, isotope, or salt thereof, wherein:

π is a repeating pi conjugation structure;

p is 0-10; and m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

$N^⊕$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, a compound is provided having the structure of Formula (IV-A):

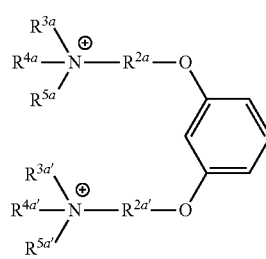

(IV-A)

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

$N^⊕$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^3$, $R^{3'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^4$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, a compound is provided having the structure of Formula (IV-B):

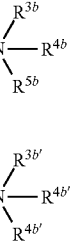

(IV-B)

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

$N^⊕$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, a compound is provided having the structure of Formula (IV-C):

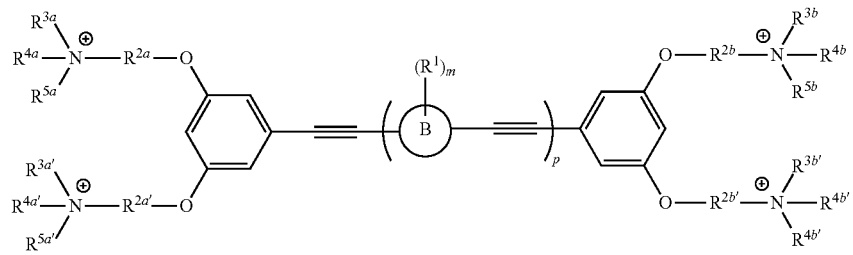

(IV-C)

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

N$^⊕$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, c at each occurrence can be 2; d at each occurrence can be 2; and X and X' are, at each occurrence, can be N.

In some embodiments, a compound is provided having the structure of Formula (V):

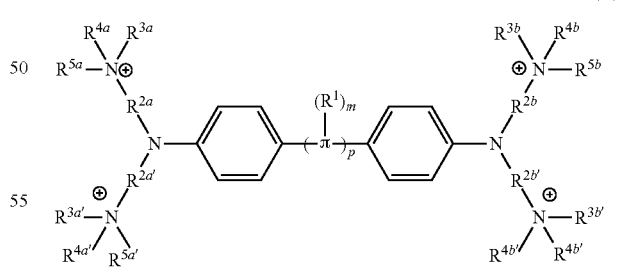

(V)

or a pharmaceutically acceptable isomer, racemate, hydrate, solvate, isotope, or salt thereof, wherein:

π is are repeating pi conjugation structure;

p is 0-10; and m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

N⊕ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_2$ alkenyl, $C_2$-$C_2$ alkynyl, or aryl; and $R^{5a}$, $R^{5a'}$, $R^{5b}$, and $R^{5b'}$ are at each occurrence, independently, $C_2$-$C_2$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, formula 5-8 membered monocyclic heterocycle;

or $R^3$ and $R^4$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, a compound is provided having the structure of Formula (V-A):

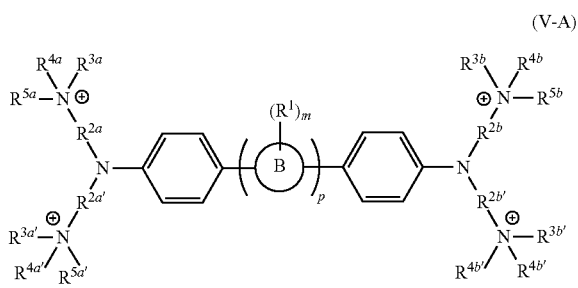

(V-A)

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

N⊕ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$s and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, a compound is provided having the structure of Formula (V-B):

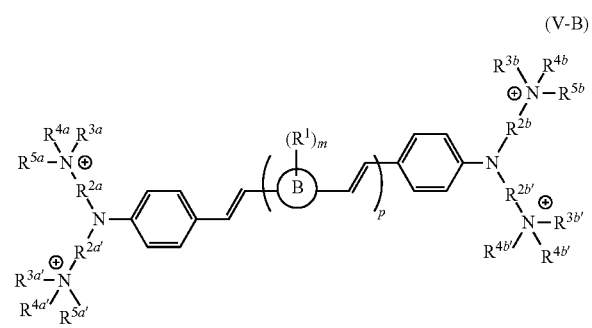

(V-B)

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

N⊕ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, a compound is provided having the structure of Formula (V-C):

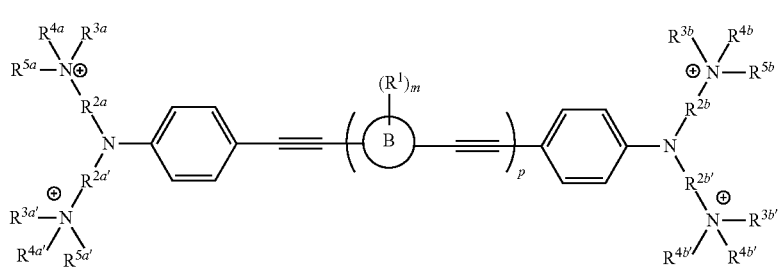

(V-C)

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

$N^\oplus$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH_2), or —(CH_2CH_2O)_z$R^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH_2, —S(O)_2OH, $C_1$-$C_{20}$ alkyl, or —N$^+$(CH_3)_2$R^7$, wherein $R^7$ is $C_1$-$C_{20}$ alkyl.

In some embodiments, ring B can be:

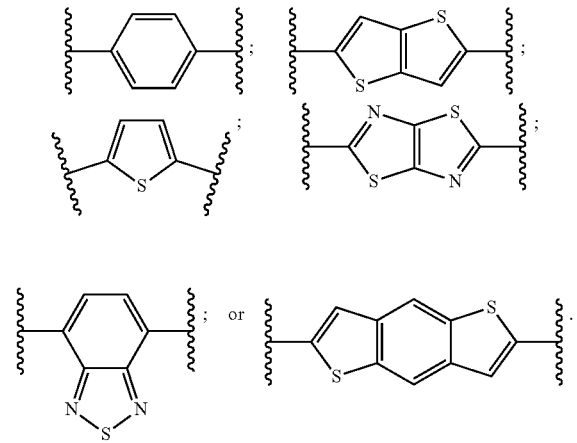

In some embodiments, a compound is provided wherein p is 0 and having the structure of Formula (IV-B-1):

(IV-B-1)

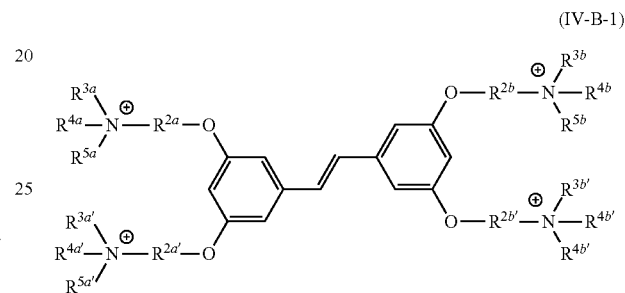

or a pharmaceutically acceptable isomer, racemate, hydrate, solvate, isotope, or salt thereof, wherein:

$N^\oplus$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^3$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^4$, $R^{4a'}$, $R^{4b}$, and $R^{4a'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH_2), or —(CH_2CH_2O)_z$R^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH_2, —S(O)_2OH, $C_1$-$C_{20}$ alkyl, or —N$^+$(CH_3)_2$R^7$, wherein $R^7$ is $C_1$-$C_{20}$ alkyl.

In some embodiments, a compound is provided wherein p is 1 and having the structure of Formula (IV-B-2):

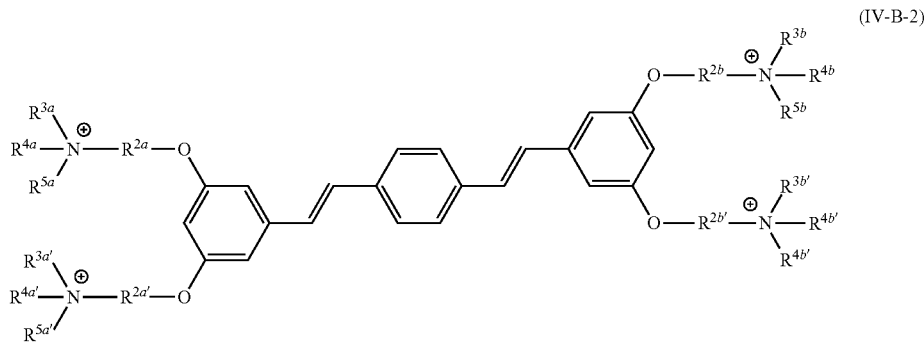

(IV-B-2)

or a pharmaceutically acceptable isomer, racemate, hydrate, solvate, isotope, or salt thereof, wherein:

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, a compound is provided wherein p is 2 and having the structure of Formula (IV-B-3):

or a pharmaceutically acceptable isomer, racemate, hydrate, solvate, isotope, or salt thereof, wherein:

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, a compound is provided wherein p is 0 and having the structure of Formula (V-B-1):

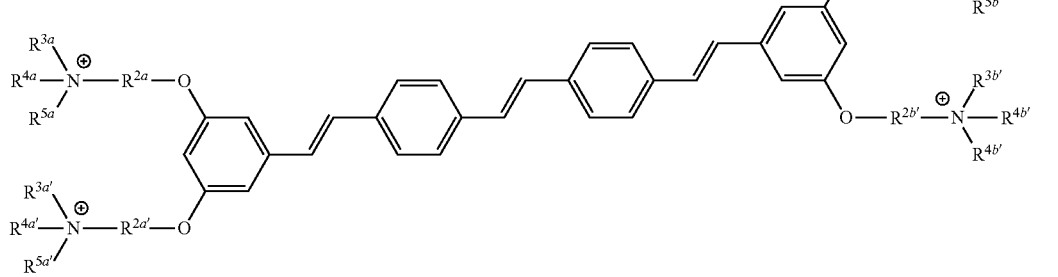

(IV-B-3)

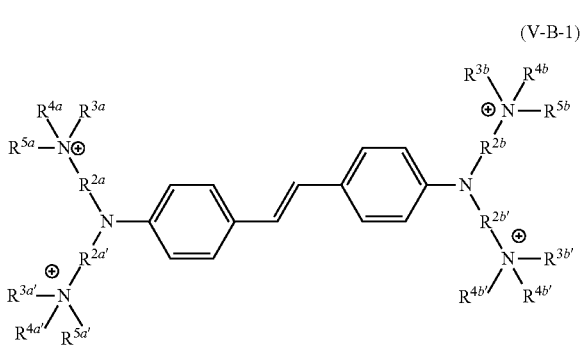

(V-B-1)

or a pharmaceutically acceptable isomer, racemate, hydrate, solvate, isotope, or salt thereof, wherein:

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, a compound is provided wherein p is 1 and having the structure of Formula (V-B-2):

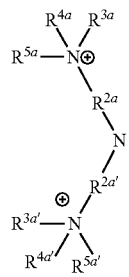

(V-B-2)

or a pharmaceutically acceptable isomer, racemate, hydrate, solvate, isotope, or salt thereof, wherein:

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^3$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, a compound is provided wherein p is 2 and having the structure of Formula (V-B-3):

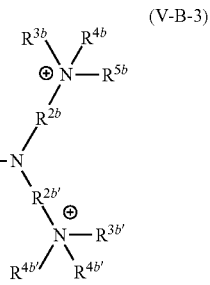
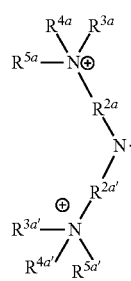

(V-B-3)

or a pharmaceutically acceptable isomer, racemate, hydrate, solvate, isotope, or salt thereof, wherein:

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)(NH$_2$), or —(CH$_2$CH$_2$O)$_z$R$^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and R, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —NH$_2$, —S(O)$_2$OH, $C_1$-$C_{20}$ alkyl, or —N$^+$(CH$_3$)$_2$R$^7$, wherein R$^7$ is $C_1$-$C_{20}$ alkyl.

In some embodiments, $R^{5a}$ and $R^{5b}$ can be at each occurrence, independently, $C_2$-$C_{20}$ alkyl. In some embodiments, $R^{5a}$ and $R^{5b}$ can be at each occurrence, independently, —(CH$_2$CH$_2$O)$_z$R$^7$ where z is 1-6, wherein R$^7$ can be $C_1$-$C_{20}$ alkyl. In some embodiments, $R^{3a}$ and $R^{4a}$, and $R^{3b}$ and $R^{4b}$, independently, together with the N to which they are independently attached, can form a 5-8 membered monocyclic heterocycle. In some embodiments, $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, can form an 8-14 membered bicyclic heterocycle.

Specific Compounds

Exemplary COEs have a structure of any of Formulae A-H and J-XX:

Formula A

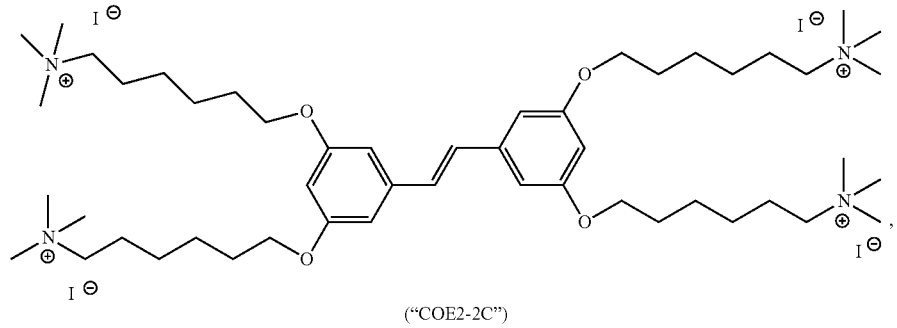

("COE2-2C")

Formula B
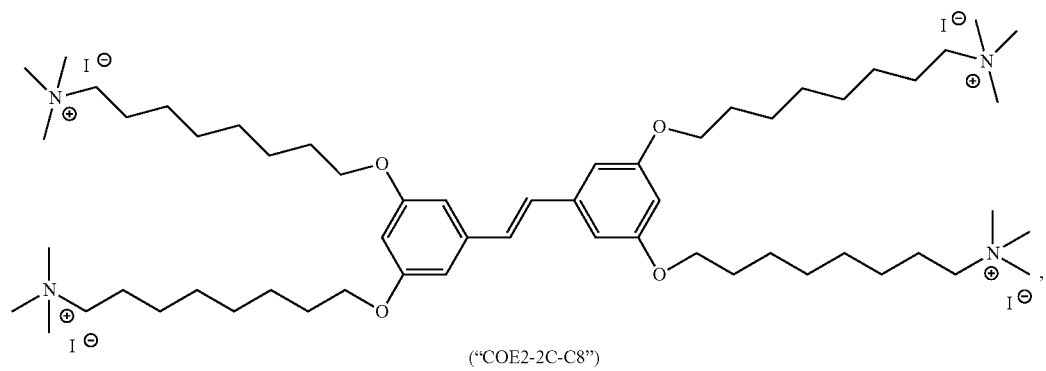
("COE2-2C-C8")
Formula C
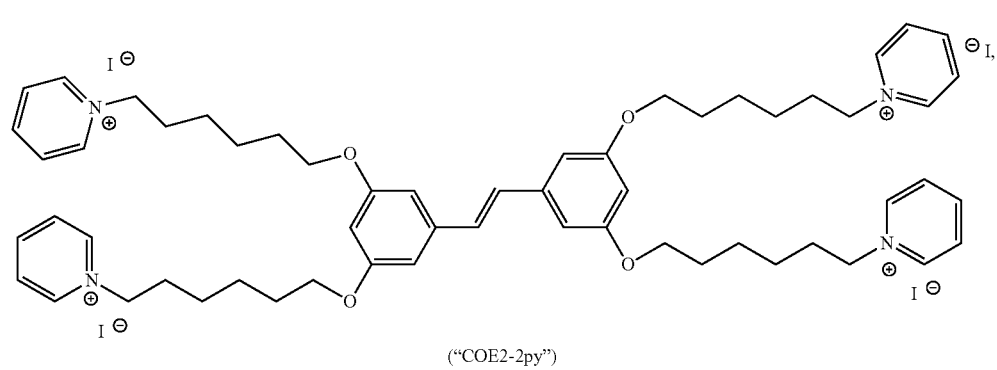
("COE2-2py")
Formula D
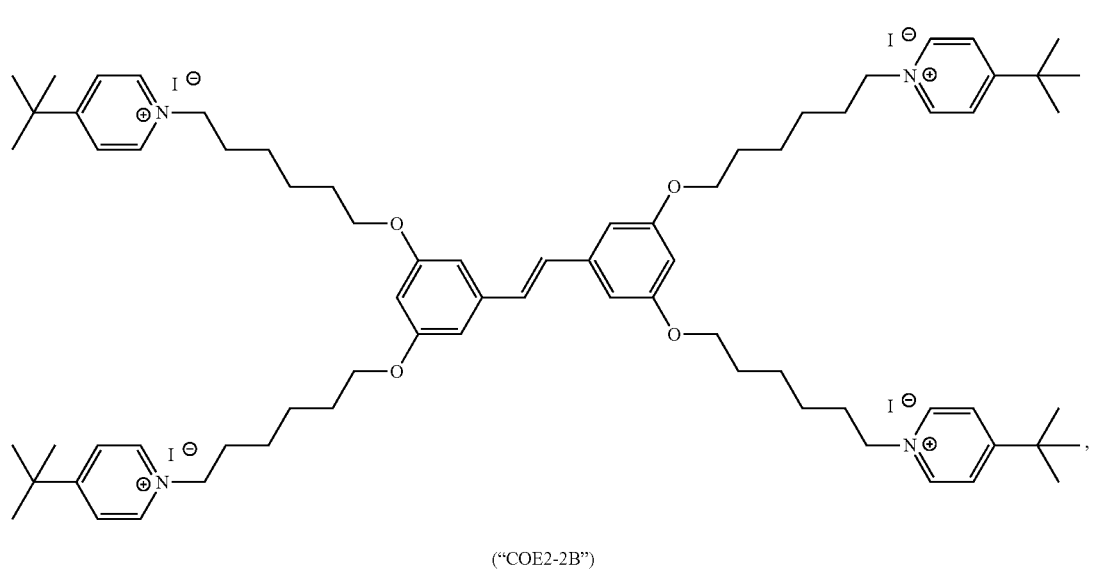
("COE2-2B")
Formula E
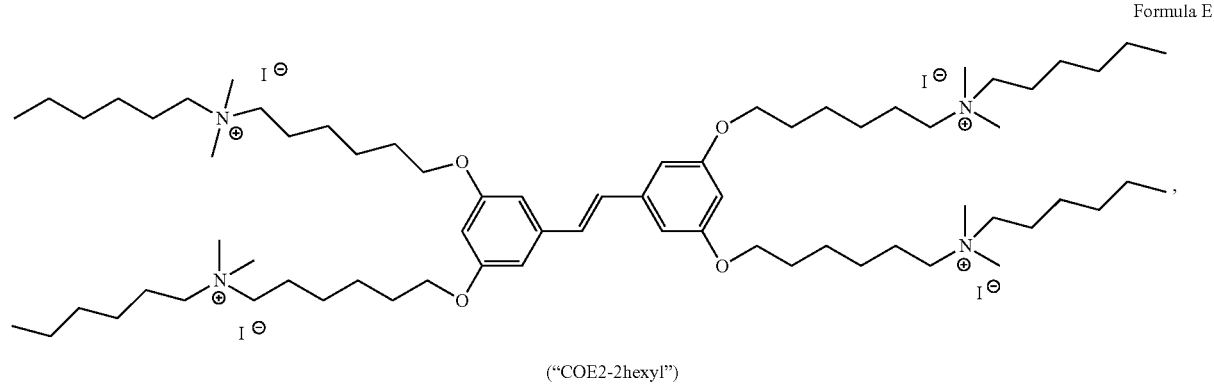
("COE2-2hexyl")

-continued
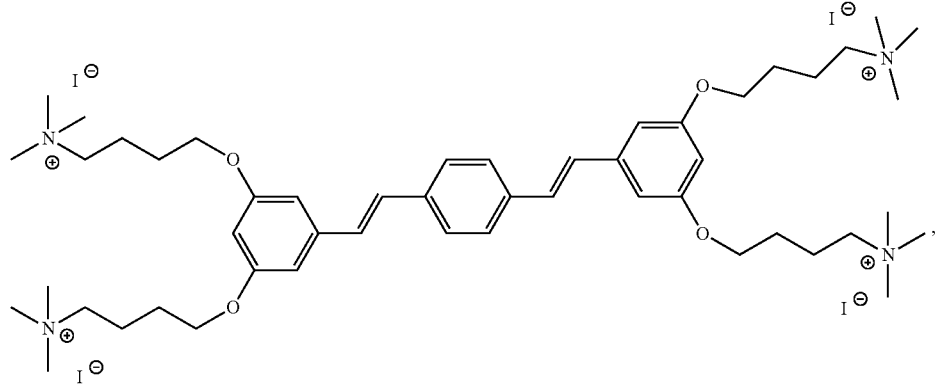
("COE2-3C-C4")
Formula F
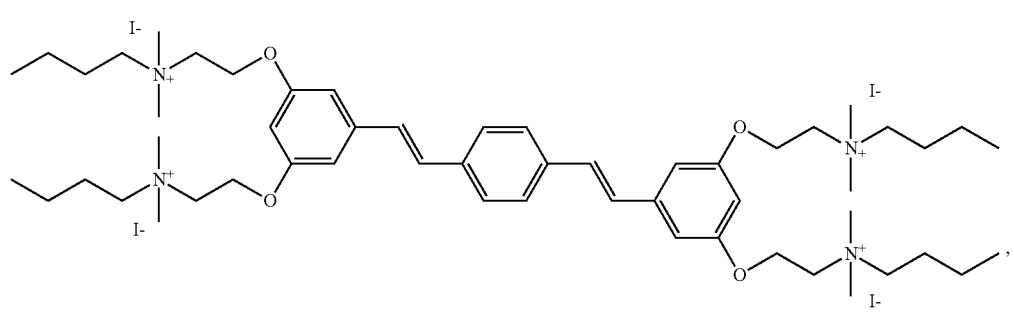
("COE2-3C-C2butyl")
Formula G
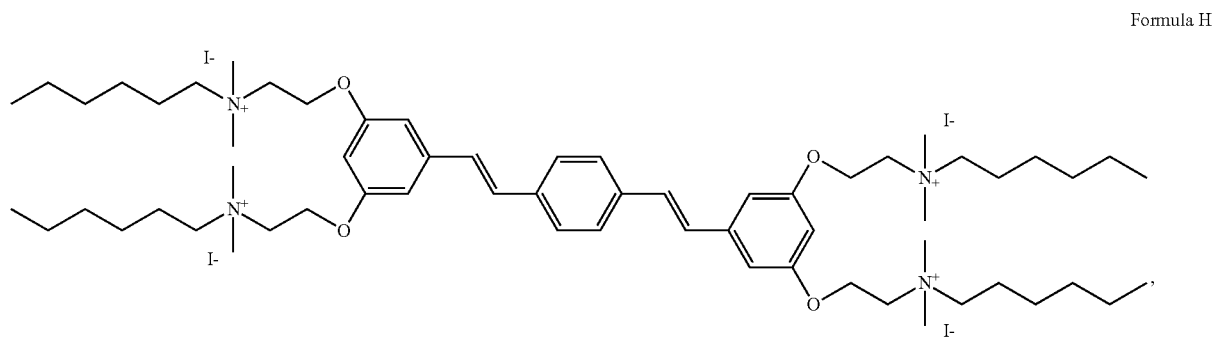
("COE2-3C-C2hexyl")
Formula H
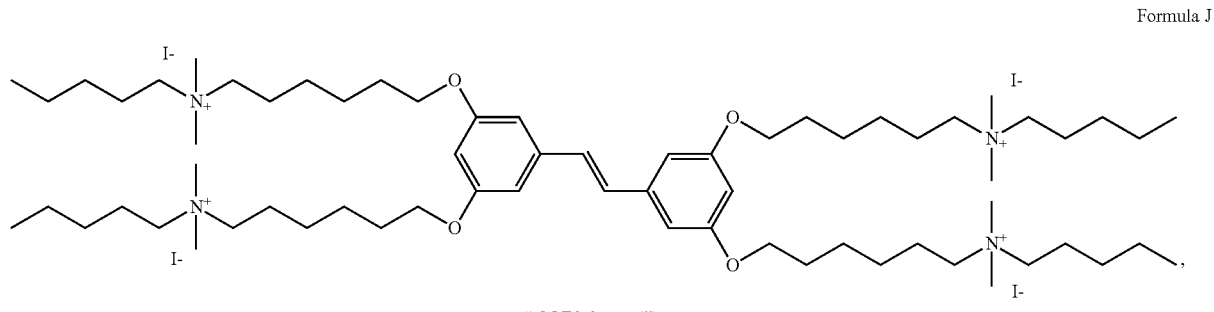
("COE2-2pentyl")
Formula J -continued
Formula K
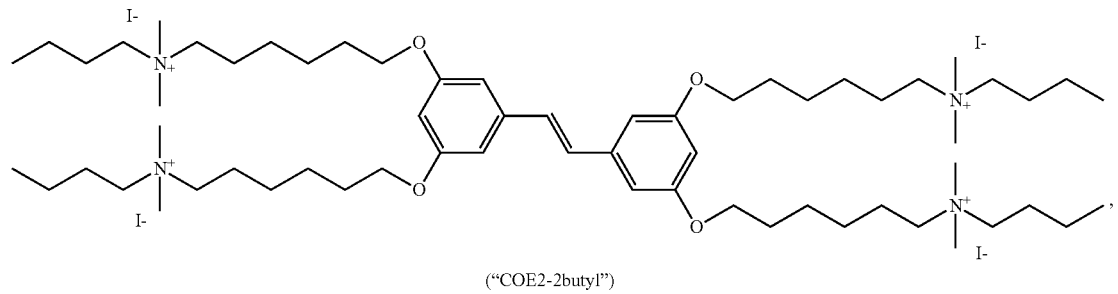
("COE2-2butyl")
Formula L
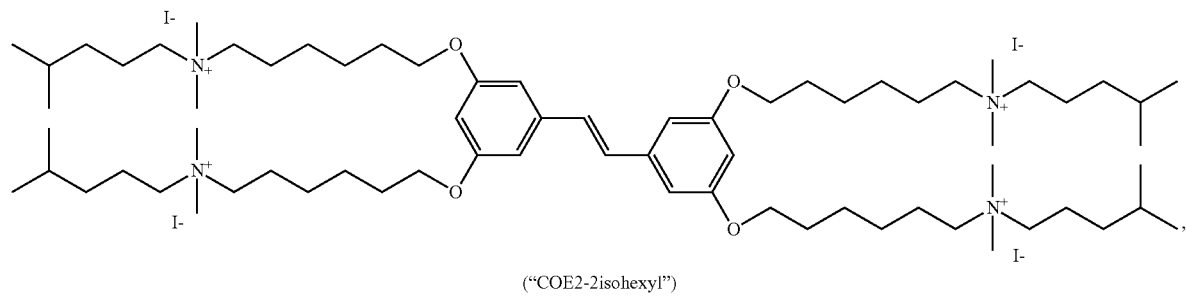
("COE2-2isohexyl")
Formula M
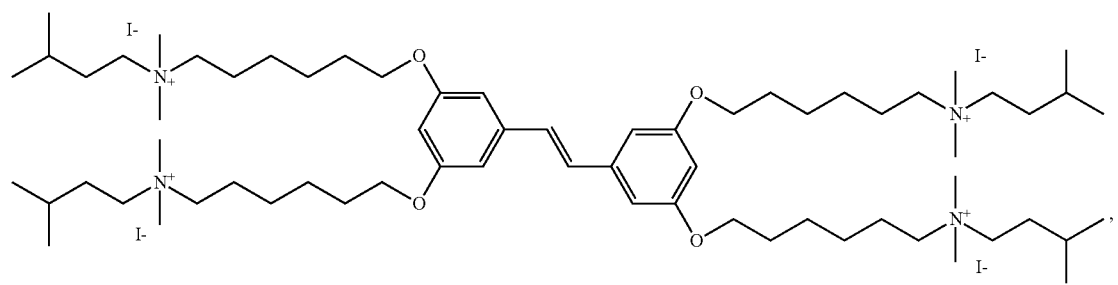
("COE2-2isopentyl")
Formula N
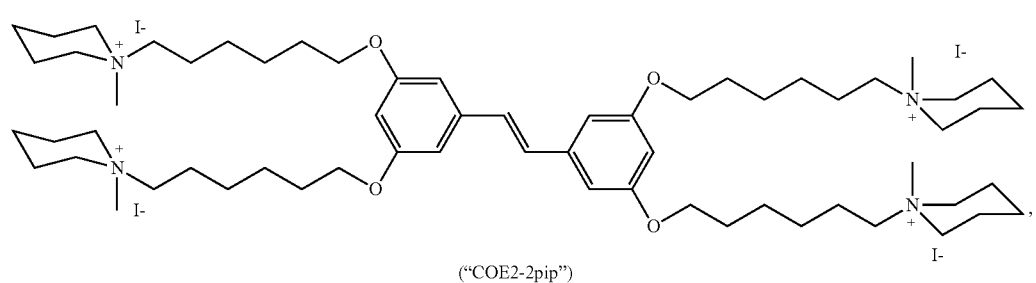
("COE2-2pip")
Formula O
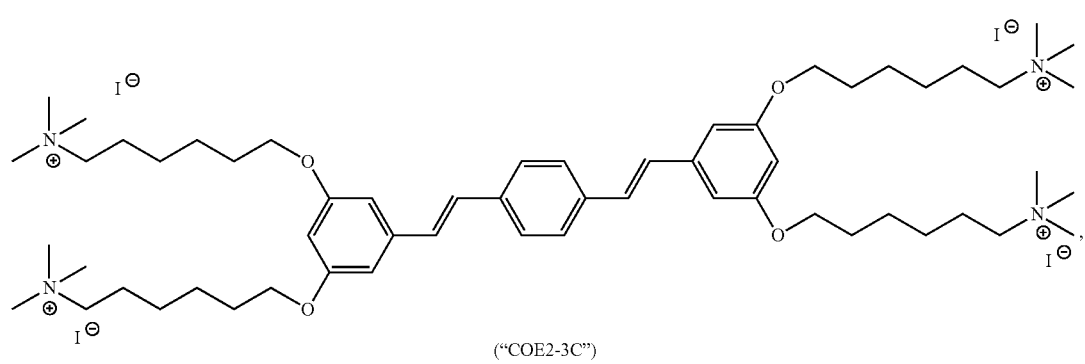
("COE2-3C")

-continued
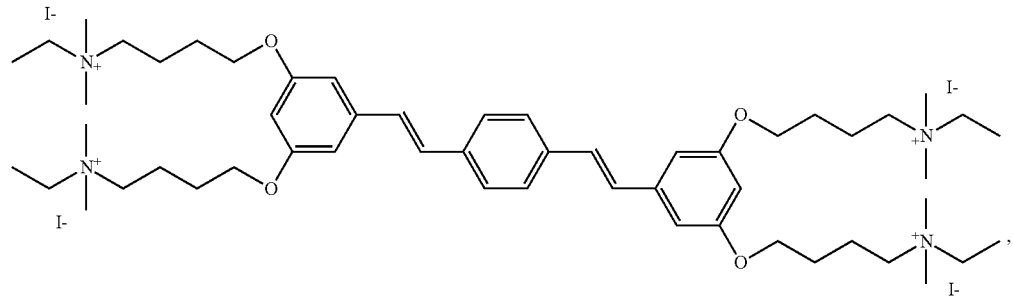
("COE2-3C-C4ethyl") Formula P
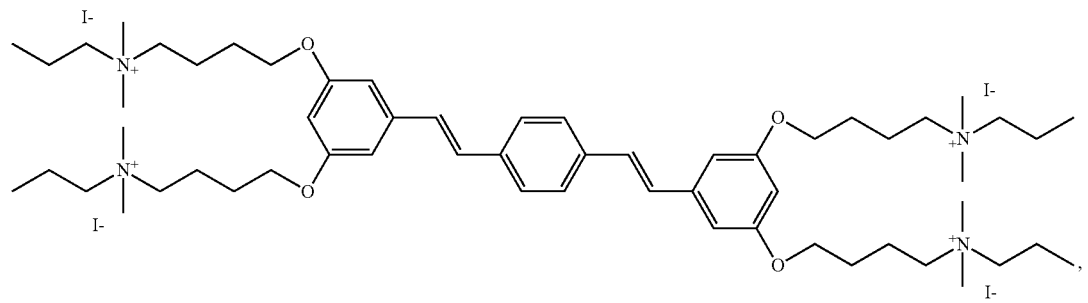
("COE2-3C-C4propyl") Formula Q
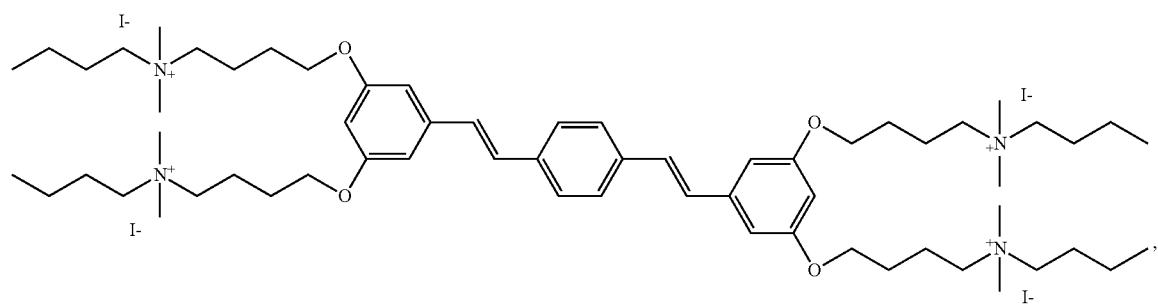
("COE2-3C-C4butyl") Formula R
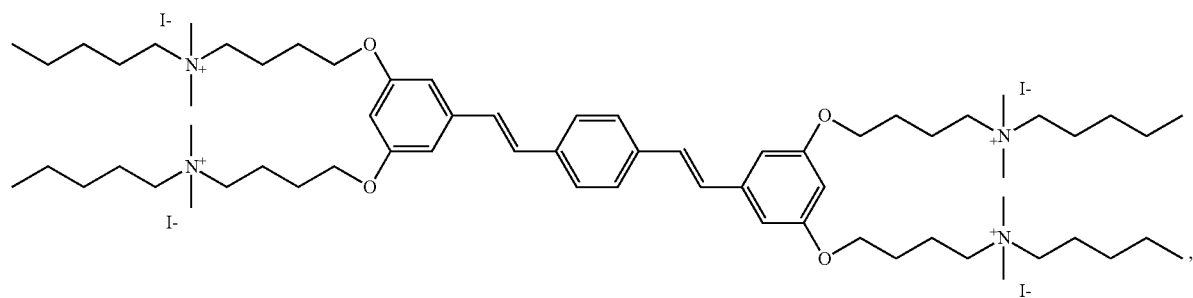
("COE2-3C-C4pentyl") Formula S -continued
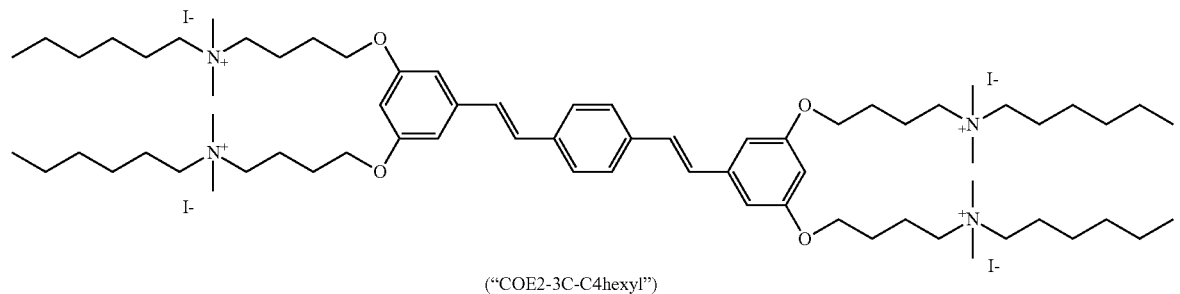
("COE2-3C-C4hexyl")
Formula T
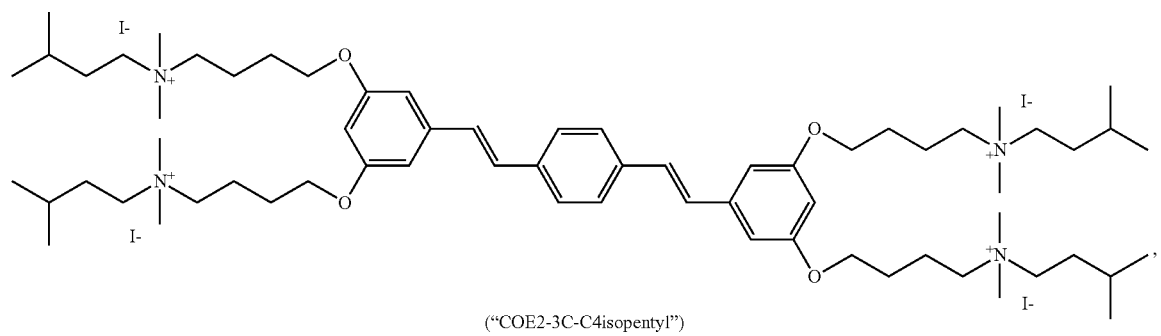
("COE2-3C-C4isopentyl")
Formula U
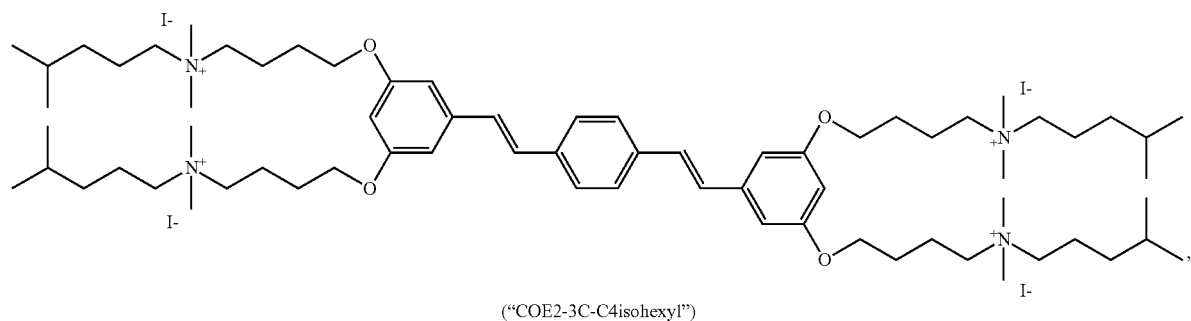
("COE2-3C-C4isohexyl")
Formula V
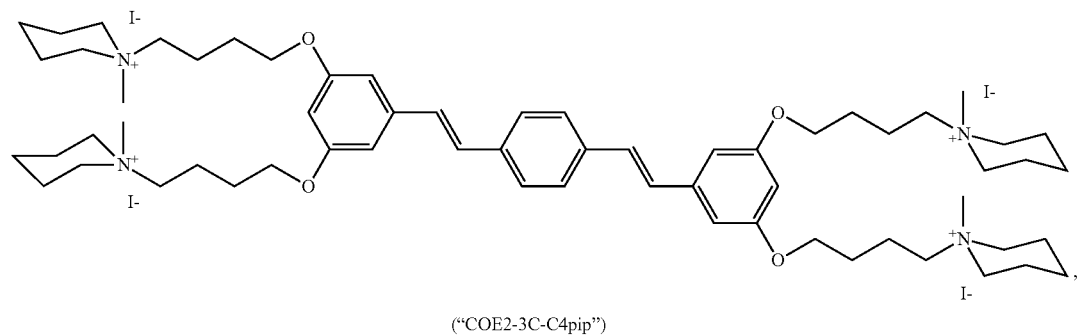
("COE2-3C-C4pip")
Formula W Formula X
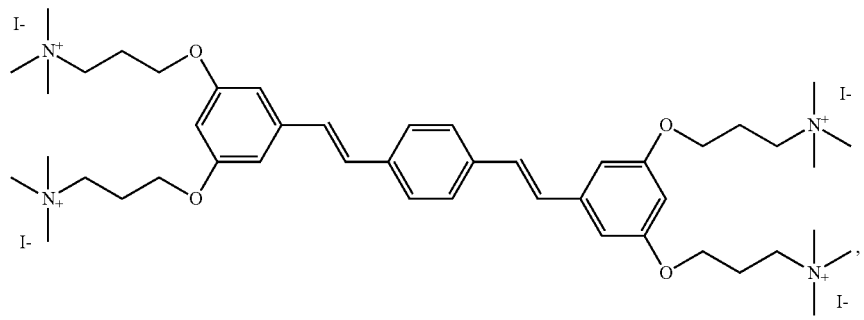
("COE2-3C-C3")
Formula Y
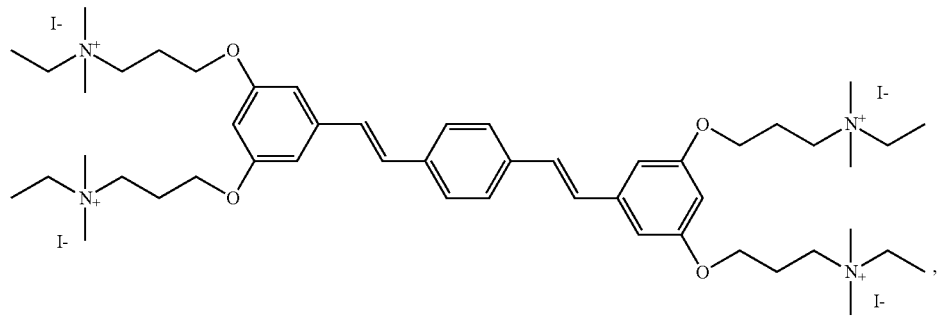
("COE2-3C-C3ethyl")
Formula Z
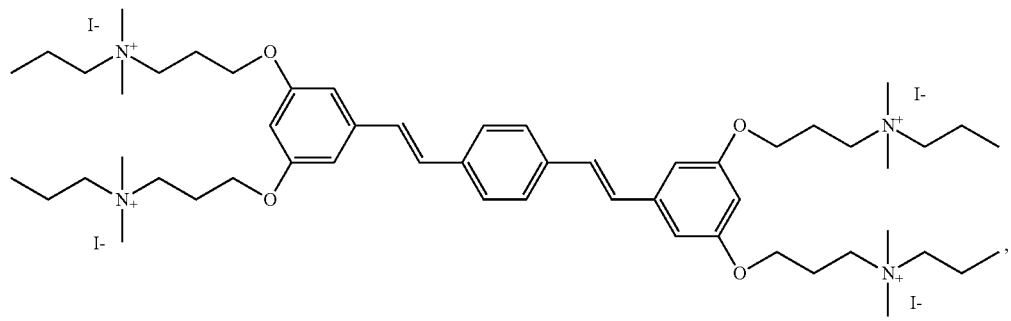
("COE2-3C-C3propyl")
Formula AA
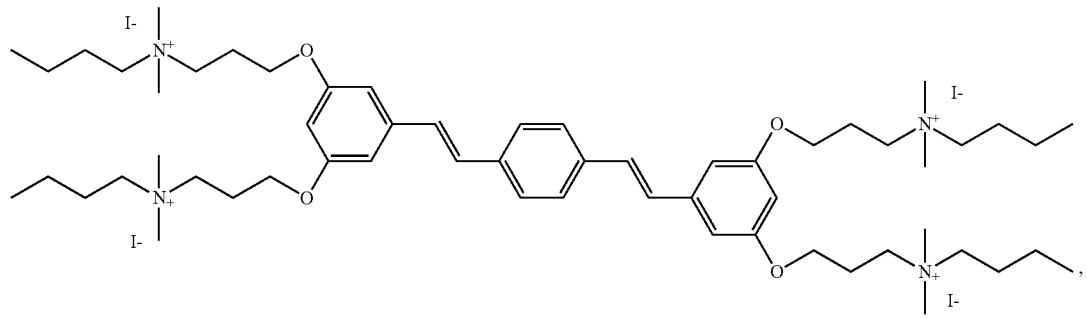
("COE2-3C-C3butyl")

-continued
Formula BB
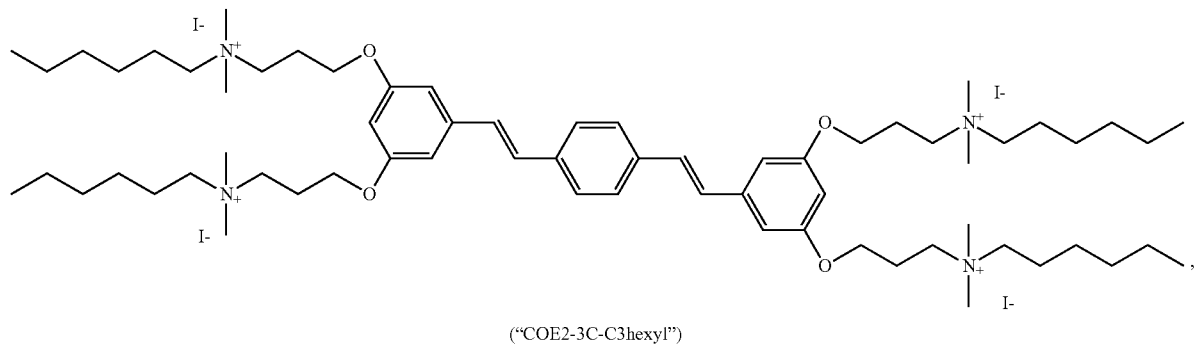
("COE2-3C-C3hexyl")
Formula CC
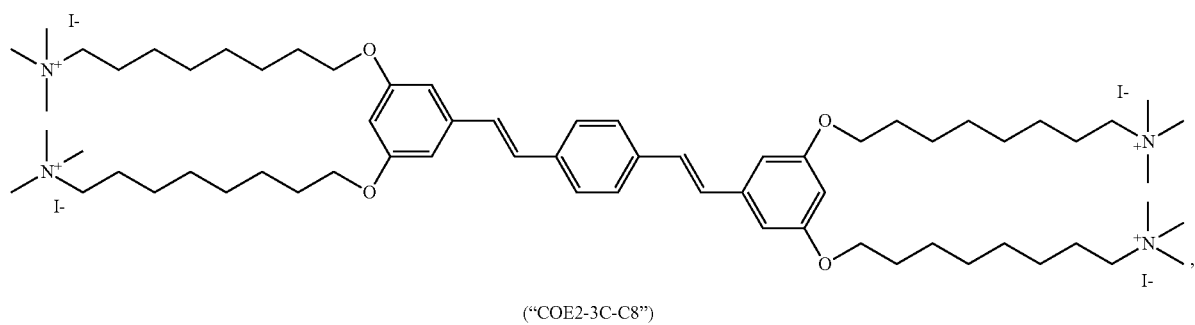
("COE2-3C-C8")
Formula DD
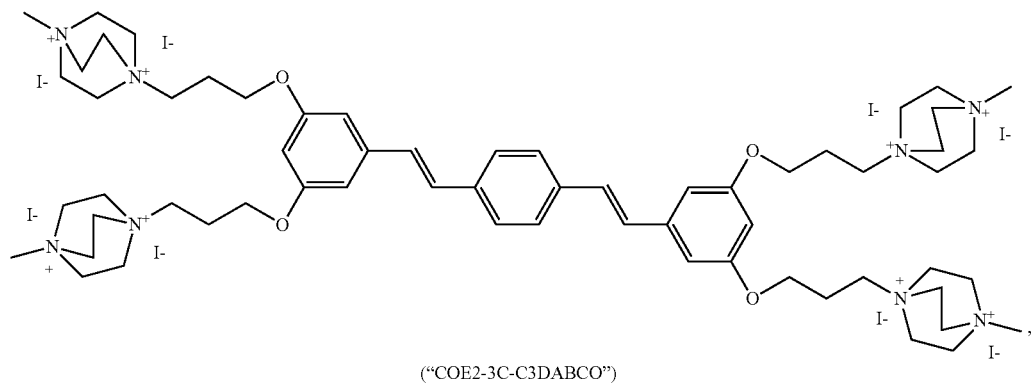
("COE2-3C-C3DABCO")
Formula EE
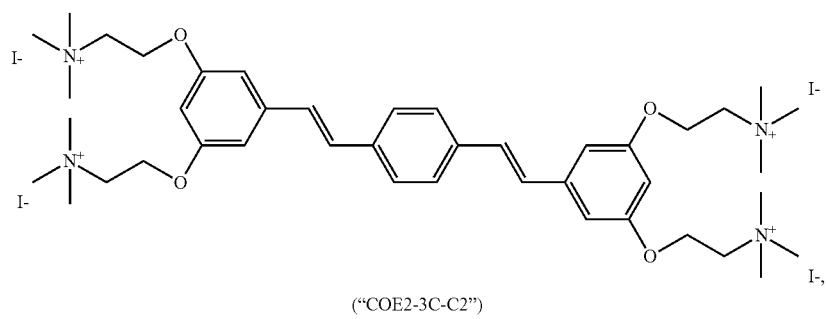
("COE2-3C-C2")

-continued
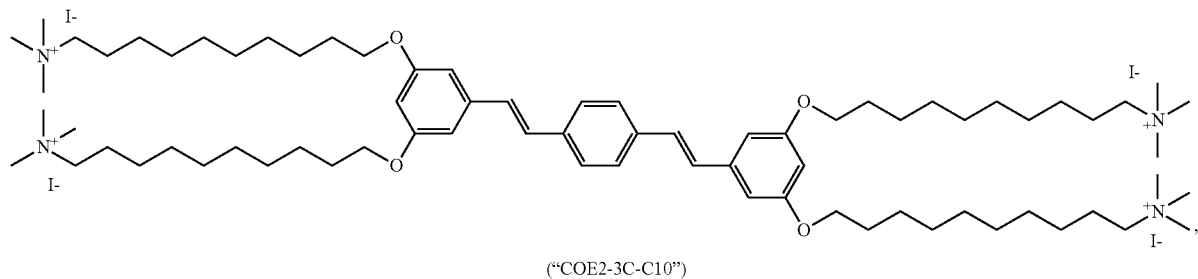
Formula FF
("COE2-3C-C10")
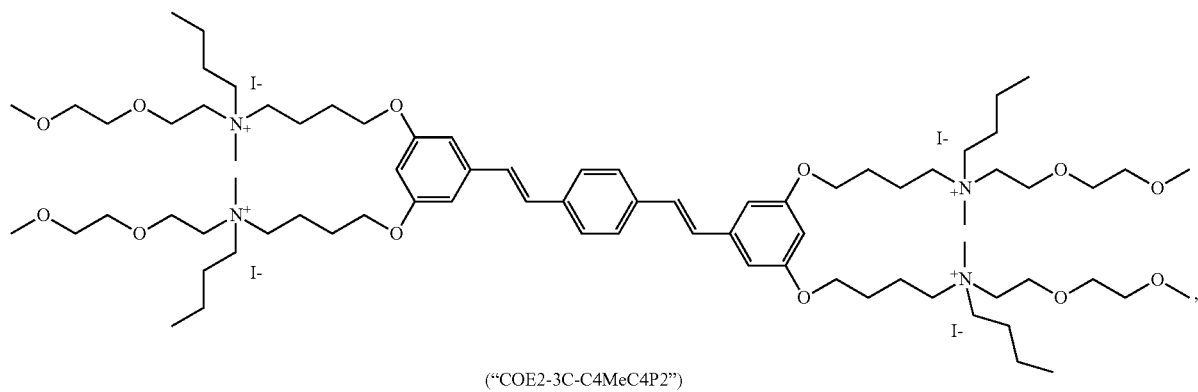
Formula GG
("COE2-3C-C4MeC4P2")
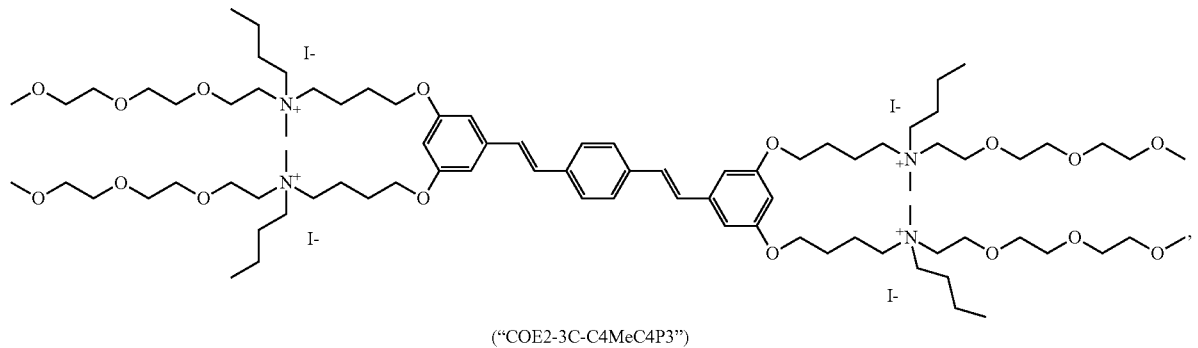
Formula HH
("COE2-3C-C4MeC4P3")
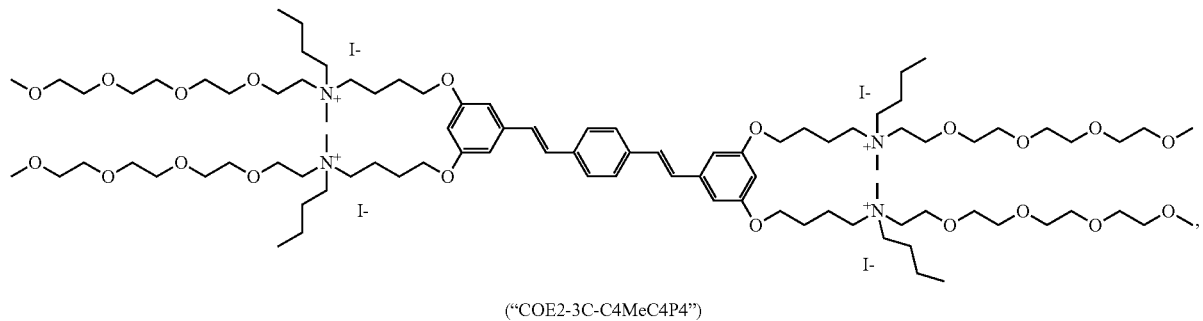
Formula II
("COE2-3C-C4MeC4P4")

-continued
Formula JJ
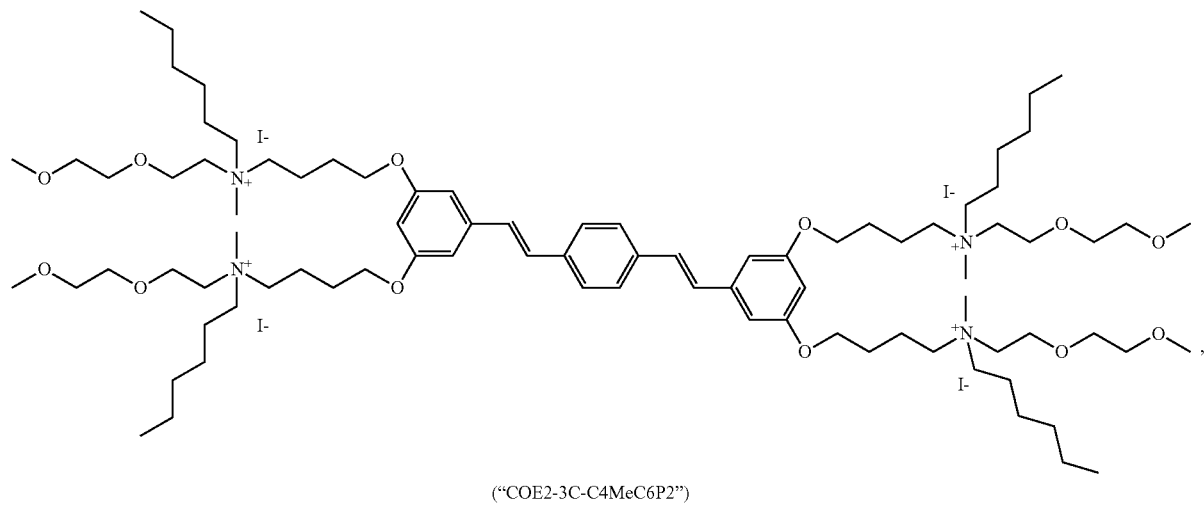
("COE2-3C-C4MeC6P2")
Formula KK
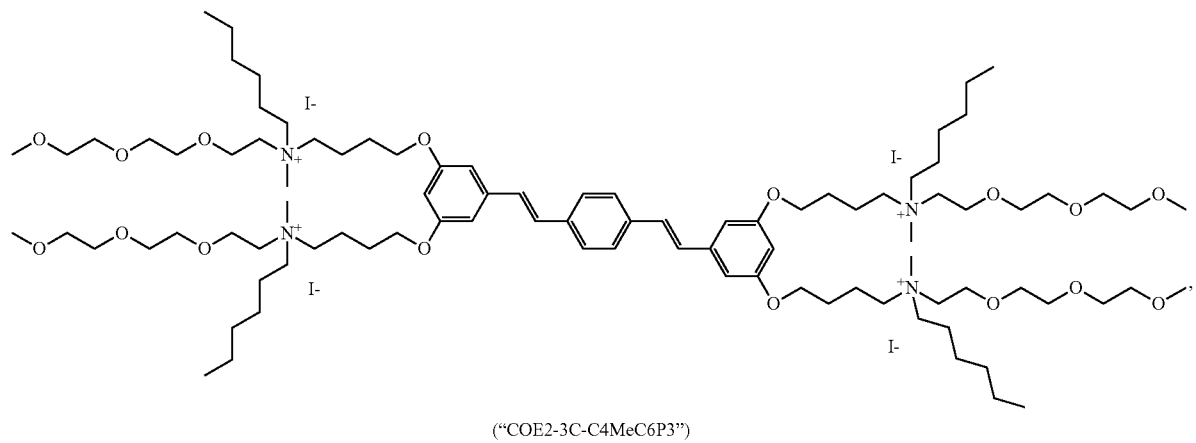
("COE2-3C-C4MeC6P3")
Formula LL
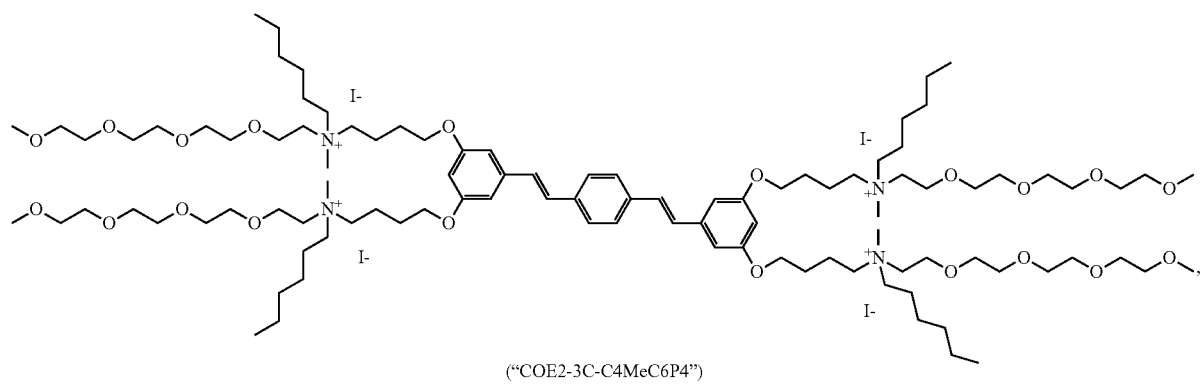
("COE2-3C-C4MeC6P4")

-continued
Formula MM
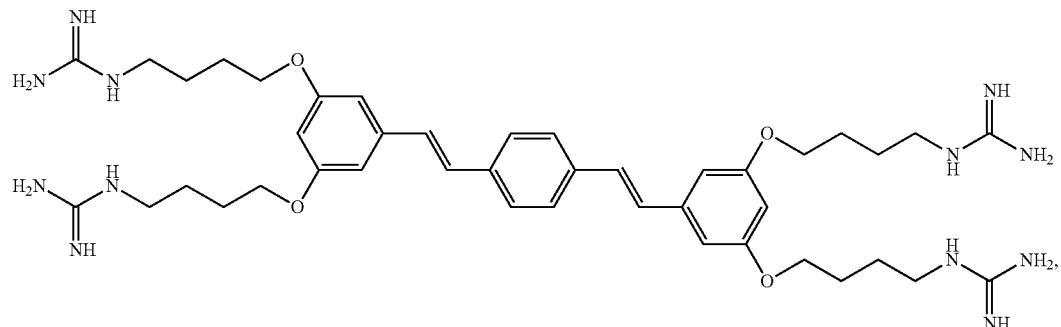
("COE 2-3C-C4guanidine")
Formula NN
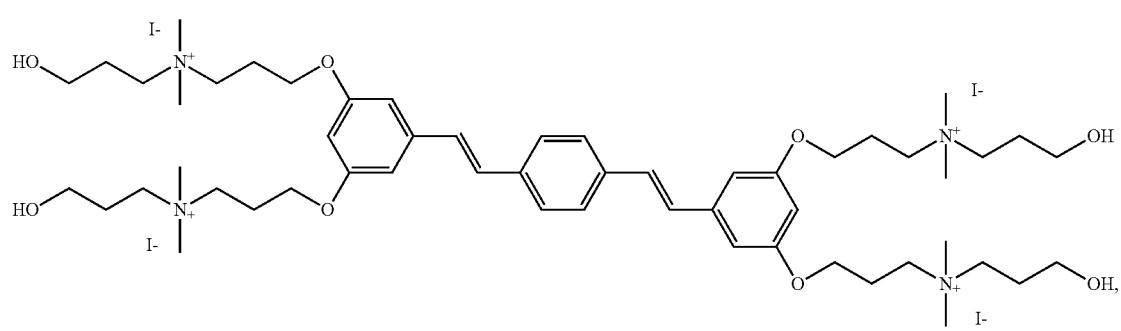
("COE2-3C-C3propyl-OH")
Formula OO
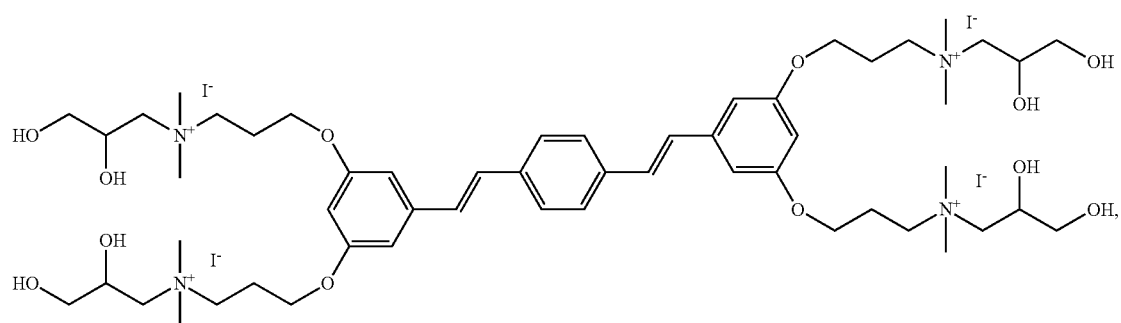
("COE2-3C-C3glycerol")
Formula PP
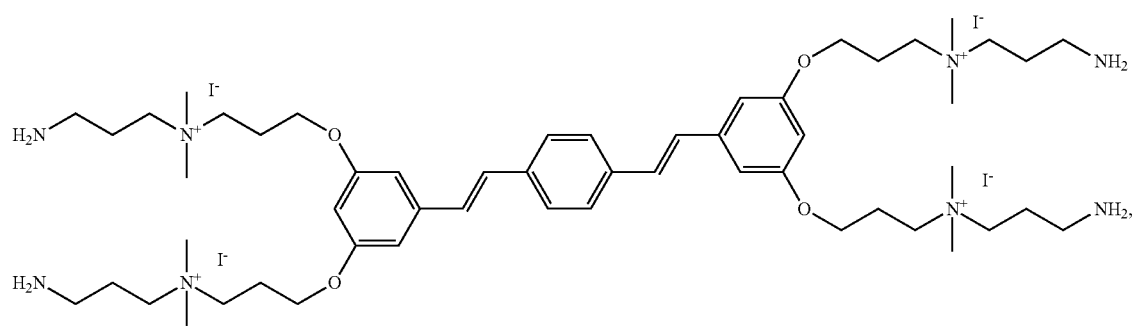
("COE2-3C-C3propyl-NH2")

-continued
Formula QQ
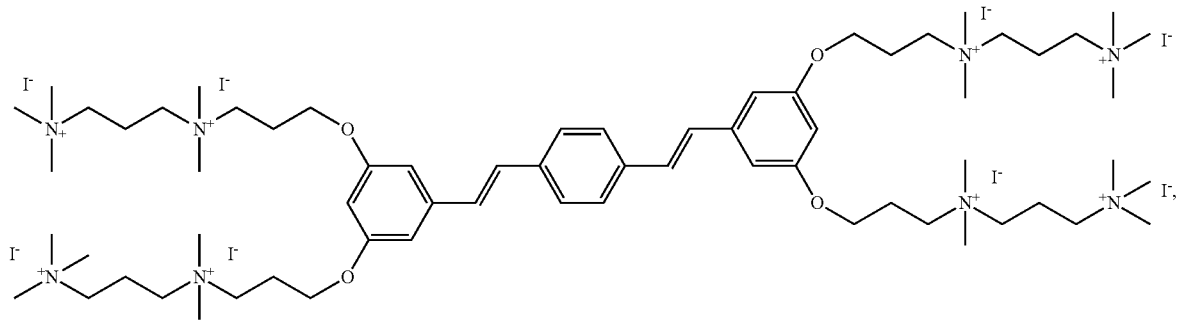
("COE2-3C-C3propyl-NMe3")
Formula RR
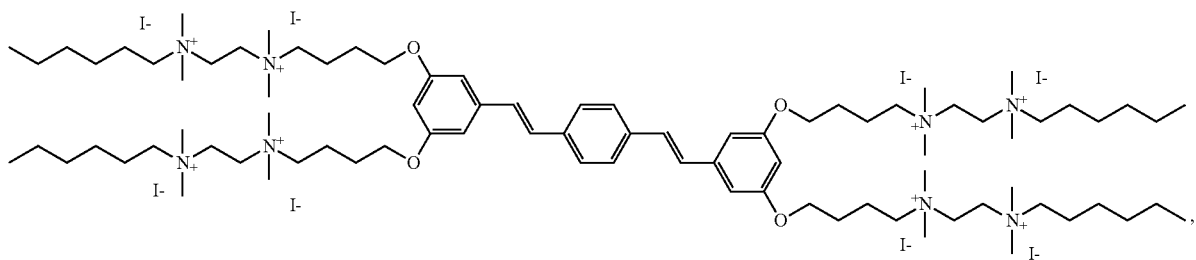
("COE2-3C-C4-en-hexyl")
Formula SS
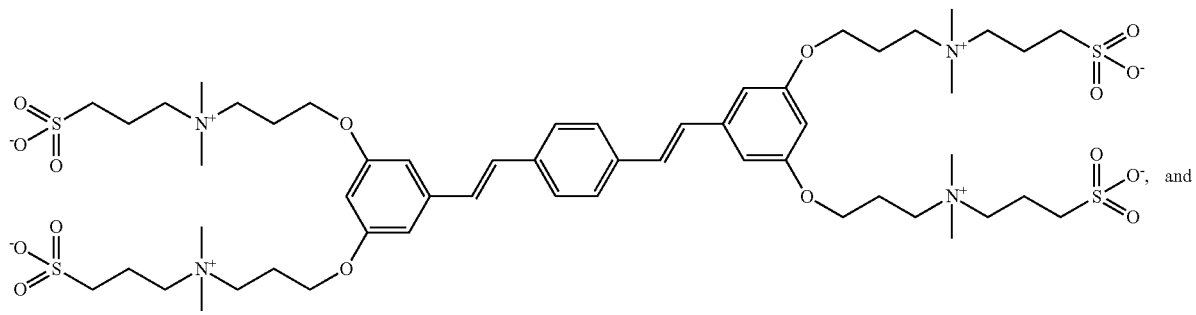
("COE2-3C-C3propyl-SO3"), and
Formula TT
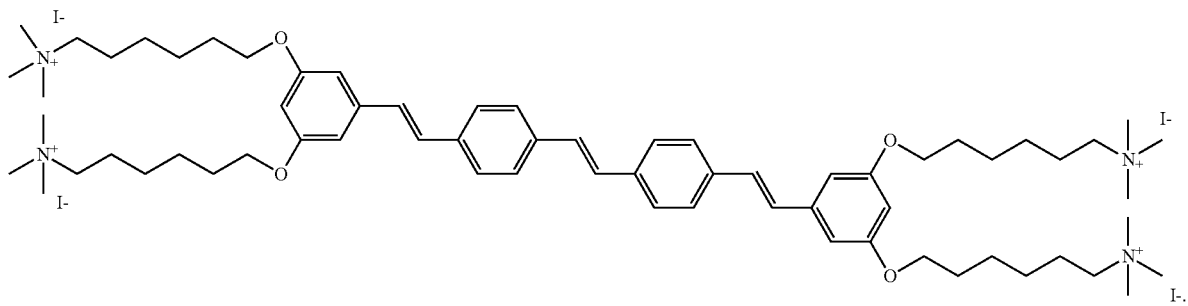
("COE2-4C")

In other embodiments, the COEs have a structure of Formulae TT, UU, VV or WW.
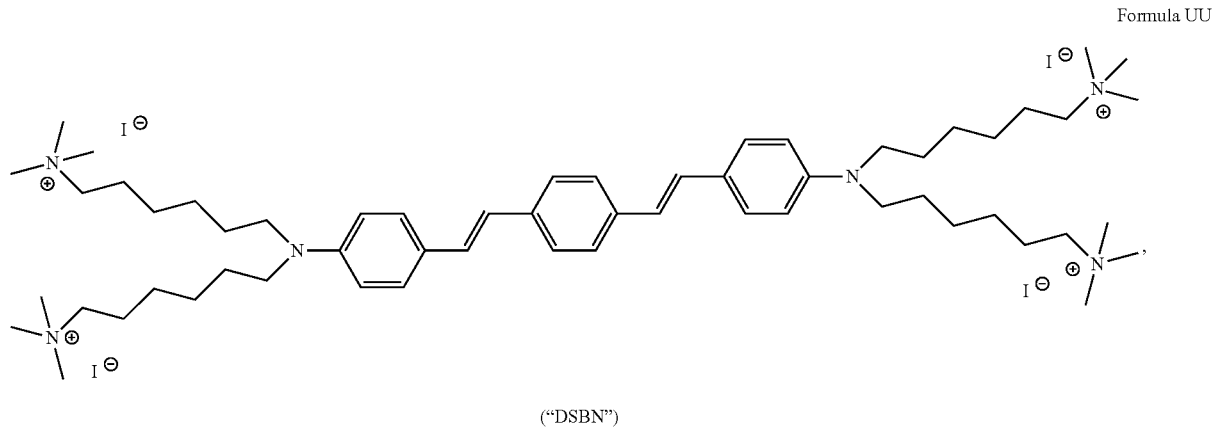
("DSBN")
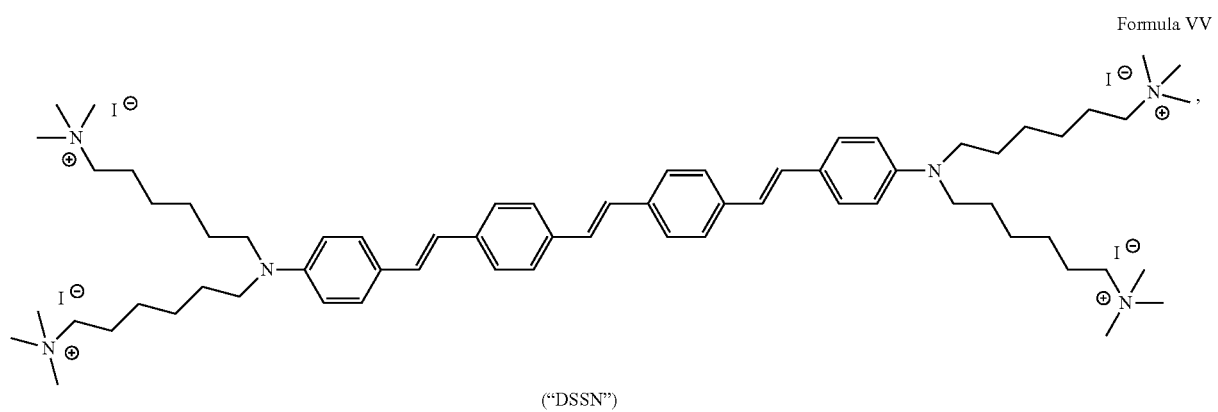
("DSSN")
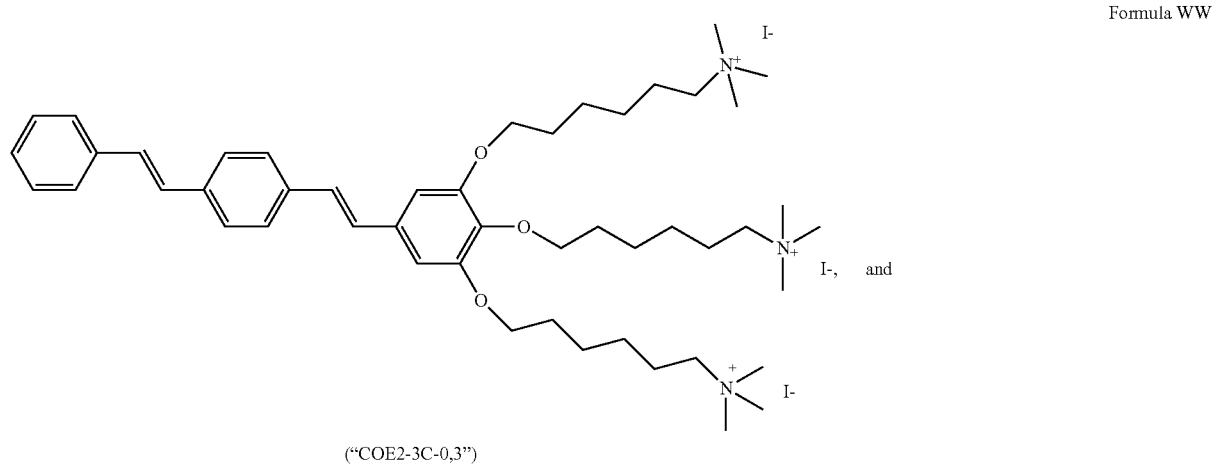
("COE2-3C-0,3")

Formula XX

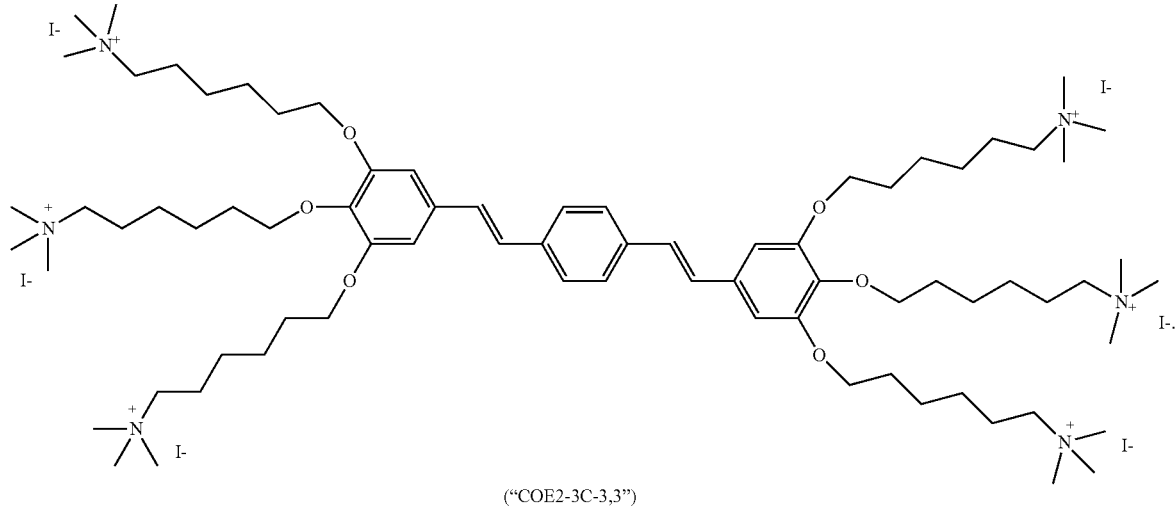

("COE2-3C-3,3")

In some embodiments, the COEs in the composition and/or methods described herein are not, or do not include, one that has a structure of Formula A, Formula O, Formula UU or Formula VV.

Some advantages of the COEs described herein compared to known COEs include how the molecular structure balances water solubility and efficacy. In some embodiments, increasing the hydrophobic components of the COE has been shown to increase efficacy. For example, COEs that have hexyl or cyclic groups (such as pyridinyl and piperidinyl) in place of the methyl groups attached to the quaternary nitrogens can have increased cell affinity and/or efficacy. In some embodiments, varying the hydrophobic components of the COEs described herein can reduce cytotoxicity. In some embodiments, by varying the number of carbons of the linker between the backbone of the compound (L1A and L1B) and the number of carbons of the groups attached to the quaternary nitrogens (L2A, L2B, L2C, L2D, L2E and L2F), while keeping the sum of the total number of carbons of the L1 groups+L2 groups constant, of a compound described herein, one can improve the efficacy of the compound while also minimizing the compound's cytotoxicity. As another example, optimization of toxicity is also achievable by tailoring the L1 groups, while keeping the L2 groups the same. The backbone of a compound described herein includes the phenyl groups and n moiety(ies).

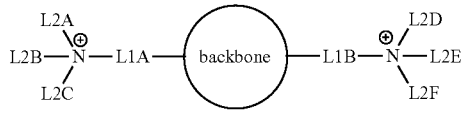

In various embodiments, one or more of the COEs have a high affinity towards cell membranes, especially bacterial cell membranes. For example, at least 50%, 60% or 70% of the COEs are taken up by or adsorbed to cells following incubation for 30 minutes, 1 hour, 1.5 hour, 2 hours or longer, given that the COEs are not at a concentration that oversaturates the cell culture medium or cells.

In various embodiments, the one or more COEs having a high affinity towards cells are also readily soluble in water or an aqueous medium. For example, the solubility of the COEs is at least 1, 2, 3, 4, 5, 6, 7, 8, 9, 10, 15, 20, 25, 30, 35, 40, 45, 50, 60, 70, 80, 90, 100, 500, or 1,000 µg/mL in water.

In some embodiments, the one or more COEs are active against Gram-negative bacteria. In some embodiments, the one or more COEs are active against Gram-positive bacteria. In some embodiments, the one or more COEs are active against both Gram-negative bacteria and Gram-positive bacteria. In various embodiments, one or more of the COEs have activity against one or more bacteria, such as *Salmonella enterica Typhimurium* (ST) (ATCC 14028); *E. coli* (EC) (ATCC 25922 and ATCC 47076); *Pseudomonas aeruginosa* (PA) (ATCC 10145 and (MDR) 1674623 and CDC0248); *Klebsiella pneumoniae* (KPN) (ATCC 13883 and ((MDR) ATCC BAA-2473 and CDC0010)); methicillin-resistant *S. aureus* (MRSA) (USA300, ATCC 33591 and ATC BAA-1717 MT3302; MT3315); methicillin-sensitive *S. aureus* (MSSA) (Newman and MT3305); *E. faecium* ((VRE) 1674620); *A. baumannii* ((MDR) 1674627 and CDC0290); *E. cloacae* ((ESBL) 1744299); *S. epidermidis* (ATCC 148990); *K. aerogenes* (ATCC 13048); *S. flexneri; Y. pseudotuberculosis; N. gonorrhoeae;* and *S. pneumoniae* (D39 and Daw 1).

In various embodiments, one or more of the COEs have a minimum inhibitory concentration (MIC) of less than 10, 20, 30, 40, 50, 60, or 70 µg/mL towards Gram-negative bacteria such as *Salmonella enterica Typhimurium* ATCC 14028; *E. coli* ATCC 25922 and ATCC 47076; *Pseudomonas aeruginosa* ATCC 10145, 1674623, and CDC0248; *Klebsiella pneumoniae* ATCC 13883, ATCC BAA-2473, and CDC0010; *Shigella flexneri; Yersinia pseudotuberculosis; Neisseria gonorrhoeae; Acinetobacter baumannii* 1674627 and CDC0290; *Entembacter cloacae* (ESBL) 1744299; and *Klebsiella aergenes* ATCC 13048. In some embodiments, the one or more COEs having a low MIC towards Gram-negative bacteria also have a low MIC towards Gram-positive bacteria such as methicillin-resistant *S. aureus* (MRSA) USA300, MT3302, MT3315, ATCC 33591, and ATCC BAA-1717; methicillin-sensitive *S. aureus* (MSSA) Newman and MT3305; *Streptococcus pneu-*

*moniae* D39 and Daw 1; Entercoccusfaecium (VRE) 1674620; *Staphylococcus epidermidis* ATCC 148990.

In various embodiments, the one or more COEs are active against Gram-negative bacteria and/or Gram-positive bacteria, and are non-toxic to mammalian cells. In various embodiments, the one or more COEs having a low MIC towards both Gram-negative and Gram-positive bacteria are also non-toxic to mammalian cells. For example, a COE at a concentration above its MIC towards a bacterial strain results in greater than 50%, 60%, 70%, 80%, 90%, 95% or higher viable cells upon incubation with a mammalian cell type.

Generally, the COE compounds are stable, and COEs can be stored in a solid or solution form for years. No decomposition is observed by detecting using NMR or mass spectrometry. In most embodiments, they are readily synthesized in a large scale.

Structural features such as the length of the PV backbone and the presence of either a trimethylammonium or a pyridinium cationic pendant group appears to generally affect the antimicrobial activity of the compounds. In various embodiments, optical characteristics and interactions with cell membranes are determined by using UV-Vis absorption and photoluminescence spectroscopies, and confocal microscopy. Toxicity tests on representative Gram-positive (*Enterococcus faecalis*) and Gram-negative (*Escherichia coli*) bacteria revealed generally greater toxicity to *E. faecalis* than to *E. coli* and may indicate that shorter molecules have better antimicrobial activity. In some embodiments, an increased antimicrobial potency is observed in three-ring COEs appended with pyridinium ionic groups but not with COEs with four or five PV repeat units. In further embodiments, a COE with only two PV repeat units may not associate with cells to the same degree as its longer homologs (i.e., DSBN and DSSN).

Pharmaceutical Compositions

In various embodiments, the present application provides a pharmaceutical composition for treatment of bacterial infection in a mammalian subject. The pharmaceutical composition includes one, two, three, four, or more compounds as represented by any of Formulae 1-7 (including Formula 3-a) and A-H and J-XX, and a pharmaceutically acceptable excipient. In some embodiments, the pharmaceutical composition can include a compound of Formula E and a pharmaceutically acceptable excipient or carrier. In another embodiment, the pharmaceutical composition includes a compound of Formula E in combination with one or more other compounds as represented by any of Formulae A-D and F-XX, with a pharmaceutically acceptable excipient or carrier.

The pharmaceutical compositions according to the present application can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the present application may be formulated for delivery via any route of administration. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by oral consumption or by injection. Methods for these administrations are known to one skilled in the art.

The pharmaceutical compositions according to the present application can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

Another drug delivery system, as a suitable pharmaceutical carrier for the COE compositions, is sustained released or increased circulatory half-life vehicles such as the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

The pharmaceutical compositions according to the present application can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The pharmaceutical compositions according to the present application may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

Methods of Preparation

Compounds of Formula 1, Formula 2, Formula 3, Formula 4, Formula 5, Formula 6, Formula 7, Formula (I), Formula (II), Formula (III), Formula (IV) and Formula (V), or a pharmaceutically acceptable isomer, racemate, hydrate, solvate, isotope, or salt of any of the foregoing, can be synthesized using standard synthetic techniques known to those skilled in the art, wherein Formula (I), Formula (II), Formula (III), Formula (IV) and Formula (V), or a pharmaceutically acceptable isomer, racemate, hydrate, solvate, isotope, or salt of any of the foregoing, are as provided in the section entitled "Further Formulae." For example, compounds of the present disclosure can be synthesized using appropriately modified synthetic procedures set forth in the general synthetic schemes detailed below and in the examples.

To this end, the reactions, processes, and synthetic methods described herein are not limited to the specific conditions described in the following experimental section, but rather are intended as a guide to one with suitable skill in the suitable field. For example, reactions may be carried out in any suitable solvent, or other reagents to perform the transformation(s) necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)).

General Synthetic Scheme A provides a representative synthesis for COEs described herein.

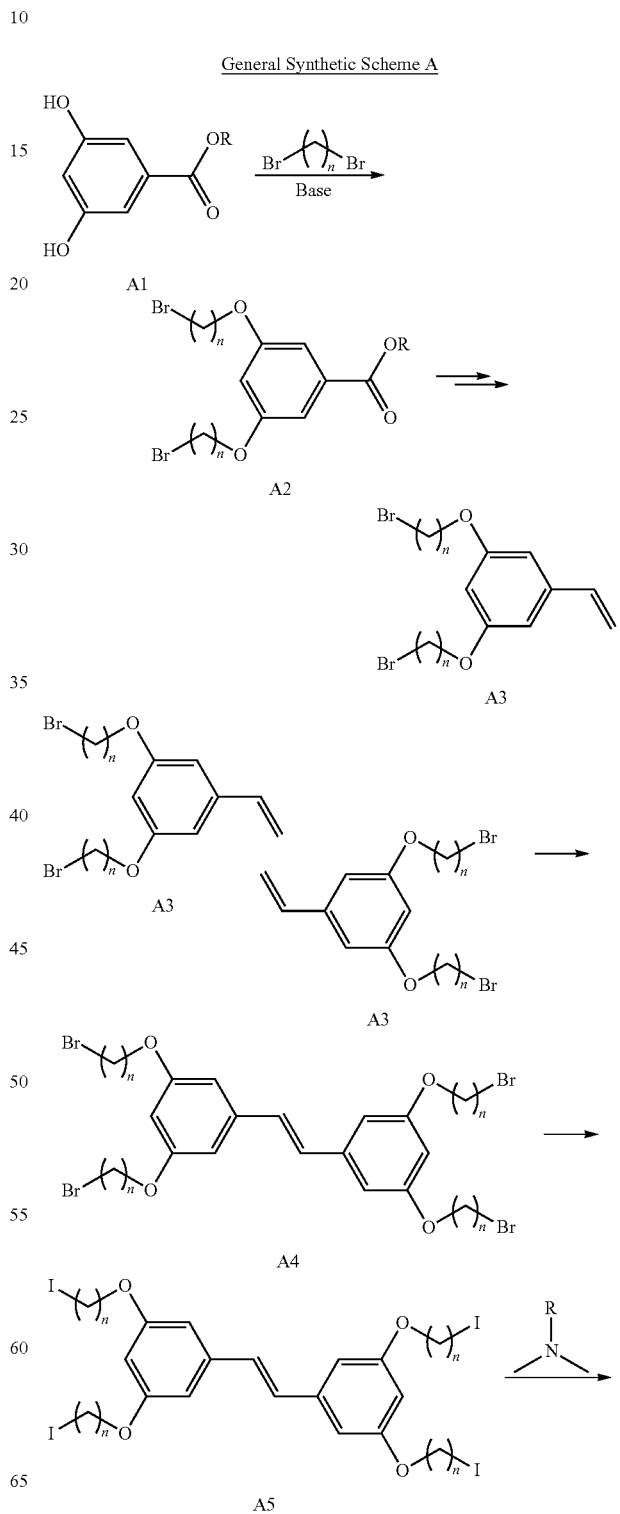

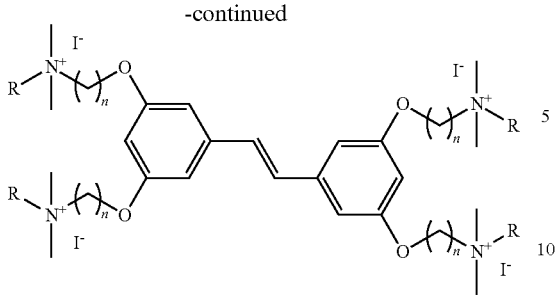

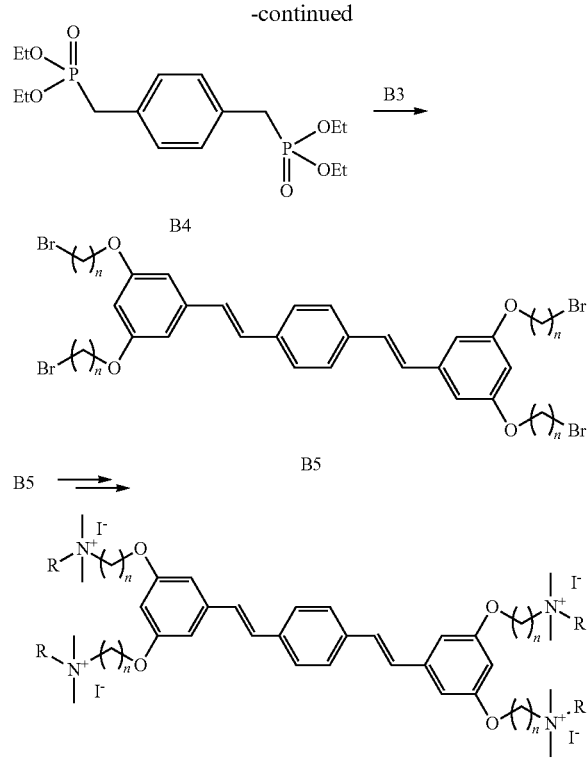

The reaction of A1 with a terminal, dibromo alkane under the appropriate conditions (for example, base and alkyl halide in acetone) provides bis-bromoalkyl ether, A2. Adaption of this method to varying lengths of alkane (wherein, without implying a restriction, n could be, for example, 1-12) is possible to those of ordinary skill in the art. Conversion of ester A2 to styrene A3 can be accomplished by a reduction (such as DIBAL, THF), oxidation (for example, $MnO_2$, DCM) and homologation (such as Wittig reaction) sequence. Two molecules of styrene A3 are reacted under Grubb's Metathesis conditions (such as Grubb's $2^{nd}$ generation catalyst, DCM) to give trans-stilbene A4. Reaction of A4 under the appropriate conditions (for example, NaI and acetone) provides A5 with reactive alkyl iodides. Treatment of A5 with a tertiary amine,

under the appropriate conditions (e.g. DMF, 45° C.) affords the final shown product.

General Synthetic Scheme B provides a representative synthesis for Compounds 7-6 of the present disclosure.

General Synthetic Scheme B

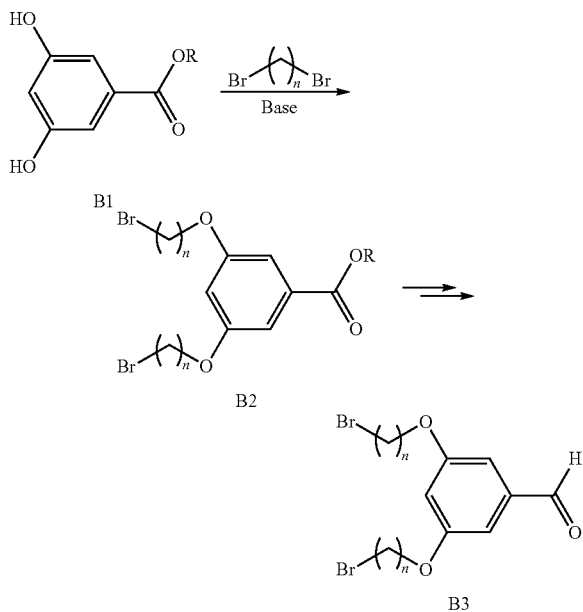

The reaction of B1 with a terminal, dibromo alkane under the appropriate conditions (such as base and alkyl halide in acetone) provides bis-bromoalkyl ether, B2. Adaption of this method to varying lengths of alkane (wherein, without implying a restriction, n could be, for example, 1-12) will be possible to those of ordinary skill in the art. Conversion of ester B2 to aldehyde B3 can be accomplished by a reduction (for example, DIBAL, THF), oxidation (for example, $MnO_2$, DCM or Swern oxidation) sequence. Compound B4 can be purchased or prepared according to methods known in the art. Two molecules of aldehyde B3 are reacted with B4 under appropriate Horner-Emmons-Wadsworth conditions (e.g. NaOtBu, THF) to provide B5. By analogy to General Reaction Scheme A, wherein A5 is converted to the final product, B5 is similarly converted to a target compound by the same iodination/amination sequence.

It should be noted that various alternative strategies for preparation of COEs described herein (compounds of Formula 1, Formula 2, Formula 3, Formula 4, Formula 5, Formula 6, Formula 7, Formula (I), Formula (II), Formula (III), Formula (IV) and Formula (V), or a pharmaceutically acceptable isomer, racemate, hydrate, solvate, isotope, or salt of any of the foregoing) are available to those of ordinary skill in the art, wherein Formula (I), Formula (II), Formula (III), Formula (IV) and Formula (V), or a pharmaceutically acceptable isomer, racemate, hydrate, solvate, isotope, or salt of any of the foregoing, are as provided in the section entitled "Further Formulae." For example, other compounds of Formula 1, Formula 2, Formula 3, Formula 4, Formula 5, Formula 6, Formula 7, Formula (I), Formula (II), Formula (III), Formula (IV) and Formula (V), or a pharmaceutically acceptable isomer, racemate, hydrate, solvate, isotope, or salt of any of the foregoing, can be prepared according to analogous methods using the appropriate starting material, wherein Formula (I), Formula (II), Formula (III), Formula (IV) and Formula (V), or a pharmaceutically acceptable isomer, racemate, hydrate, solvate, isotope, or salt of any of the foregoing, are as provided in the section entitled "Further Formulae." It will also be appreciated by those skilled in the art that in the processes for preparing the compounds described herein, the functional groups of intermediate compounds may need to be protected by suitable protecting groups. Such functional groups include, but are not limited to, hydroxy, amino, mercapto and carboxylic acid. Suitable protecting groups for hydroxy include, but are not limited to, trialkylsilyl or diarylalkylsilyl (for example, t-butyldimethylsilyl, t-butyldiphenylsilyl or trimethylsilyl), tetrahydropyranyl, benzyl, and the like). Suitable protecting groups for amino, amidino and guanidino include t-butoxycarbonyl ("Boc"), benzyloxycarbonyl, and the like. Protecting groups are optionally added or removed in accordance with standard techniques, which are known to one skilled in the art and as described herein. The use of protecting groups is described in detail in Green, T.W. and P.G.M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". Prodrugs of compounds of this disclosure are included within the scope of embodiments of the disclosure.

The examples and preparations provided below further illustrate and exemplify the compounds of the present application, methods of preparing such compounds and methods for evaluating biological activity.

Methods of Using

A method of treating, reducing the severity of and/or slowing the progression of a bacterial infection in a mammalian subject is provided including administering an effective amount of one, two, three, four, or more COEs of any of Formulae 1-7 (including Formula 3-a) and A-H and J-XX to a mammalian subject. In various embodiments, the effective amount of the COEs are non-toxic to the normal tissue or cells of the mammalian subject. In various embodiments, the mammalian subject is a human.

In various embodiments, the method of treating, reducing the severity of and/or slowing the progression of a bacterial infection in a mammalian subject has a specific efficacy towards Gram-negative, Gram-positive, or both, yet maintains the viability of normal mammalian cells of at least 70%, 80%, 90%, 95% or greater.

In some embodiments, the effective amounts of the COE(s) in the methods and/or compositions described herein may be in the range of about 0.001-0.01 mg/kg/day, 0.01-0.05 mg/kg/day, 0.05-0.1 mg/kg/day, 0.1-0.2 mg/kg/day, 0.2-0.3 mg/kg/day, 0.3-0.4 mg/kg/day, 0.4-0.5 mg/kg/day, 0.5-1 mg/kg/day, 1-5 mg/kg/day, 5-10 mg/kg/day, 10-20 mg/kg/day, 20-30 mg/kg/day, 30-40 mg/kg/day, 40-50 mg/kg/day, 50-60 mg/kg/day, 60-70 mg/kg/day, 70-80 mg/kg/day, 80-90 mg/kg/day, 90-100 mg/kg/day, 100-200 mg/kg/day, 200-300 mg/kg/day, 300-400 mg/kg/day, 400-500 mg/kg/day, 500-600 mg/kg/day, 600-700 mg/kg/day, 700-800 mg/kg/day, 800-900 mg/kg/day, 900-1000 mg/kg/day, 1000-1100 mg/kg/day, 1100-1200 mg/kg/day, 1200-1300 mg/kg/day, 1300-1400 mg/kg/day, 1400-1500 mg/kg/day, 1500-1600 mg/kg/day, 1600-1700 mg/kg/day, 1700-1800 mg/kg/day, 1800-1900 mg/kg/day, or 1900-2000 mg/kg/day. In some embodiments, the COE has a structure as shown in Formula E.

In other embodiments, the effective amounts of the COE(s) in the methods and/or compositions descried herein may be in the range of about 1-10 mg/kg/week, 10-30 mg/kg/week, 30-50 mg/kg/week, 50-100 mg/kg/week, 100-200 mg/kg/week, 200-300 mg/kg/week, 300-400 mg/kg/week, 400-500 mg/kg/week, 500-600 mg/kg/week, 600-700 mg/kg/week, 700-800 mg/kg/week, 800-900 mg/kg/week, 900-1000 mg/kg/week, 1000-1100 mg/kg/week, 1100-1200 mg/kg/week, 1200-1300 mg/kg/week, 1300-1400 mg/kg/week, 1400-1500 mg/kg/week, 1500-1600 mg/kg/week, 1600-1700 mg/kg/week, 1700-1800 mg/kg/week, 1800-1900 mg/kg/week or 1900-2000 mg/kg/week. In some embodiments, the COE has a structure as shown in Formula E.

In various embodiments, the methods described herein treats, reduces the severity of and/or slows the progression of one or more bacterial infections including but not limited to bacterial skin infections (e.g., Cellulitis, Folliculitis, Impetigo, Boils); foodborne illness such as nausea, vomiting, diarrhea, fever, chills and abdominal pain; sexually transmitted diseases such as *chlamydia*, gonorrhea, syphilis, bacterial vaginosis; and other bacterial infections such as bacterial meningitis, otitis media, urinary tract infection, and respiratory tract infections (e.g., sore throat, bronchitis, sinusitis).

In various embodiments, the mammalian subjects in the methods described herein may have developed antibiotic resistance, where bacteria are no longer sensitive to an antibiotic medication such as one or more of Vancomycin, Ceftobiprole, Ceftaroline, Clindamycin, Dalbavancin, Daptomycin, Fusidic acid, Linezolid, Mupirocin (topical), Oritavancin, Tedizolid, Telavancin, Tigecycline, Aminoglycosides, Carbapenems, Ceftazidime, Cefepime, Ceftobiprole, Ceftolozane/tazobactam, Fluoroquinolones, Piperacillin/tazobactam, Ticarcillin/clavulanic acid, Linezolid, Streptogramins, Tigecycline, and Daptomycin.

In some embodiments, the method described herein further includes administering an antibiotic medication in addition to the COE(s), which may be simultaneously, concurrently, or sequentially administered. Exemplary antibiotic medication includes Vancomycin, Ceftobiprole, Ceftaroline, Clindamycin, Dalbavancin, Daptomycin, Fusidic acid, Linezolid, Mupirocin (topical), Oritavancin, Tedizolid, Telavancin, Tigecycline, Aminoglycosides, Carbapenems, Ceftazidime, Cefepime, Ceftobiprole, Ceftolozane/tazobactam, Fluoroquinolones, Piperacillin/tazobactam, Ticarcillin/clavulanic acid, Linezolid, Streptogramins, Tigecycline, and Daptomycin.

Animal Model or Study

In various embodiments, the safety of COEs is studied in a mouse model. A range of drug doses is introduced into mice, for example, by intraperitoneal administration. Mice are monitored multiple times daily post-injection for toxicity evaluation. Compounds eliciting toxicity are generally re-tested at a lower dose or not pursued further. Compounds that are tolerated by mice in a dosage range that exhibits at least in vitro efficacy towards bacterial killing or inhibition are generally further tested for efficacy in bacterial clearance in infected mice. This can be pursued by subjecting the mice to virulent challenges with Gram-negative and Gram-positive organisms.

Examples

The following examples are provided to better illustrate the embodiments described herein and are not to be interpreted as limiting the scope of the present application. To the extent that specific materials are mentioned, it is merely for purposes of illustration and is not intended to limit the present application. One skilled in the art may develop equivalent means or reactants without the exercise of inventive capacity and without departing from the scope of the present application.

It is to be also understood that these examples are not meant to limit the methods used to test the compound(s), and that various modifications to an example described herein (e.g. use of additional cell types, use of different strains of the same cell type, or alternative methods) are well known to those of ordinary skill in the art. Further, the data presented herein is not intended to be comprehensive, but rather serve to demonstrate, by way of example, features of the present application.

General Procedures for Preparing COEs

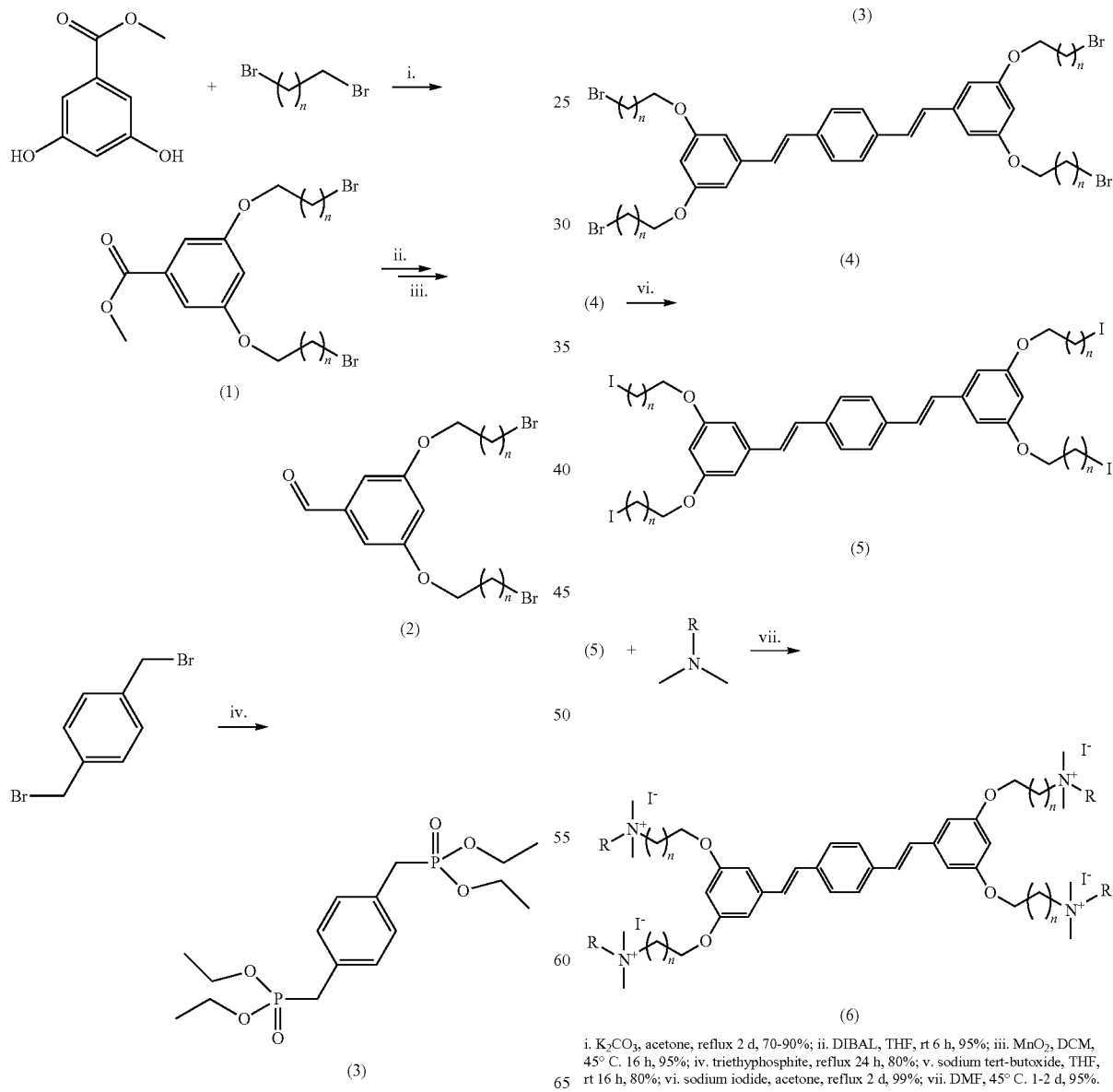

i. $K_2CO_3$, acetone, reflux 2 d, 70-90%; ii. DIBAL, THF, rt 6 h, 95%; iii. $MnO_2$, DCM, 45° C. 16 h, 95%; iv. triethyphosphite, reflux 24 h, 80%; v. sodium tert-butoxide, THF, rt 16 h, 80%; vi. sodium iodide, acetone, reflux 2 d, 99%; vii. DMF, 45° C. 1-2 d, 95%.

Synthesis of 3,5-bis((8-bromooctyl)oxy)benzaldehyde

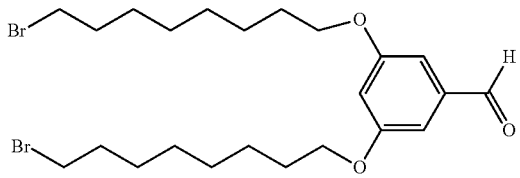 [SMILES: O=Cc1cc(OCCCCCCCCBr)cc(OCCCCCCCCBr)c1]

FIG. 1 shows a schematic of the synthesis of 3,5-bis((8-bromooctyl)oxy)benzaldehyde.

3,5-dihydroxybenzaldehyde (500 mg, 3.62 mmol), potassium carbonate (1.25 g, 9.05 mmol), and 1,8-dibromooctane (9.85 g, 36.2 mmol) were added to a 50 mL round bottom flask equipped with a stir bar. Acetone (20 mL) was added to the flask and a reflux condenser was fitted. The mixture was refluxed under argon atmosphere for two days. After cooling, the mixture was partitioned between ethyl acetate and brine. The aqueous phase was extracted with ethyl acetate three additional times. The combined organic phase was washed with brine three times, dried over magnesium sulfate, filtered, and concentrated by rotary evaporation. Column chromatography (1:10 ethyl acetate:hexane) afforded the product as a mixture with 1,8-dibromooctane. Residual starting material was removed by vacuum distillation to yield the pure product as a white semisolid (1.44 g, 77%). $^1$H NMR: (500 MHz, CDCl$_3$) δ 9.89 (s, 1H), 6.98 (d, J=2.3 Hz, 2H), 6.69 (t, J=2.3 Hz, 1H), 3.99 (t, J=6.5 Hz, 4H), 3.41 (t, J=6.8 Hz, 4H), 3.38 (d, J=6.6 Hz, 4H), 1.93-1.83 (m, 4H), 1.84-1.74 (m, 4H), 1.52-1.40 (m, 8H), 1.43-1.29 (m, 8H). $^{13}$C NMR (125 MHz, CDCl$_3$) δ 192.02, 160.71, 138.31, 108.01, 107.58, 68.33, 33.91, 32.74, 29.11, 29.05, 28.64, 28.05, 25.88.

Synthesis of 1,3-bis((8-bromooctyl)oxy)-5-vinylbenzene

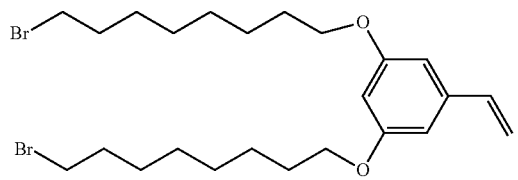 [SMILES: C=Cc1cc(OCCCCCCCCBr)cc(OCCCCCCCCBr)c1]

Figure 2:
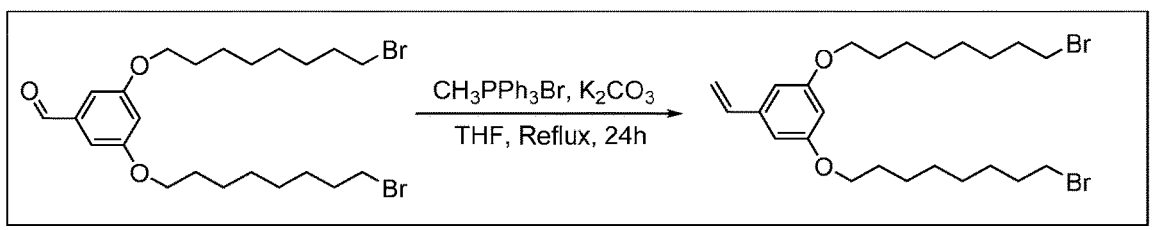
FIG. 2 depicts a schematic of the synthesis of 1,3-bis((8-bromooctyl)oxy)-5-vinylbenzene from 3,5-bis((8-bromooctyl)oxy)benzaldehyde.

FIG. 2 shows a schematic of the synthesis of 1,3-bis((8-bromooctyl)oxy)-5-vinylbenzene from 3,5-bis((8-bromooctyl)oxy)benzaldehyde.

3,5-bis((8-bromooctyl)oxy)benzaldehyde (300 mg, 0.577 mmol), potassium carbonate (87.5 mg, 0.634 mmol), and methyltriphenylphosphonium bromide (227 mg, 0.634 mmol) were added to a flame-dried 15 mL round bottom flask equipped with a stir bar. Tetrahydrofuran (7 mL) was added to the flask and a reflux condenser was fitted. The mixture was refluxed for 24 hours under argon atmosphere. After cooling, the mixture was partitioned between ethyl acetate and brine. The aqueous phase was extracted an additional 3 times with ethyl acetate. The combined organic phase was washed with brine three times, dried over sodium sulfate, filtered, and concentrated by rotary evaporation. Column chromatography (1:15 ethyl acetate:hexane) afforded the pure product as a clear oil (220 mg, 74%). $^1$H NMR (400 MHz, CDCl$_3$) δ 6.61 (dd, J=17.5, 10.8 Hz, 1H), 6.53 (d, J=2.3 Hz, 2H), 6.35 (t, J=2.3 Hz, 1H), 5.69 (d, J=17.5 Hz, 1H), 5.21 (d, J=10.8 Hz, 1H), 3.92 (t, J=6.5 Hz, 4H), 3.39 (t, J=6.8 Hz, 4H), 1.84 (p, J=6.9 Hz, 4H), 1.75 (p, J=6.7 Hz, 4H), 1.50-1.37 (m, 16H). $^{13}$C NMR (125 MHz, CDCl$_3$) δ 160.35, 139.47, 136.92, 114.11, 104.83, 100.96, 77.25, 77.00, 76.74, 67.93, 33.97, 32.77, 29.21, 29.16, 28.68, 28.08, 25.95.

Synthesis of (E)-1,2-bis(3,5-bis((8-bromooctyl)oxy)phenyl)ethene

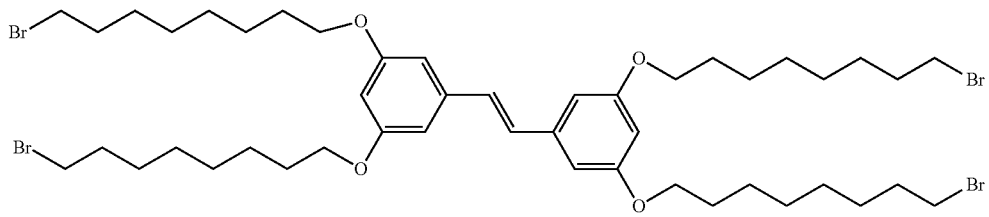 [SMILES: BrCCCCCCCCOc1cc(/C=C/c2cc(OCCCCCCCCBr)cc(OCCCCCCCCBr)c2)cc(OCCCCCCCCBr)c1]

Figure 3:
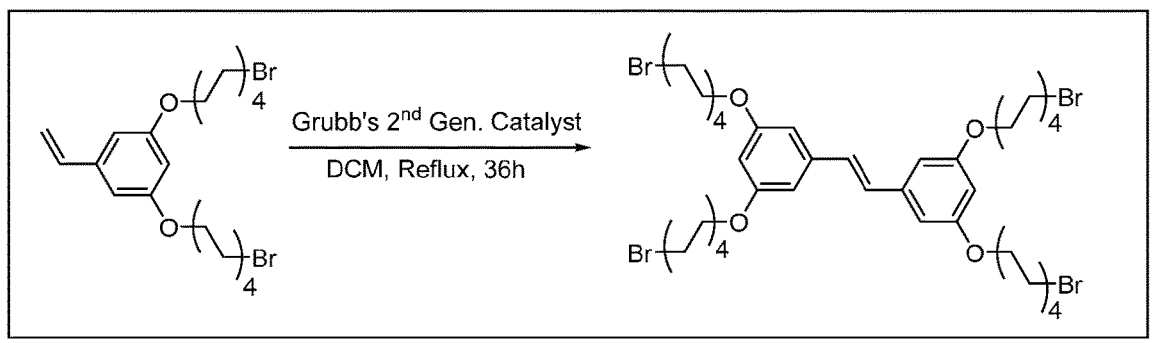
FIG. 3 depicts a schematic of the synthesis of (E)-1,2-bis(3,5-bis((8-bromooctyl)oxy)phenyl)ethene from 1,3-bis((8-bromooctyl)oxy)-5-vinylbenzene.

FIG. 3 depicts a schematic of the synthesis of (E)-1,2-bis(3,5-bis((8-bromooctyl)oxy)phenyl)ethene from 1,3-bis((8-bromooctyl)oxy)-5-vinylbenzene.

1,3-bis((8-bromooctyl)oxy)-5-vinylbenzene (125 mg, 0.214 mmol) was added to a 10 mL flame dried round bottom flask equipped with a stir bar. The flask was subsequently evacuated and refilled with argon three times and 3 mL of anhydrous dichloromethane was added. Grubb's Catalyst 2nd Generation (1.5 mg, 0.0018 mmol) was added to a separate dry vessel. Anhydrous DCM (2 mL) was added to the second vessel. Once the catalyst was dissolved, it was transferred via syringe to the reaction vessel. The mixture was stirred at 50° C. for 36 hours (monitored by TLC for completion). After cooling, the crude mixture was concentrated by rotary evaporation. Column chromatography (5:7 chloroform:hexane) afforded the pure product as a white solid (100 mg, 79%). $^1$H NMR: (500 MHz, CDCl$_3$) δ 6.99 (s, 2H), 6.64 (d, J=2.2 Hz, 4H), 6.39 (t, J=2.2 Hz, 2H), 3.98 (t, J=6.5 Hz, 8H), 3.42 (t, J=6.8 Hz, 8H), 1.87 (p, J=7.3 Hz, 8H), 1.79 (p, J=6.6 Hz, 8H), 1.57-1.31 (m, 32H). $^{13}$C NMR (125 MHz, CDCl$_3$) δ 160.44, 139.08, 129.11, 105.14, 103.73, 100.97, 77.25, 76.99, 76.74, 67.98, 33.97, 32.78, 29.23, 29.16, 28.68, 28.09, 25.97.

Synthesis of (E)-1,2-bis(3,5-bis((8-iodooctyl)oxy)phenyl)ethene

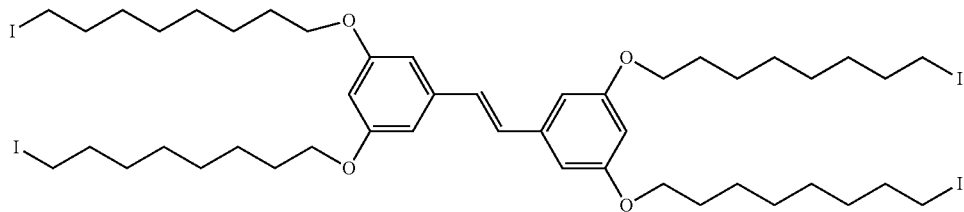 [SMILES: ICCCCCCCCOc1cc(/C=C/c2cc(OCCCCCCCCI)cc(OCCCCCCCCI)c2)cc(OCCCCCCCCI)c1]

Figure 4:
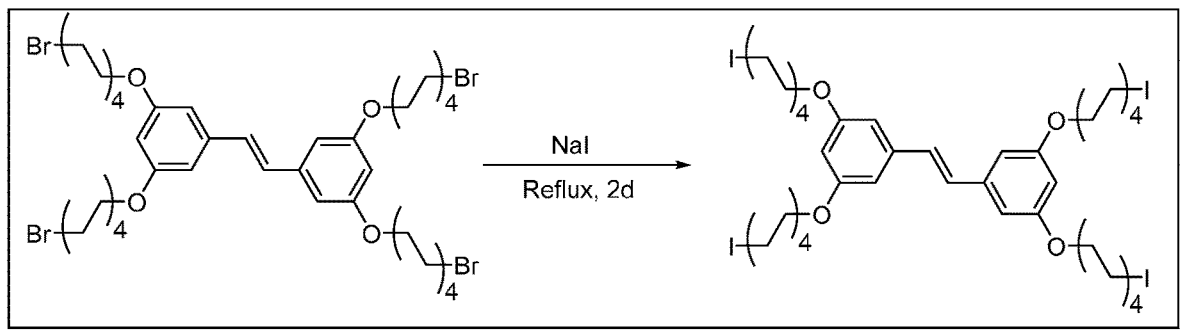
FIG. 4 depicts a schematic of the synthesis of (E)-1,2-bis(3,5-bis((8-iodooctyl)oxy)phenyl)ethene from (E)-1,2-bis(3,5-bis((8-bromooctyl)oxy)phenyl)ethene.

FIG. 4 depicts a schematic of the synthesis of (E)-1,2-bis(3,5-bis((8-iodooctyl)oxy)phenyl)ethene from (E)-1,2-bis(3,5-bis((8-bromooctyl)oxy)phenyl)ethene.

To a 5 mL round bottom flask equipped with a stir bar was added (E)-1,2-bis(3,5-bis((8-bromooctyl)oxy)phenyl)ethene (47 mg, 0.047 mmol), sodium iodide (105 mg, 0.701 mmol), and acetone (2.5 mL). A reflux condenser was added and the mixture was stirred at reflux under argon atmosphere for 2 days. The mixture was partitioned between DCM and water. The organic phase was removed, dried over sodium sulfate, and concentrated to afford the pure product as a white solid (50 mg, 89%). $^1$H NMR (500 MHz, CDCl$_3$) δ 6.99 (s, 2H), 6.64 (d, J=2.2 Hz, 4H), 6.39 (t, J=2.2 Hz, 2H), 3.98 (t, J=6.5 Hz, 8H), 3.20 (t, J=7.0 Hz, 8H), 1.91-1.75 (m, 16H), 1.54-1.31 (m, 32H).

Synthesis of COE2-2C-C8 (Formula B)

as a fluffy, white solid (44 mg, 92%). $^1$H NMR (500 MHz, DMSO-d$_6$) δ 7.17 (s, 2H), 6.74 (s, 4H), 6.37 (s, 2H), 3.97 (t, J=6.33 Hz, 8H), 3.28-3.26 (m, 8H), 3.16 (s, 12H), 3.04 (s, 24H), 1.75-1.64 (m, 16H), 1.41-1.28 (m, 32H). $^{13}$C NMR (125 MHz, DMSO-d$_6$) δ 160.48, 139.38, 129.31, 105.39, 101.15, 67.94, 65.75, 52.61, 29.20, 29.06, 28.95, 26.20, 25.94, 22.49.

Synthesis of 3,5-bis((4-bromobutyl)oxy)benzaldehyde

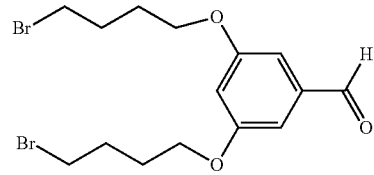 [SMILES: O=Cc1cc(OCCCCBr)cc(OCCCCBr)c1]

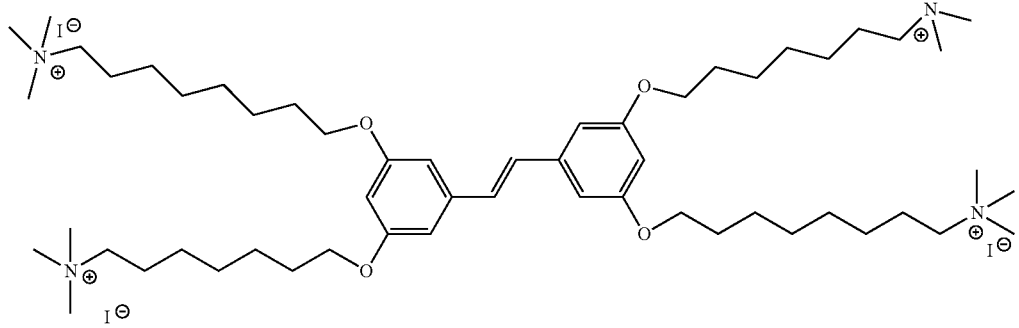

Figure 5:
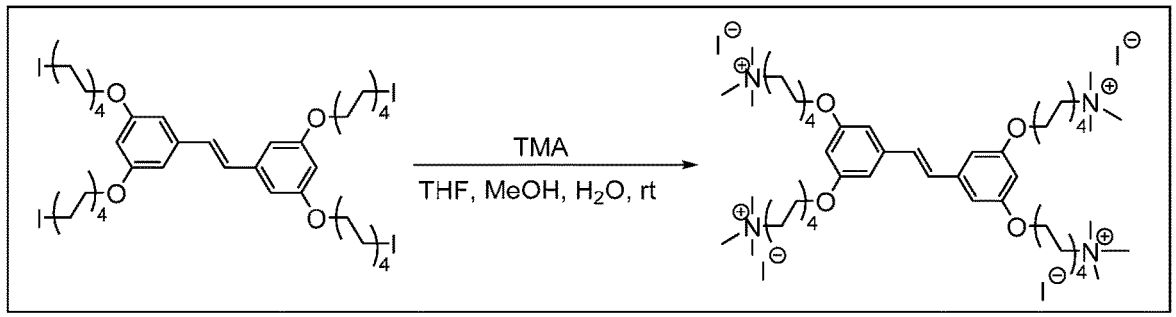
FIG. 5 depicts a schematic of the synthesis of COE2-2C-C8.
Figure 6:
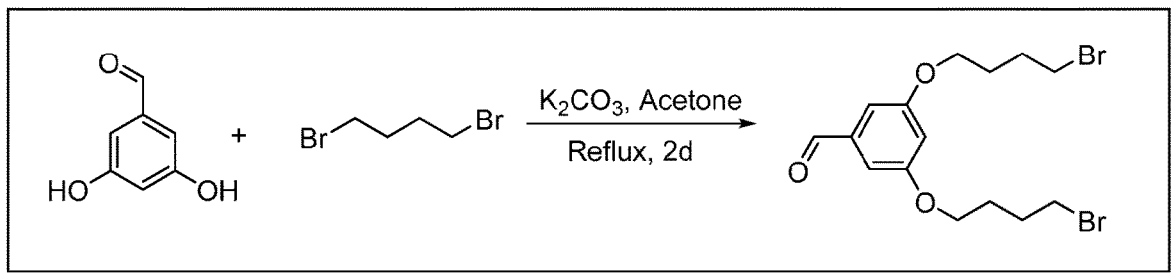
FIG. 6 depicts a schematic of the synthesis of 3,5-bis((4-bromobutyl)oxy)benzaldehyde.

FIG. 5 depicts a schematic of the synthesis of Formula B. (E)-1,2-bis(3,5-bis((8-iodobutyl)oxy)phenyl)ethene (40 mg, 0.033 mmol) and THF (1.5 mL) were added to a 5 mL round bottom flask equipped with a stir bar under argon atmosphere. A solution of trimethylamine (3.2M in methanol, 0.1 mL, 0.32 mmol) was added to the reaction vessel via syringe. The argon line was removed and the vessel was sealed with electrical tape and parafilm. The mixture was allowed to stir at room temperature for 6 hours, at which point precipitates become visible. Sufficient methanol was added to the mixture to completely dissolve the precipitates and the mixture was stirred for an additional 12 hours. Precipitates were again observed and minimal water was used to re-dissolve the solids. After another 12 hours, the mixture was purged with argon for 30 mins before concentration by rotary evaporation. DI water (~2 mL) was added, the mixture was filtered through a 0.4 μm syringe filter, and the solution was lyophilized. The pure product was obtained FIG. 6 depicts a schematic of the synthesis of 3,5-bis((4-bromobutyl)oxy)benzaldehyde.

3,5-dihydroxybenzaldehyde (800 mg, 5.79 mmol), potassium carbonate (2.0 g, 14.5 mmol), 1,4-dibromobutane (12.5 g, 58.1 mmol), and acetone (20 mL) were added to a 50 mL round bottom flask equipped with a stir bar. A reflux condenser was fitted and the mixture was refluxed under argon atmosphere for two days. After cooling, the mixture was partitioned between ethyl acetate and brine. The aqueous phase was extracted with ethyl acetate three additional times. The combined organic phase was washed with brine three times, dried over magnesium sulfate, filtered, and concentrated by rotary evaporation. Column chromatography (1:8 ethyl acetate:hexane) afforded the pure product as a clear oil (1.80 g, 76%). $^1$H NMR: (600 MHz, CDCl$_3$) δ 9.89 (s, 1H), 6.99 (d, J=2.3 Hz, 2H), 6.69-6.67 (m, 1H), 4.03 (t, J=6.1 Hz, 4H), 3.49 (t, J=6.6 Hz, 4H), 2.10-2.04 (m, 4H), 1.99-1.93 (m, 4H). $^{13}$C NMR: (151 MHz, CDCl$_3$) δ 191.81, 160.48, 138.39, 107.96, 107.68, 77.20, 76.99, 76.78, 67.30, 33.21, 29.36, 27.74.

Synthesis of 3,5-bis((4-iodobutyl)oxy)benzaldehyde

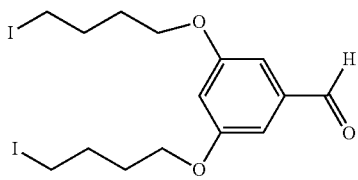 [SMILES: O=Cc1cc(OCCCCI)cc(OCCCCI)c1]

Figure 7:
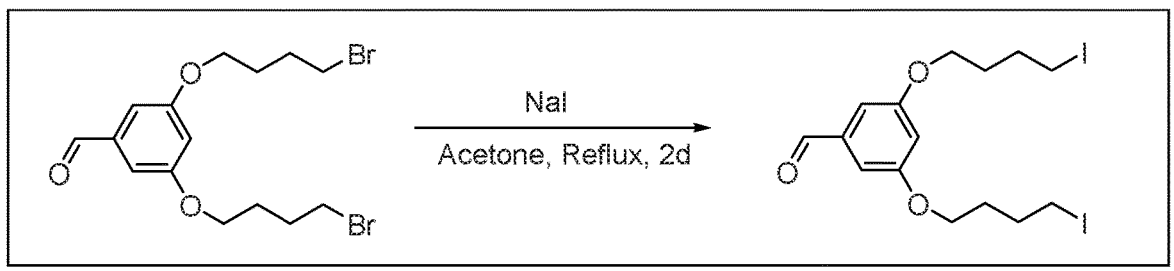
FIG. 7 depicts the synthesis of 3,5-bis((4-iodobutyl)oxy)benzaldehyde.

FIG. 7 depicts the synthesis of 3,5-bis((4-iodobutyl)oxy)benzaldehyde.

3,5-bis((4-bromobutyl)oxy)benzaldehyde (678 mg, 1.93 mmol), sodium iodide (2.34 g, 15.6 mmol), and acetone (12 mL) were added to a 25 mL round bottom flask with a stir bar. A reflux condenser was fitted and the mixture was refluxed under argon for two days. The mixture was partitioned between ethyl acetate and water. The organic phase was removed, dried over sodium sulfate, and concentrated to afford the pure product as a clear oil (690 mg, 88%). $^{13}$C NMR (151 MHz, CDCl$_3$) δ 191.82, 160.47, 138.37, 107.96, 107.68, 67.09, 30.06, 29.98, 6.11.

Synthesis of 1,4-bis((E)-3,5-bis(4-iodobutoxy)styryl)benzene

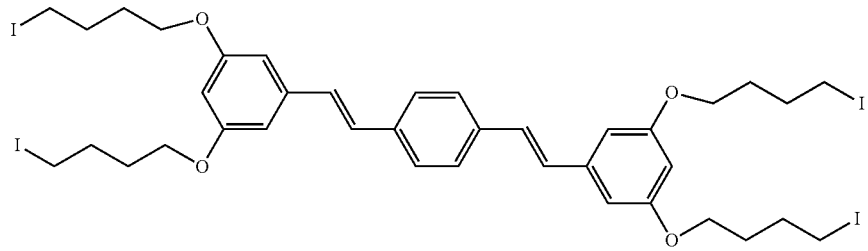 [SMILES: ICCCCOc1cc(/C=C/c2ccc(/C=C/c3cc(OCCCCI)cc(OCCCCI)c3)cc2)cc(OCCCCI)c1]

Figure 8:
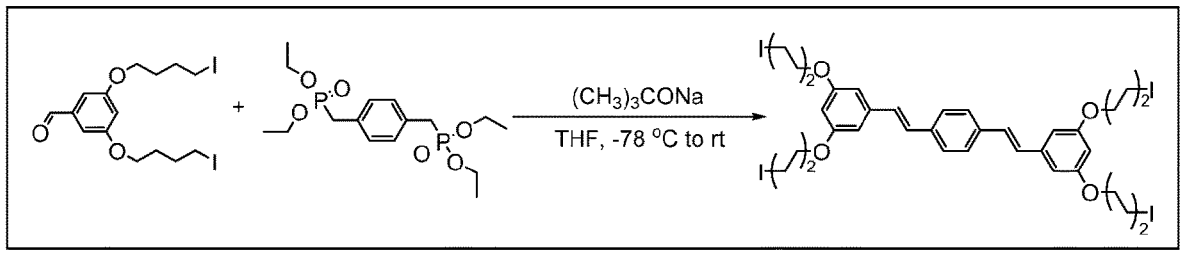
FIG. 8 depicts the synthesis of 1,4-bis((E)-3,5-bis(4-iodobutoxy)styryl)benzene.

FIG. 8 depicts the synthesis of 1,4-bis((E)-3,5-bis(4-iodobutoxy)styryl)benzene.

3,5-bis((4-iodobutyl)oxy)benzaldehyde (430 mg, 1.05 mmol) and 1,4-phenylenebis(methylene)bis(diethylphosphonate) (394 mg, 1.2 mmol) were added to flame dried 25 mL round bottom flask equipped with a stir bar. The vessel was subsequently evacuated and backfilled with argon three times. Anhydrous THF (8 mL) was added to the reaction vessel and the mixture was cooled to −78° C. in a dry ice-acetone bath. Sodium tert-butoxide (109 mg, 1.13 mmol) was added to a second flask under argon atmosphere, dissolved in 4 mL of anhydrous THF, and added to the reaction vessel slowly via syringe. The resulting mixture was kept at −78° C. for 20 mins before being allowed to warm temperature. After stirring for 16 hours, the mixture was partitioned between ethyl acetate and brine. The aqueous phase was extracted with three additional portions of ethyl acetate. The combined organic phase was washed with brine three times, dried over sodium sulfate, filtered, and concentrated by rotary evaporation. Column chromatography (1:10 ethyl acetate:hexane) afforded the pure product as a yellowish solid (805 mg, 71%). $^1$H NMR: (500 MHz, CDCl$_3$) δ 7.43 (s, 4H), 7.07-6.91 (m, 4H), 6.59 (d, J=2.2 Hz, 4H), 6.30 (t, J=2.2 Hz, 2H), 3.95 (t, J=6.1 Hz, 8H), 3.22 (t, J=6.9 Hz, 8H), 2.08-1.94 (m, 8H), 1.90-1.79 (m, 8H).

Synthesis of COE2-3C-C4 (Formula F)

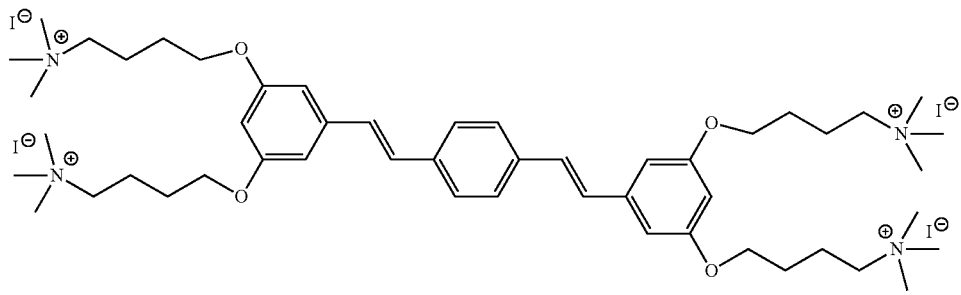

Figure 9:
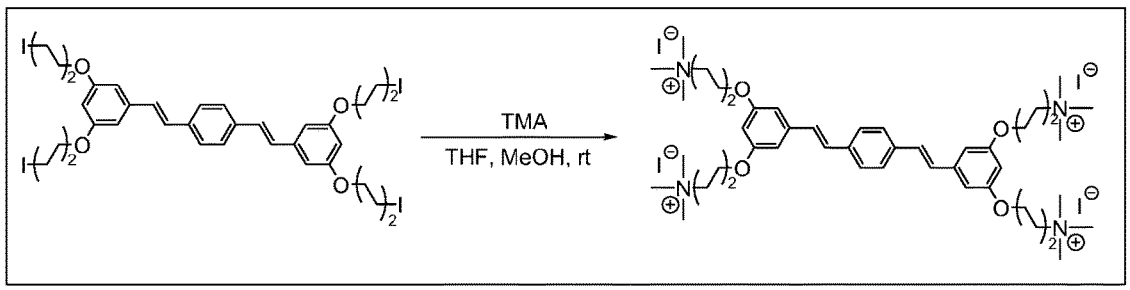
FIG. 9 depicts the synthesis of Formula F (COE2-3C-C4).

FIG. 9 depicts the synthesis of Formula F.

1,4-Bis((E)-3,5-bis(4-iodobutoxy)styryl)benzene (100 mg, 0.093 mmol) and THF (3 mL) were added to a 10 mL round bottom flask equipped with a stir bar under argon atmosphere. A solution of trimethylamine (3.2M in methanol, 0.3 mL, 0.906 mmol) was added to the reaction vessel via syringe. The vessel was sealed with electrical tape and parafilm and allowed to stir at room temperature for 12 hours. Methanol was added to dissolve the precipitates that were observed at this time. The mixture was stirred for an addition 12 hours and methanol was again added to dissolve precipitates. Following another 16 hours, the solution was purged with argon for 20 minutes and concentrated by rotary evaporation. DI water (~1.5 mL) was added, the mixture was filtered through a 0.4 μm syringe filter, and the solution was lyophilized. The pure product was obtained as a fluffy, yellowish solid (110 mg, 91%). $^1$H NMR (600 MHz, DMSO-d$_6$) δ 7.60 (s, 1H), 7.25 (dd, J=36.5, 15.9 Hz, 1H), 6.81 (s, 1H), 6.44 (s, OH), 4.05 (t, J=6.2 Hz, 3H), 3.43-3.37 (m, 3H), 3.10-3.04 (m, 13H), 1.90-1.79 (m, 3H), 1.74 (p, J=6.8 Hz, 3H). $^{13}$C NMR (151 MHz, DMSO-d$_6$) δ 160.27, 139.60, 136.82, 129.03, 128.82, 127.36, 109.99, 105.67, 101.43, 67.32, 65.45, 52.74, 52.72, 52.69, 40.43, 40.30, 40.16, 40.02, 39.88, 39.81, 39.74, 39.60, 26.10, 19.70. HRMS (ESI): ([M-2I]2+) calcd: 528.2213, found: 528.2205.

Synthesis of COE2-2B (Formula D)

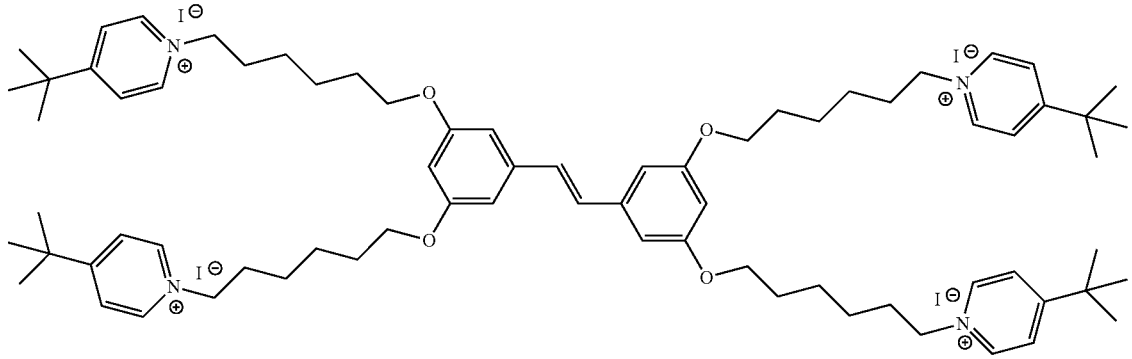 [SMILES: [I-] ; CC(C)(C)c1cc[n+](CCCCCCOc2cc(/C=C/c3cc(OCCCCCC[n+]4ccc(C(C)(C)C)cc4)cc(OCCCCCC[n+]4ccc(C(C)(C)C)cc4)c3)cc(OCCCCCC[n+]3ccc(C(C)(C)C)cc3)c2)cc1 ; [I-] ; [I-] ; [I-]]

Figure 10:
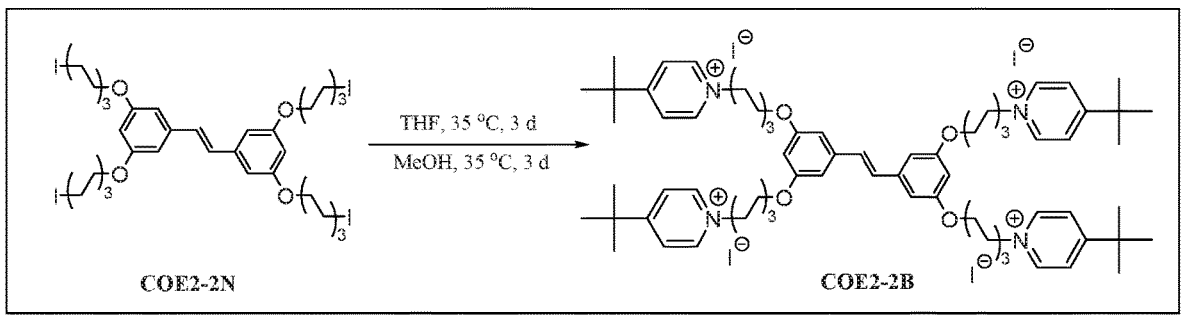
FIG. 10 depicts the synthesis of Formula D (COE2-2B).

FIG. 10 depicts the synthesis of Formula D.

COE2-2N (108.4 mg, 0.1 mmol, 1.0 eq.) was dissolved in dry THF and a large excess of 4-t-butylpyridine (1.2 mL, 20 eq.) was added. The resulting solution was stirred under argon at 35° C. for 3 days. The solution turned yellow and cloudy. Adding 10 mL MeOH, the solution was stirred for another 3 days. The solvent was removed via rotary evaporation. The resulting orange solid was dissolved in MeOH and added into 40 mL ether. After centrifugation at 7000 rpm for 3 mins, the supernatant was poured out and the process was repeated twice. The resulting solid was dried in vacuo overnight. Formula D was afforded as a light yellow solid (131 mg, 80% yield). H-NMR: (500 MHz, CD$_3$OD: CD$_2$Cl$_2$) δ 8.904 (d, 8H), 8.118 (d, 8H), 7.129 (s, 2H), 6.757 (d, J=2.0 Hz, 4H), 6.413 (t, J=2.0 Hz, 2H), 4.647 (t, J=7.5 Hz, 8H), 4.039 (t, J=6.0 Hz, 8H), 2.092 (p, J=7.5 Hz, 8H), 1.851 (p, J=3.5 Hz, 8H), 1.637 (p, J=7.5 Hz, 8H), 1.507 (p, J=3.5 Hz, 8H), 1.457 (s, 36H). $^{13}$C-NMR (125 MHz, CD$_3$OD: CD$_2$Cl$_2$) S 172.822, 161.899, 145.227, 126.677, 106.298, 68.864, 62.041, 37.654, 32.362, 30.364, 26.838, 26.624.

Synthesis of COE2-2py (Formula C)

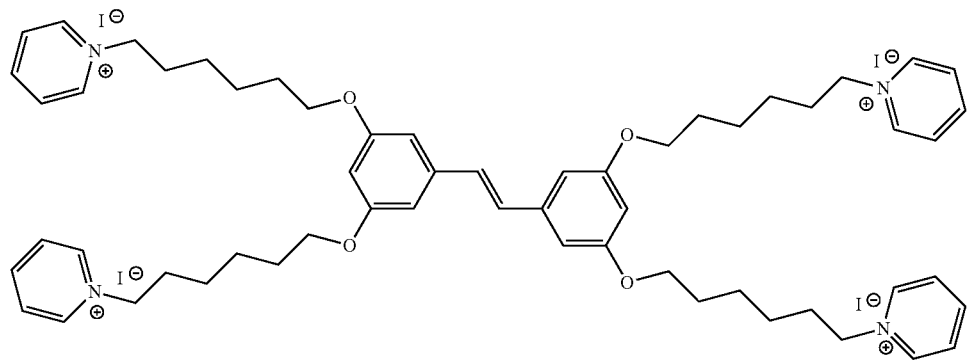 [SMILES: [I-] ; C(=C\c1cc(OCCCCCC[n+]2ccccc2)cc(OCCCCCC[n+]2ccccc2)c1)/c1cc(OCCCCCC[n+]2ccccc2)cc(OCCCCCC[n+]2ccccc2)c1 ; [I-] ; [I-] ; [I-]]

Figure 11:
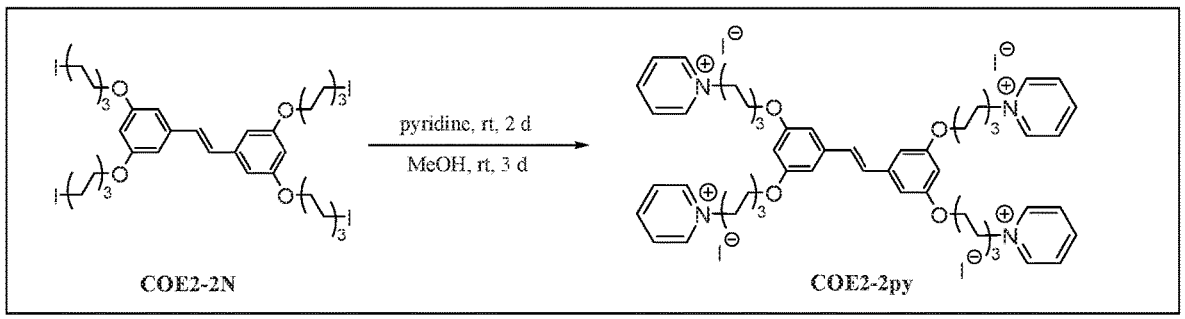
FIG. 11 depicts the synthesis of Formula C (COE2-2py).

FIG. 11 depicts the synthesis of Formula C.

COE2-2N (20 mg, 0.141 mmol) was stirred in ~1 mL of pyridine at room temperature for 6 days. After 2 days, ~10 mL methanol was added to aid dissolution. Volatiles were removed and the resulting solid was slurried in hexanes and filtered to collect a light orange solid, which was further dissolved in minimum amount of MeOH and added into 40 mL pentane. After centrifugation at 7000 rpm for 3 min, the resulting solid was dried in vacuo overnight. Formula C was afforded as a white solid (9 mg, 34.5% yield). H-NMR: (500 MHz, $CD_3OD$) δ 9.091 (d, J=6.5 Hz, 8H), 8.628 (t, J=8 Hz, 4H), 8.145 (t, J=7 Hz, 8H), 7.162 (s, 2H), 6.780 (s, 4H), 6.402 (s, 2H), 4.731 (t, J=8 Hz, 8H), 4.059 (t, J=6.5 Hz, 8H), 2.126 (p, J=7.5 Hz, 8H), 1.853 (p, J=7 Hz, 8H), 1.645 (p, J=7.5 Hz, 8H), 1.531 (p, J=7 Hz, 8H). $^{13}$C-NMR (125 MHz, $CD_3OD$) δ 162.007, 147.032, 146.150, 140.854, 129.673, 106.380, 102.300, 68.980, 63.189, 32.561, 30.223, 27.004, 26.772.

Synthesis of COE2-2hexyl (Formula E)

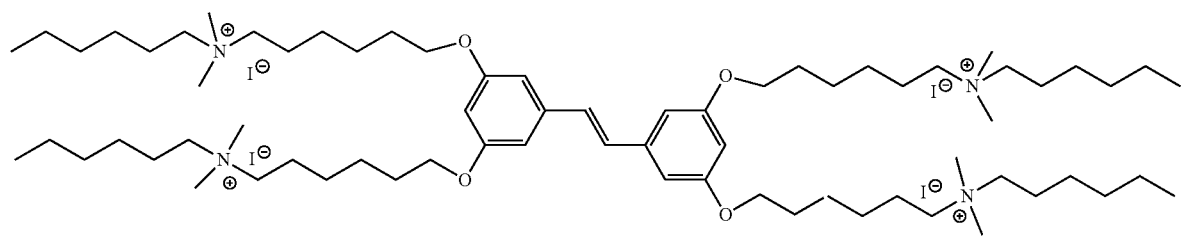 [SMILES: CCCCCC[N+](C)(C)CCCCCCOc1cc(/C=C/c2cc(OCCCCCC[N+](C)(C)CCCCCC)cc(OCCCCCC[N+](C)(C)CCCCCC)c2)cc(OCCC)c1 ; [I-] ; [I-] ; CCCCCC[N+](C)(C)CCCC ; [I-] ; [I-]]

Figure 12:
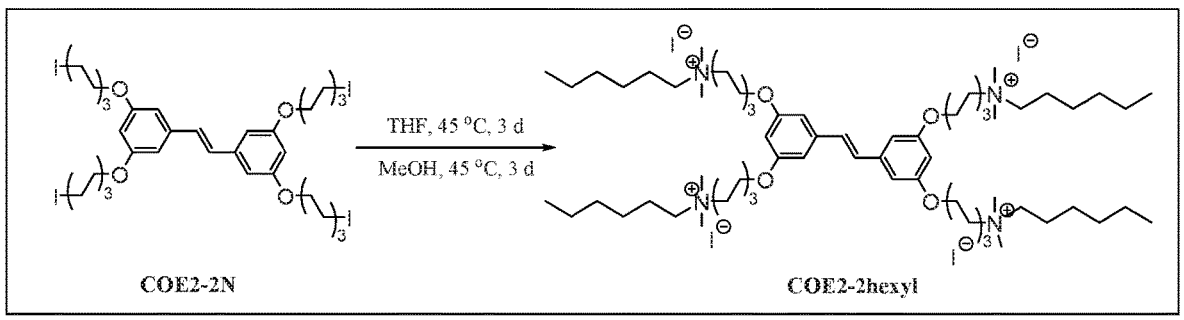
FIG. 12 depicts the synthesis of Formula E (COE2-2hexyl).

FIG. 12 depicts the synthesis of Formula E.

COE2-2N (54.2 mg, 0.05 mmol, 1.0 eq.) was dissolved in 15 mL dry THF and a large excess of N,N-dimethylhexylamine (0.3 mL, 20 eq.) was added. The resulting solution was stirred under argon at 45° C. for 3 days. Some white solid precipitated out. Adding 5 mL MeOH, the solution was stirred for another 1 day. The solvent was removed via rotary evaporation. The resulting crude product was dissolved in minimum amount of MeOH and added into 40 mL ether. After centrifugation at 7000 rpm for 3 mins, the resulting solid was dried in vacuo for 5 hours. Formula E was afforded as a white solid (131 mg, 80% yield). H-NMR: (500 MHz, $CD_3OD$) δ 7.221 (s, 2H), 6.828 (d, 4H), 6.433 (m, 2H), 4.067 (t, J=5.0 Hz, 8H), 3.380-3.317 (m, 16H), 3.101 (s, 24H), 1.841-1.765 (m, 24H), 1.623 (p, J=6.5 Hz, 8H), 1.489 (p, J=7 Hz, 8H), 0.938 (m, 12H). $^{13}$C-NMR (125 MHz, $CD_3OD$) δ 162.011, 140.843, 130.391, 106.505, 102.599, 69.217, 65.665, 65.541, 51.540, 32.522, 30.200, 27.296, 26.825, 23.735, 23.657, 14.485.

The COEs provided below were prepared in a similar manner as those COEs described herein.

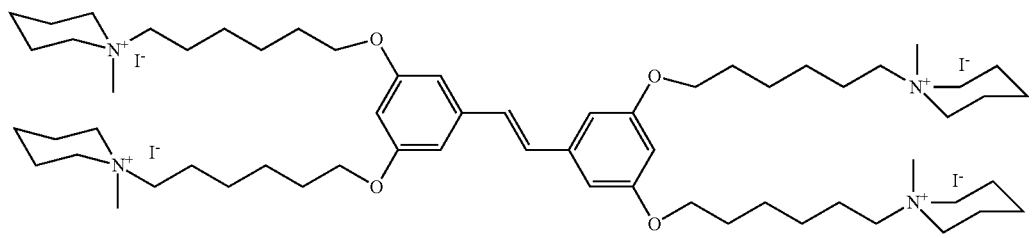 [SMILES: C[N+]1(CCCCCCOc2cc(/C=C/c3cc(OCCCCCC[N+]4(C)CCCCC4)cc(OCCCCCC[N+]4(C)CCCCC4)c3)cc(OCCCCCC[N+]3(C)CCCCC3)c2)CCCCC1 ; [I-] ; [I-] ; [I-] ; [I-]]

Formula N: COE2-2N (50 mg, 0.05 mmol, 1.0 eq.) was dissolved in 1 mL dry DMF and an excess of N-methylpiperidine (0.06 mL, 10 eq.) was added. The resulting solution was stirred under Ar at 45° C. for 2 days. The product was precipitated from the mixture using 20 mL ether. After centrifugation at 7000 rpm for 3 mins, the resulting solid was dried in vacuo for 5 h. Compound 6 was afforded as a white solid (55 mg, 80% yield).

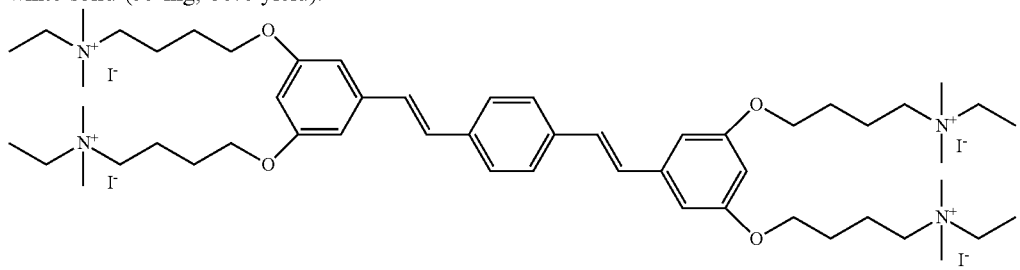

Formula P: 1,4-bis((E)-3,5-bis(4-iodobutoxy)styryl)benzene (20 mg, 0.02 mmol, 1 eq.) was dissolved in 1 mL DMF and a large excess of N,N-dimethylethylamine (0.04 mL, 20 eq.) was added. The resulting solution was stirred under argon at 45° C. for 2 days. The crude product was precipitated from the reaction mixture using 20 mL ether. After centrifugation at 7000 rpm for 3 mins, the resulting solid was dissolved in the minimum amount of deionized water and was purified by reversed phase column chromatography (3:7 MeOH:water). Fractions were combined and lyophilized. The pure product was obtained as a white solid (18 mg, 70% yield).

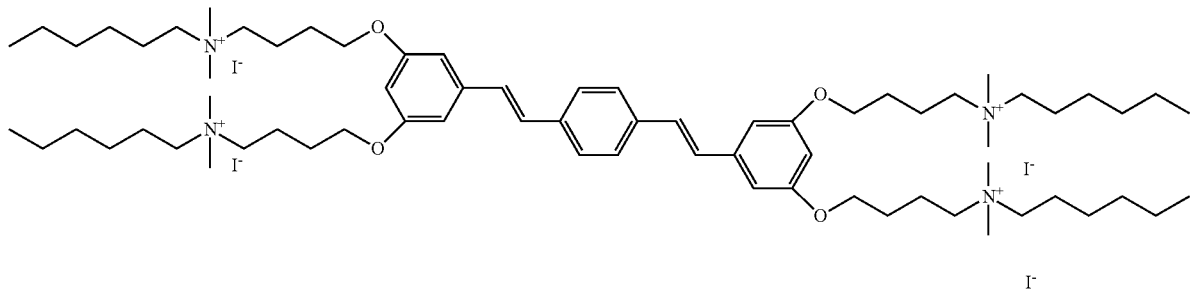 [SMILES: CCCCCC[N+](C)(C)CCCCOc1cc(/C=C/c2ccc(/C=C/c3cc(OCCCC[N+](C)(C)CCCCCC)cc(OCCCC[N+](C)(C)CCCCCC)c3)cc2)cc(OCCCC[N+](C)(C)CCCCCC)c1 ; [I-] ; [I-] ; [I-] ; [I-]]

Formula T: 1,4-bis(€-3,5-bis(4-iodobutoxy)styryl)benzene (51 mg, 0.05 mmol, 1 eq.) was dissolved in 1 mL DMF and an excess of N,N-dimethylhexylamine (0.08 mL, 10 eq.) was added. The resulting solution was stirred under argon at 45° C. for 2 days. The crude product was precipitated from the reaction mixture using 20 mL ether. After centrifugation at 7000 rpm for 3 mins, the resulting solid was purified by reversed phase column chromatography (3:7 MeOH:water). Fractions were combined and lyophilized. The pure product was obtained as a white solid (45 mg, 60% yield).

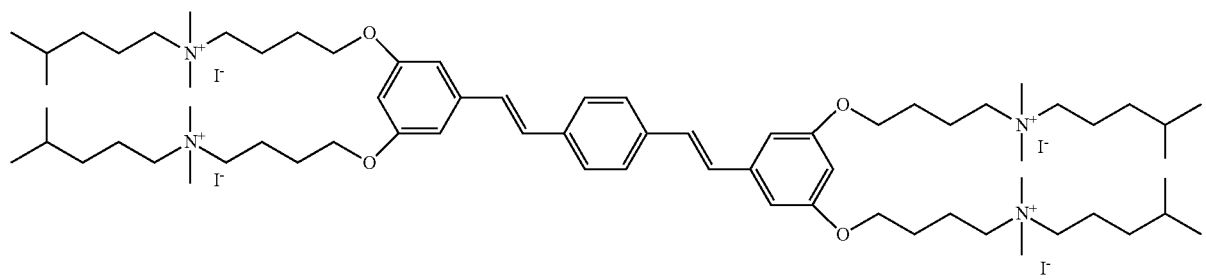 [SMILES: CC(C)CCC[N+](C)(C)CCCCOc1cc(/C=C/c2ccc(/C=C/c3cc(OCCCC[N+](C)(C)CCCC(C)C)cc(OCCCC[N+](C)(C)CCCC(C)C)c3)cc2)cc(OCCCC[N+](C)(C)CCCC(C)C)c1 ; [I-] ; [I-] ; [I-] ; [I-]]

Formula V: 1,4-bis(€-3,5-bis(4-iodobutoxy)styryl)benzene (20 mg, 0.02 mmol, 1 eq.) was dissolved in 1 mL DMF and a large excess of N,N-dimethyl-4-methylpentylamine (0.6 mL) was added. The resulting solution was stirred under argon at 45° C. for 2 days. The crude product was precipitated from the reaction mixture using 20 mL ether. After centrifugation at 7000 rpm for 3 mins, the resulting solid was purified by reversed phase column chromatography (3:7 MeOH:water). Fractions were combined and lyophilized. The pure product was obtained as a white solid (16 mg, 55% yield).

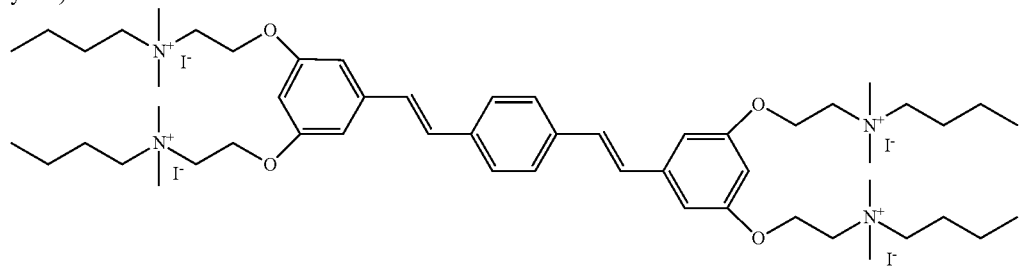

Formula G: 1,4-bis(€-3,5-bis(2-iodoethoxy)styryl)benzene (20 mg, 0.02 mmol, 1 eq.) was suspended in 1 mL DMF and an excess of N,N-dimethylbutylamine (0.03 mL, 10 eq.) was added. The resulting mixture was stirred under argon at 4 5° C. for 3 days. The crude product was precipitated from the reaction mixture using 20 mL ether. After centrifugation at 7000 rpm for 3 mins, the resulting solid was purified by reversed phase column chromatography (3:7 MeOH:water). Fractions were combined and lyophilized. The pure product was obtained as a white solid (18 mg, 65% yield).

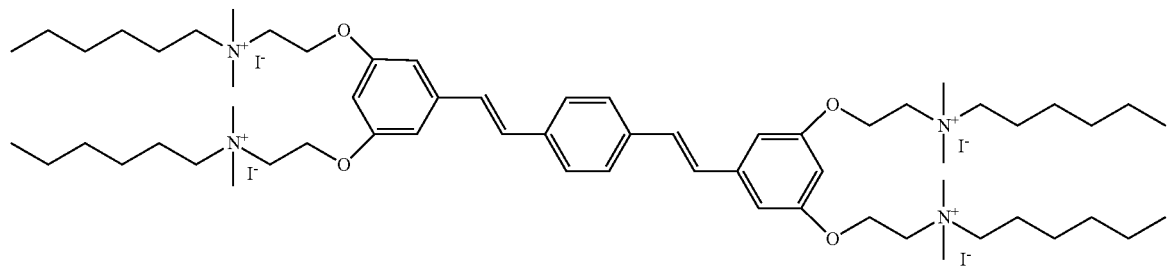 [SMILES: CCCCCC[N+](C)(C)CCOc1cc(/C=C/c2ccc(/C=C/c3cc(OCC[N+](C)(C)CCCCCC)cc(OCC[N+](C)(C)CCCCCC)c3)cc2)cc(OCC[N+](C)(C)CCCCCC)c1 ; [I-] ; [I-] ; [I-] ; [I-]]

Formula H: 1,4-bis((E)-3,5-bis(2-iodoethoxy)styryl)benzene (20 mg, 0.02 mmol, 1 eq.) was suspended in 1 mL DMF and an excess of N,N-dimethylhexylamine (0.04 mL, 10 eq.) was added. The resulting mixture was stirred under argon at 45° C. for 3 days. The crude product was precipitated from the reaction mixture using 20 mL ether. After centrifugation at 7000 rpm for 3 mins, the resulting solid was purified by reversed phase column chromatography (3:7 MeOH:water). Fractions were combined and lyophilized. The pure product was obtained as a white solid (15 mg, 49% yield).

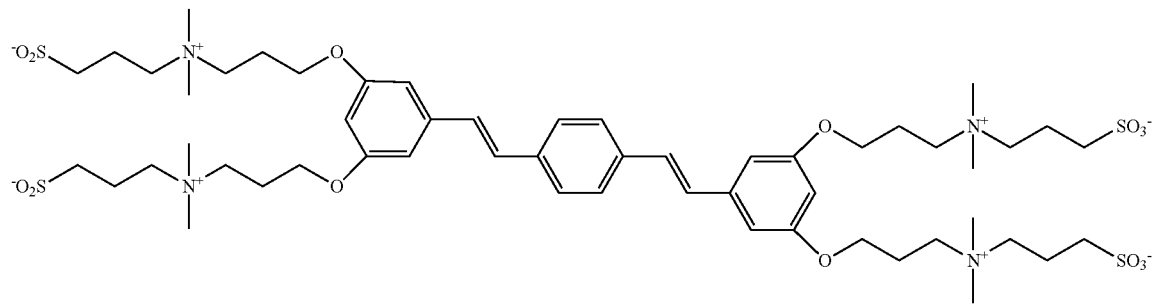

Formula SS: 1,3-propanesultone (500 mg, 4.1 mmol) and anhydrous tetrahydrofuran (20 mL) were added to a flame-dried 100 mL round bottom flask. Dimethylamine (2M in methanol, 20 mL, 40 mmol) was added via syringe. The reaction mixture was left to react at room temperature for 14 hours. The mixture was concentrated to ~25 mL under reduced pressure and added to a centrifuge tube containing 25 mL diethyl ether. The white precipitate was pelleted at 7000 rpm for 3 mins and the supernatant was decanted. After thoroughly drying under vacuum, the white solid 3-(dimethylamino)propane-1-sulfonic acid was used without further purification (620 mg, 91% yield). 1H NMR (500 MHz, Deuterium Oxide) S 3.16 (d, J=7.4 Hz, 2H), 2.88 (t, J=7.2 Hz, 2H), 2.78 (s, 6H), 2.05 (p, J=7.6 Hz, 2H).

1,4-bis((E)-3,5-bis(3-iodopropoxy)styryl)benzene (20 mg, 0.02 mmol), 3-(dimethylamino)propane-1-sulfonic acid (33 mg, 20 mmol), and potassium carbonate (30 mg, 0.22 mmol) were suspended in DMF (0.4 mL) and DMSO (0.4 mL). The reaction mixture was heated to 45° C. for 2 days. Following precipitation in methy tert-butyl ether, the solid was dissolved in 250 mM HCl (2 mL) and loaded onto a 12 g C18 column. The product was eluted with 30% methanol in water containing 100 mM HCl, concentrated under reduced pressure, dissolved in pure water, and lyophilized to obtain a white solid (26 mg, 78% yield).

| Formula | $^1$H NMR (δ) | $^{13}$C NMR (δ) | HRMS (ESI) |
|---|---|---|---|
| Formula G | (DMSO-$d_6$): 7.65 (s, 4H), 7.36 (d, J = 16Hz, 2H), 7.25 (d, J = 16Hz, 2H), 6.95 (s, 4H), 6.56 (s, 2H), 4.51 (t, J = 5 Hz, 8H), 3.79 (t, J = 5 Hz, 8H), 3.41-3.44 (m, 8H), 3.17 (s, 23H), 1.71-1.74 (m, 8H), 1.32-1.36 (m, 8H), 0.94 (t, J = 8 Hz, 12H) | (DMSO-$d_6$): 159.22, 139.96, 136.86, 129.55, 128.59, 127.49, 106.41, 101.95, 64.22, 62.39, 62.23, 51.41, 24.34, 19.72, 14.03 | 556.2526 [M-2I]2+ |
| Formula H | (DMSO-$d_6$): 7.64 (s, 4H), 7.34 (d, J = 17 Hz, 2H), 7.24 (d, J = 17 Hz, 2H), 6.94 (s, 4H), 6.55 (s, 2H), 4.51 (t, J = 5 Hz, 8H), 3.78 (t, J = 5 Hz, 8H), 3.39-3.42 (m, 8H), 3.16 (s, 22H), 1.72-1.75 (m, 8H), 1.29-1.36 (m, 23H), 0.87 (t, J = 7 Hz, 12H) | (DMSO-$d_6$): 158.72, 139.43, 136.35, 129.02, 128.08, 126.97, 105.92, 101.40, 64.09, 61.88, 61.69, 50.89, 30.70, 25.44, 21.88, 21.82, 13.83 | |
| Formula J | (CD$_3$OD): 7.12 (s, 2H), 6.75 (d, J = 2 Hz, 4H), 6.39 (t, J = 2 Hz, 2H), 4.03 (t, J = 7 Hz, 8H), 3.33-3.37 (m, 8H), 3.09 (s, 23H), 1.74-1.87 (m, 25H), 1.59-1.66 (m, 9H), 1.33-1.52 (m, 26H), 0.95 (t, J = 7 Hz, 12H) | (DMSO-$d_6$): 160.46, 139.44, 129.33, 105.45, 101.25, 67.86, 63.46, 63.40, 50.43, 28.93, 28.36, 25.99, 25.53, 22.16, 22.09, 21.89, 14.21 | 645.3850 [M-2I]2+ |
| Formula K | (CD$_3$OD): 7.16 (s, 2H), 6.78 (s, 4H), 6.41 (t, J = 3 Hz, 2H), 4.04 (t, J = 6 Hz, 8H), 3.35-3.38 (m, 8H), 3.10 (s, 24H), 1.72-1.87 (25H), 1.60-1.66 (m, 8H), 1.41-1.52 (m, 17H), 1.02 (t, J = 8 Hz, 12H) | (DMSO-$d_6$): 159.99, 138.94, 128.87, 104.96, 100.72, 67.37, 62.92, 62.81, 49.97, 28.50, 25.55, 25.08, 23.70, 21.68, 19.19, 13.49 | 617.3544 [M-2I]2+ |
| Formula L | (CD$_3$OD): 7.15 (s, 2H), 6.78 (d, 2 Hz, 4H), 6.41 (t, J = 2 Hz, 2H), 4.05 (t, J = 6 Hz, 8H), 3.37-3.40 (m, 8H), 3.12 (s, 24H), 1.75-1.88 (m, 26H), 1.61-1.70 (m, 13H), 1.48-1.54 (m, 9H), 0.96 (d, J = 7 Hz, 23H) | (CD$_3$OD): 161.88, 140.72, 130.22, 106.31, 102.31, 68.94, 65.70, 65.43, 51.30, 36.32, 30.07, 28.87, 27.06, 26.70, 23.57, 22.81, 21.63 | 673.4156 [M-2I]2+ |
| Formula M | (DMSO-$d_6$): 7.19 (s, 2H), 6.76 (d, J = 3 Hz, 4H), 6.39 (s, 2H), 3.98 (t, J = 7 Hz, 8H), 3.25-3.29 (m, 17H), 3.01 (s, 24H), 1.73-1.76 (m, 8H), 1.67-1.70 (m, 9H), 1.53-1.60 (m, 13H), 1.46-1.51 (m, 9H), 1.33-1.38 (m, 9H), 0.92 (d, J = 6 Hz, 24H) | (DMSO-$d_6$): 159.99, 138.94, 128.86, 104.96, 100.72, 67.37, 62.76, 61.87, 49.95, 30.03, 28.49, 25.69, 25.54, 25.08, 22.18, 21.67 | 645.3860 [M-2I]2+ |
| Formula N | (CD$_3$OD): 7.06 (s, 2H), 6.68 (s, 4H), 6.32 (s, 2H), 3.96 (t, J = 7 Hz, 8H), 3.23 (s, 12H), 3.00 (s, 12H), 1.71-1.83 (m, 31H), 1.59-1.67 (m, 9H), 1.51-1.58 (m, 8H), 1.39-1.45 (m, 8H) | (DMSO-$d_6$): 160.02, 139.98, 128.89, 105.00, 100.78, 67.40, 62.32, 59.99, 48.59, 48.46, 47.10, 47.08, 28.50, 25.63, 25.11, 20.95, 20.69, 19.30 | 613.3238 [M-2I]2+ |
| Formula P | (DMSO-$d_6$): 7.61 (s, 4H), 7.29 (d, J = 16 Hz, 2H), 7.20 (d, J = 16 Hz, 2H), 6.82 (s, 4H), 6.46 (s, 2H), 4.06 (t, J = 6 Hz, 8H), 3.34-3.39 (m, 15H), 3.02 (s, 23H), 1.81-1.87 (m, 8H), 1.74-1.79 (m, 8H), 1.24 (t, J = 7 Hz, 12H) | (DMSO-$d_6$): 159.81, 139.13, 136.36, 128.56, 128.36, 126.91, 105.19, 100.96, 66.83, 62.00, 58.61, 49.50, 25.62, 18.80, 7.86 | 556.2526 [M-2I]2+ |
| Formula Q | (DMSO-$d_6$): 7.62 (s, 4H), 7.30 (d, J = 17 Hz, 2H), 7.21 (d, J = 17 Hz, 2H), 6.83 (s, 4H), 6.45 (t, J = 3 Hz, 2H), 4.06 (t, J = 7 Hz, 8H), 3.36-3.39 (m, 8H), 3.24-3.27 (m, 8H), | (DMSO-$d_6$): 167.02, 145.12, 142.17, 133.91, 133.67, 132.16, 109.16, 104.67, 68.47, 65.94, 64.09, 50.71, | |

| Formula | ¹H NMR (δ) | ¹³C NMR (δ) | HRMS (ESI) |
|---|---|---|---|
| | 1.82-1.88 (m, 8H), 1.76-1.70 (m, 8H), 1.66-1.75 (m, 8H), 0.89 (t, J = 7 Hz, 12H) | 24.75, 17.59, 13.98, 8.77 | |
| Formula R | (CD₃OD): 7.58 (s, 4H), 7.20 (d, J = 17 Hz, 2H), 7.13 (d, J = 17 Hz, 2H), 6.79 (t, J = 2 Hz, 4H), 6.51 (s, 2H), 4.12 (t, J = 6 Hz, 8H), 3.44-3.47 (m, 8H), 3.34-3.38 (m, 8H), 1.98-2.04 (m, 8H), 1.88-1.92 (m, 10H), 1.73-1.79 (m, 8H), 1.38-1.44 (m, 10H), 0.99 (t, J = 8 Hz, 12H) | (DMSO-d₆): 159.81, 139.13, 136.36, 127.01, 126.80, 105.31, 105.30, 105.06, 101.06, 66.76, 62.84, 62.50, 50.03, 25.58, 23.71, 19.20, 18.82, 13.53 | 612.3157 [M-2I]2+ |
| Formula S | (DMSO-d₆): 7.61 (s, 4H), 7.28 (d, J = 17 Hz, 2H), 7.20 (d, J = 16 Hz, 2H), 6.82 (s, 4H), 6.45 (s, 2H), 4.06 (t, J = 6 Hz, 8H), 3.35-3.37 (m, 8H), 3.26-3.27 (m, 8H), 3.04 (s, 23H), 1.82-1.84 (m, 8H), 1.76-1.77 (m, 8H), 1.66-1.69 (m, 8H), 1.32-1.35 (m, 8H), 1.23-1.28 (m, 8H), 0.88 (t, J = 6 Hz, 12H) | (DMSO-d₆): 159.80, 139.11, 136.35, 128.54, 128.35, 126.88, 105.18, 100.91, 66.73, 63.00, 62.48, 50.05, 27.90, 25.57, 21.62, 21.40, 18.81, 13.73 | 640.3456 [M-2I]2+ |
| Formula T | (CD₃OD): 7.58 (s, 4H), 7.21 (d, J = 17 Hz, 2H), 7.14 (d, J = 17 Hz, 2H), 6.80 (s, 4H), 6.52 (s, 2H), 4.13 (t, J = 6 Hz, 8H), 3.45-3.48 (m, 8H), 3.35-3.37 (m, 8H), 3.14 (s, 23H), 1.99-2.04 (m, 8H), 1.90-1.94 (m, 8H), 1.76-1.80 (m, 8H), 1.34-1.41 (m, 24H), 0.91 (t, J = 7 Hz, 12H) | (CD₃OD): 161.64, 141.01, 138.15, 129.91, 129.61, 128.03, 106.57, 102.15, 68.18, 65.42, 64.83, 51.48, 32.41, 27.10, 23.60, 23.53, 20.66, 14.31 | 668.3784 [M-2I]2+ |
| Formula U | (DMSO-d₆): 7.61 (s, 4H), 7.27 (d, J = 17 Hz, 2H), 7.19 (d, J = 16 Hz, 2H), 6.81 (d, J = 2 Hz, 4H), 6.45 (t, J = 2 Hz, 2H), 4.05 (t, J = 6 Hz, 8H), 3.33-3.37 (m, 8H), 3.03 (s, 23H), 1.81-1.85 (m, 8H), 1.75-1.79 (m, 12H), 0.92 (d, J = 6 Hz, 23H) | | 640.3465 [M-2I]2+ |
| Formula V | (DMSO-d₆): 7.61 (s, 4H), 7.28 (d, J = 16 Hz, 2H), 7.19 (d, J = 16 Hz, 2H), 6.81 (s, 4H), 6.44 (s, 2H), 4.05 (t, J = 6 Hz, 8H), 3.35-3.39 (m, 8H), 3.24-3.27 (m, 8H), 3.04 (m, 22H), 1.81-1.87 (m, 8H), 1.73-1.79 (m, 8H), 1.63-1.70 (m, 8H), 1.53-1.61 (m, 5H), 1.13-1.17 (m, 8H), 0.88 (d, J = 7 Hz, 23H) | (DMSO-d₆): 159.81, 139.12, 136.36, 128.55, 128.54, 126.90, 105.18, 100.92, 66.76, 63.21, 62.54, 50.03, 34.76, 27.07, 25.99, 22.30, 19.73, 18.85 | 668.3784 [M-2I]2+ |
| Formula W | (DMSO-d₆): 7.62 (s, 4H), 7.29 (d, J = 17 Hz, 2H), 7.20 (d, J = 16 Hz, 2H), 6.82 (d, J = 2 Hz, 4H), 6.46 (t, J = 2 Hz, 2H), 4.06 (t, J = 6 Hz, 8H), 3.41-3.44 (m, 8H), 3.33-3.36 (m, 16H), 3.03 (s, 12H), 1.77-1.91 (m, 33H), 1.50-1.60 (m, 8H) | (DMSO-d₆): 159.83, 139.13, 136.36, 128.56, 128.37, 126.91, 105.20, 100.96, 66.88, 61.92, 60.03, 47.17, 25.72, 20.68, 19.27, 18.12 | 608.2842 [M-2I]2+ |
| Formula X | (DMSO-d₆): 7.63 (s, 4H), 7.28 (dd, J = 30.9, 15.9 Hz, 4H), 6.85 (s, 4H), 6.48 (s, 2H), 4.11 (t, J = 6.0 Hz, 8H), 3.56 – 3.50 (m, 8H), 3.14 (s, 36H), 2.20 (dq, J = 11.9, 6.0 Hz, 8H) | (DMSO-d₆): 160.02, 139.75, 136.82, 129.23, 128.72, 127.43, 105.98, 101.56, 65.37, 63.47, 63.45, 63.43, 52.87, 52.84, 52.82, 40.41, 40.27, 40.13, 39.99, 39.85, 39.71, 39.57, 23.09 | 500.1905 [M-2I]2+ |
| Formula Y | (DMSO-d₆): 7.63 (s, 4H), 7.28 (dd, J = 30.0, 16.4 Hz, 4H), 6.85 (s, 4H), 6.47 (t, J = 2.2 Hz, 1H), 4.12(t J = 6.0 Hz, 8H), 3.52 –3.44 (m, 8H), 3.42 (q, J = 7.2 Hz, 8H), 3.07 (s, 24H), 2.21 – 2.13 (m, 8H), 1.28 (t, J = 7.2 Hz, 13H) | (DMSO-d₆): 160.01, 139.75, 136.83, 129.22, 128.73, 127.43, 105.98, 101.58, 65.33, 60.38, 59.11, 50.16, 40.43, 40.29, 40.15, 40.01, 39.87, 39.73, 39.59, 22.68, 8.36 | 528.2213 [M-2I]2+ |
| Formula Z | (DMSO-d₆): 7.63 (s, 4H), 7.30 (d, J = 17 Hz, 2H), 7.22 (d, J = 17 Hz, 2H), 6.85 (d, J = 2 Hz, 4H), 6.47 (t, J = 2 Hz, 2H), 4.10 (t, J = 6 Hz, 8H), 3.48-3.51 (m, 8H), 3.29-3.31 (m, 8H), 3.09 (s, 22H), 2.15-2.21 (m, 8H), 1.68-1.75 (m, 8H), 0.91 (t, J = 7 Hz, 12H) | (DMSO-d₆): 159.50, 139.25, 136.33, 128.72, 128.22, 126.93, 105.50, 101.12, 64.85, 64.41, 60.55, 50.21, 22.22, 15.41, 10.46 | 556.2536 [M-2I]2+ |
| Formula AA | (DMSO-d₆): 7.63 (s, 4H), 7.27 (dd, J = 26.7, 16.3 Hz, 4H), 6.85 (d, J = 2.3 Hz, 4H), 6.47 (d, J = 1.7 Hz, 4H), 4.11 (t, J = 6.0 Hz, 8H), 3.53 –3.44 (m, 8H), 3.09 (s, 24H), 2.24 – 2.11 (m, 8H), 1.72 –1.64 (m, 8H), 1.33 (h, J = 7.4 Hz, 8H), 0.95 (t, J = 7.4 Hz, 12H) | (DMSO-d₆): 159.98, 139.75, 136.83, 129.22, 128.73, 127.43, 105.98, 101.61, 65.31, 63.34, 60.91, 50.72, 40.42, 40.28, 40.14, 40.00, 39.86, 39.72, 39.59, 24.19, 22.71, 19.63, 14.05, 13.98 | 584.2831 [M-2I]2+ |
| Formula BB | (DMSO-d₆): 7.63 (s, 4H), 7.27 (dd, J = 28.2, 16.5 Hz, 4H), 6.85 (d, J = 2.1 Hz, 4H), 6.47 (t, J = 2.1 Hz, 2H), 4.11 (t, J = 5.9 Hz, 8H), 3.51 –3.45 (m, 8H), 3.09 (s, 24H), 2.22 – 2.13 (m, 8H), 1.73 –1.64 (m, 8H), 1.32 –1.27 (m, 24H), 0.88 (t, J = 6.7 Hz, 8H) | (DMSO-d₆): 159.98, 139.76, 136.82, 129.21, 128.73, 127.41, 105.98, 101.61, 65.29, 63.50, 60.86, 50.72, 40.42, 40.28, 40.15, 40.01, 39.87, 39.73, 39.59, 31.12, 25.86, 22.70, 22.34, 22.14, 14.29 | 640.3469 [M-2I]2+ |
| Formula CC | (DMSO-d₆): 7.59 (s, 4H), 7.22 (dd, J = 33.5, 15.8 Hz, 4H), 6.75 (s, 4H), 6.37 (s, 2H), 3.97 (t, J = 6.4 Hz, 8H), 3.30 – 3.23 (m, 8H), 3.03 (s, 36H), 1.76 – 1.58 (m, 16H), 1.48 – 1.19 (m, 32H). | (DMSO-d₆): 160.52, 139.52, 136.85, 128.91, 127.34, 105.42, 101.17, 67.96, 65.77, 52.66, 52.64, 52.61, 40.42, 40.28, 40.14, 40.00, 39.87, 39.73, 39.59, 29.16, 29.01, 28.92, 26.17, 25.92, 22.49 | |
| Formula DD | (DMSO-d₆): 7.64 (s, 4H), 7.39 – 7.19 (m, 4H), 6.88 (d, J = 2.2 Hz, 4H), 6.49 | (DMSO-d₆): 159.93, 139.78, 136.83, 129.30, 128.68, | 551.0976 [M-3I]3+ |

| Formula | ¹H NMR (δ) | ¹³C NMR (δ) | HRMS (ESI) |
|---|---|---|---|
| | (t, J = 2.1 Hz, 2H), 4.15 (t, J = 5.9 Hz, 8H), 4.02 – 3.92 (m, 48H), 3.82 – 3.76 (m, 8H), 3.33 (s, 12H), 2.28 – 2.22 (m, 8H) | 127.45, 106.06, 101.64, 65.12, 61.63, 52.90, 51.94, 50.96, 40.43, 40.29, 40.15, 40.01, 39.87, 39.73, 39.59, 22.38 | |
| Formula EE | (DMSO-d₆): 7.64 (s, 4H), 7.36 (d, J = 16 Hz, 2H), 7.25 (d, J = 16 Hz, 2H), 6.96 (d, J = 2 Hz, 4H), 6.60 (t, J = 2 Hz, 2H), 4.52 (t, J = 5 Hz, 8H), 3.82 (t, J = 5 Hz, 8H), 3.22 (s, 37H) | (DMSO-d₆): 158.71, 139.41, 136.36, 129.01, 128.07, 126.96, 106.04, 101.53, 64.87, 64.04, 53.23 | 472.1596 [M-2I]2+ |
| Formula FF | (DMSO-d₆): 7.60 (s, 1H), 7.23 (dd, J = 32.2, 16.3 Hz, 2H), 6.75 (s, 1H), 6.37 (s, 1H), 3.97 (t, J = 6.3 Hz, 3H), 3.31 – 3.15 (m, 3H), 3.03 (s, 9H), 1.90 –1.54 (m, 7H), 1.49 – 1.37 (m, 3H), 1.34 – 1.20 (m, 13H) | (DMSO-d₆): 160.51, 139.50, 136.83, 128.89, 127.35, 105.41, 101.14, 67.97, 65.81, 52.64, 29.38, 29.24, 29.22, 29.19, 28.95, 26.18, 26.01, 22.50 | |
| Formula GG | (CD₃OD): 7.64 (s, 4H), 7.33 – 7.17 (m, 4H), 6.85 (d, J = 2.3 Hz, 4H), 6.53 (s, 2H), 4.14 (t, J = 6.1 Hz, 8H), 3.93 – 3.87 (m, 8H), 3.62 (m, 16H), 3.56 – 3.47 (m, 16H), 3.44 – 3.37 (m, 8H), 3.38 – 3.30 (m, 12H), 3.14 (s, 12H), 2.03 – 1.94 (m, 8H), 1.93 – 1.84 (m, 8H), 1.79 – 1.69 (m, 8H), 1.40 (h, J = 7.4 Hz, 8H), 1.00 (t, J = 7.8 Hz, 12H) | (CD₃OD): 160.28, 139.60, 136.80, 128.58, 128.35, 126.85, 125.59, 105.29, 101.06, 71.44, 69.98, 66.99, 64.28, 62.56, 62.12, 60.90, 57.84, 48.48, 48.14, 47.97, 47.80, 47.63, 47.46, 47.29, 47.28, 47.11, 25.72, 23.98, 19.36, 19.08, 12.70 | |
| Formula HH | (CD₃OD): 7.64 (d, J = 3.5 Hz, 1H), 7.20 (d, J = 16.3 Hz, OH), 6.85 (d, J = 2.2 Hz, 1H), 4.14 (t, J = 6.1 Hz, 2H), 3.90 (t, J = 4.5 Hz, 2H), 3.62 (ddd, J = 17.3, 6.2, 3.6 Hz, 4H), 3.56 – 3.47 (m, 3H), 3.51 (s, 1H), 3.44 – 3.38 (m, 2H), 3.35 (t, J = 1.4 Hz, 3H), 3.14 (s, 2H), 1.99 (p, J = 7.4 Hz, 2H), 1.88 (p, J = 7.0, 6.5 Hz, 2H), 1.74 (p, J = 7.5 Hz, 2H), 1.40 (q, J = 7.4 Hz, 2H), 1.03 – 0.96 (m, 3H). | (CD₃OD): 160.28, 139.61, 136.80, 128.59, 128.35, 126.86, 125.59, 105.30, 101.07, 71.44, 69.98, 67.00, 64.28, 62.56, 62.12, 60.90, 57.84, 48.48, 25.72, 23.98, 19.36, 19.08, 12.70 | |
| Formula MM | (CD₃OD): 7.55 (s, 4H), 7.19 – 7.08 (m, 4H), 6.73 (s, 5H), 6.41 (s, 2H), 4.05 (t, J = 5.9 Hz, 8H), 3.28 (t, J = 6.9 Hz, 8H), 1.91 – 1.75 (m, 16H) | | |
| Formula NN | (DMSO-d₆): 7.63 (s, 4H), 7.27 (dd, J = 28.1, 16.4 Hz, 4H), 6.85 (d, J = 2.2 Hz, 4H), 6.47 (t, J = 2.2 Hz, 2H), 4.80 (s, 4H), 4.11 (t, J = 5.9 Hz, 8H), 3.54 – 3.47 (m, 1H), 3.44 – 3.38 (m, 9H), 3.10 (s,24 H), 2.18 (dq, J = 11.8, 6.0 Hz, 8H),1.91 – 1.83 (m, 9H) | (DMSO-d₆): 160.02, 139.74, 136.83, 129.22, 128.73, 127.43, 105.97, 101.57, 65.32, 61.71, 60.91, 58.07, 50.85, 40.42, 40.28, 40.14, 40.00, 39.86, 39.72, 39.58, 25.79, 22.71 | |
| Formula OO | (DMSO-d₆): 7.61 (s, 4H), 7.25 (dd, J = 31.4, 15.2 Hz, 4H), 6.83 (d, J = 2.2 Hz, 4H), 6.44 (t, J = 2.1 Hz, 2H), 5.36 (d, J = 5.1 Hz, 4H), 4.99 (t, J = 5.4 Hz, 4H), 4.07 (qq, J = 10.6, 5.8 Hz, 12H), 3.58 (t, J = 8.3 Hz, 8H), 3.48 – 3.40 (m, 8H), 3.36 – 3.31 (m, 4H), 3.29 – 3.22 (m, 4H), 3.16 (s, 24H), 2.27 – 2.12 (m, 8H) | (DMSO-d₆): 160.04, 139.73, 136.83, 129.21, 128.74, 127.42, 105.93, 101.52, 66.65, 66.49, 65.42, 64.18, 62.22, 51.96, 51.91, 40.42, 40.28, 40.14, 40.00, 39.86, 39.72, 39.58, 22.85 | |
| Formula PP | (DMSO-d6): 8.65 (s, 12H), 7.62 (s, 4H), 7.39 – 7.12 (m, 4H), 6.85 (s, 4H), 6.51 (s, 2H), 4.11 (s, 8H), 3.69 '3.43 (m, 16H), 3.13 (s, 24H), 2.95 – 2.81 (m, 8H), 2.28 – 2.05 (m, 16H) | (DMSO-d6): 160.02, 139.72, 136.84, 129.26, 128.71, 127.142, 106.08, 101.69, 101.69, 65.143, 61.58, 60.68, 50.75, 40.41, 40.27, 40.14, 40.00, 39.86, 39.72, 39.58, 36.44, 22.73, 20.76 | |
| Formula QQ | (DMSO-d₆): 7.64 (s, 4H), 7.29 (dd, J = 41.7, 16.3 Hz, 4H), 6.87 (d, J = 2.2 Hz, 4H), 6.51 (s, 2H), 4.5 (t, J = 6.0 Hz, 8H), 3.65 – 3.58 (m, 8H), 3.43 – 3.36 (m, 16H), 3.18 (s, 24H), 3.17 (s, 36H), 2.36 – 2.17 (m, 16H) | (DMSO-d₆): 160.01, 139.76, 136.83, 129.26, 128.67, 127.44, 106.02, 101.64, 65.35, 62.30, 61.57, 60.12, 53.14, 50.98, 40.43, 40.29, 40.15, 40.01, 39.87, 39.73, 39.59, 22.77, 17.56 | |
| Formula RR | (DMSO-d₆): 7.64 (s, 4H), 7.32-7.36 (m, 2H), 7.22-7.29 (m, 2H), 6.81-6.85 (m, 4H), 6.43-6.48 (m, 2H), 4.09 (t, J = 7 Hz, 8H), 3.89-3.92 (m, 16H), 3.51-3.53 (m, 8H), 3.37-3.40 (m, 8H), 3.16-3.19 (m, 49H), 1.93-1.95 (m, 8H), 1.72-1.81 (m, 18H), 1.30-1.32 (m, 25H), 0.87 (t, J = 7 Hz, 12H) | | |
| Formula SS | (DMSO-d₆): 7.61 (s, 2H), 7.31 (d, J = 16.3 Hz, 1H), 7.20 (d, J = 16.3 Hz, 1H), 6.83 (d, J = 2.1 Hz, 2H), 6.53 (d, J = 2.0 Hz, 1H), 4.09 (t, J = 5.9 Hz, 4H), 3.48 (dt, J = 12.4, 6.5 Hz, 8H), 3.16 (s, 2H), 3.08 (s, 12H), 2.52 (d, J = 6.9 Hz, 3H), 2.17 (dt, J = 11.4, 5.0 Hz, 4H), 2.08 – 1.98 (m, 4H) | (DMSO-d₆): 160.04, 139.70, 136.85, 128.71, 127.43, 106.03, 102.68, 65.25, 62.50, 60.60, 50.85, 49.05, 48.13, 40.46, 40.30, 40.13, 39.96, 39.79, 39.63, 39.46, 22.67, 19.34 | |
| Formula WW | (DMSO-d₆): 7.66 –7.56 (m, 6H), 7.39 (t, J = 7.6 Hz, 2H), 7.31 – 7.26 (m, 3H), 7.24 – 7.19 (m, 2H), 6.96 – 6.90 (m, 2H), 4.04 (t, J = 6.6 Hz, 4H), 3.89 | | |

-continued

| Formula | $^1$H NMR (δ) | $^{13}$C NMR (δ) | HRMS (ESI) |
|---|---|---|---|
| Formula XX | (DMSO-d$_6$): 7.59 (s, 4H), 7.21 (s, 4H), 6.92 (s, 4H), 4.03 (t, J = 6.5 Hz, 8H), 3.88 (t, J = 6.3 Hz, 4H), 3.37 – 3.27 (m, 12H), 3.07 (s, 54H), 1.82 – 1.62 (m, 24H), 1.56 – 1.46 (m, 12H), 1.41 – 1.27 (m, 12H) (t, J = 6.2 Hz, 2H), 3.35 – 3.28 (m, 6H), 3.07 (s, 27H), 1.83 – 1.63 (m, 12H), 1.58 – 1.46 (m, 6H), 1.43 – 1.29 (m, 6H) | | 869.3442 [M-2I]2+ |

MIC Determination

The minimum inhibitory concentration (MIC) was determined according to the Clinical and Laboratory Standards Institute (CLSI) guidelines by broth dilution. For determination of MIC in alternative media conditions, bacteria were obtained from over-night culture (Staphylococci and Gram-negative bacteria) or after a 4 h incubation period (*S. pneumoniae*) in specified medium and diluted into same medium containing 2-fold serial dilutions of antibiotics. MIC values were derived after 20 h incubation, and were the result of at least 6 independent determinations. Table 1 shows the results from the MIC experiments determined by using different COEs. The MIC study included Gram-negative strains *Salmonella enterica Typhimurium* (ST) ATCC 14028, *E. coli* (EC) ATCC 25922, *Pseudomonas aeruginosa* (PA) ATCC 10145, and *Klebsiella pneumoniae* (KPN) ATCC 13883. Also examined were Gram-positive methicillin-resistant *S. aureus* (MRSA) USA300, MT3302, MT3315 and methicillin-sensitive *S. aureus* Newman, and MT3305. The determined MICs of DSSN and DSBN were consistent with previous studies.

Biocompatibility Experiment

The murine macrophage cell line RAW 264.7 was grown in DMEM supplemented with L-glutamine and 10% heat-inactivated fetal bovine serum in 5% CO$_2$ at 37° C. in 75 cm$^2$ tissue culture flasks. Cells were harvested using a sterile disposable cell scraper and plated at a density of 1 to 2×10$^5$ cells/mL in 2 mL culture medium in 24-well dishes and grown for 24 h to approximately 90% confluence (2 to 4×10$^5$ cells/well). Media was removed and cells were washed with PBS. Drug was added at indicated concentrations in 1 mL volume of cell culture medium and cells were incubated for 18 h bin 5% CO$_2$ at 37° C. Media was then removed, cells were washed with PBS, and cells were harvested using a sterile disposable cell scraper, diluted in trypan blue dye, and counted using a hemacytometer. The results are shown in Table 2.

TABLE 1

Summary of COE MIC consensus values (μg/mL) (n = 6-18).

| | Formula | | | | | | | | |
|---|---|---|---|---|---|---|---|---|---|
| Strain | VV | UU | E | A | C | D | O | F | B |
| ST ATCC 14028 | >256 | 64 | 2 | 64 | 8 | ≥16 | 8 | 4 | 8 |
| EC ATCC 25922 | 256 | 64 | 2 | 32 | 8 | ≥16 | 8 | 8 | 4 |
| PA ATCC 10145 | >256 | >256 | 4 | 256 | 128 | ≥16 | 256 | 256 | 64 |
| KPN ATCC 13883 | 256 | 64 | 2 | 64 | 16 | ≥16 | 32 | 16 | 8 |
| MRSA USA300 | 2 | 1 | 1 | 4 | 0.5 | ≥16 | 0.5 | 2 | 0.5 |
| MSSA Newman | 2 | 1 | 1 | 4 | 1 | ≥16 | 1 | 2 | 0.5 |
| MRSA MT3302 | 2 | 1 | 1 | 4 | 1 | ≥16 | 0.5 | 4 | 0.5 |
| MRSA MT3315 | 2 | 2 | 1 | 4 | 2 | ≥16 | 1 | 4 | 0.5 |
| MSSA MT3305 | 2 | 2 | 1 | 4 | 0.5 | ≥16 | 0.5 | 4 | 0.5 |

TABLE 2

Percent of viable cells left after treatment of COEs in RAW264.7 murine macrophages.

| | Formula | | | | | | | | |
|---|---|---|---|---|---|---|---|---|---|
| [COE] | VV | UU | E | A | C | D | O | F | B |
| 4 μg/mL | 39% | 98% | 99% | 86% | 91% | 87% | 93% | 91% | 87% |
| 10 μg/mL | — | — | — | — | — | 62% | — | — | — |
| 40 μg/mL | <1.4% | <1.4% | 19% | 19% | 18% | — | 19% | 17% | 16% |

Minimum Inhibitor Concentration (MC) Experimental Protocol

Compounds described herein were evaluated for growth inhibition against a variety of bacterial species, including strains that have developed resistance to common antibacterial treatments, according to the procedure described herein, or by analogous procedures known to those skilled in the art. Resistant bacterial strains used for compound testing include methicillin-resistant *S. aureus* (MRSA), vancomycin resistant Enterococci (VRE) and various multi-drug resistant (MDR) strains commonly associated with hospital-acquired (nosocomial) infections, including, but not limited to *A. baumannii, K. pnuemoniae*, and *E. cloacae*. The results of this paragraph following the procedure described herein is provided in Tables 5a-5d.

The minimum inhibitory concentration (MIC) was determined according to the Clinical and Laboratory Standards Institute (CLSI) guidelines by broth dilution. Briefly, determination of MIC in alternative media conditions, bacteria were obtained from over-night culture (Staphylococci and Gram-negative bacteria) or after a 4 h incubation period (*S.*

*pneumoniae*) in specified medium and diluted into same medium containing 2-fold serial dilutions of antibiotics. MIC values were derived after 20 h incubation, and were the result of at least 6 independent determinations. The results of this paragraph following the procedure described herein is provided in Table 4.

Bacteria Culture Conditions:

*E. coli* K12 (ATCC 47076) and *K. aerogenes* (ATCC 13048) were cultured in LB medium at 37° C. and harvested at mid-log growth (~5 h). *S. epidermidis* (ATCC 14990) was cultured in BHI medium at 37° C. overnight before use. All bacteria were plated on agar and used for no more than 1 month to maintain activity. Freezer-stock samples were preserved at −80° C. with 20% glycerin. The results with the bacteria of the paragraph following the procedure described herein is provided in Table 3.

MIC Broth Microdilution Method:

1. Inoculate bacteria from a single colony on the agar plate in culture media at 37° C.
2. Measure $OD_{600}$ of the media and bacteria suspension.
3. Assume 1 $OD_{600}$ of bacteria in LB≈$3.65 \times 10^8$ cells/mL. Based on the measurement of OD value, dilute bacteria suspension to a concentration of $1 \times 10^6$ cells/mL. (This results in a final test concentration of $5 \times 10^5$ cfu/mL)
4. In a sterile 96-well plate, add 50 μL of culture media to columns 1-11 and 100 μL of the culture media to column 12.
5. Add 50 μL of COE solution (4× highest test concentration) to column 1. Mix thoroughly.
6. Pipette 50 μL of the resulting solutions to the next column and mix thoroughly by pipetting solutions up and down several times. Repeat until reaching column 10. Discard 50 μL of the solution in column 10. (At this point, columns 1-10 should have 50 μL of culture media solution containing the test article, column 11 should have 50 μL of culture media without the test article, and column 12 should have 100 μL of culture media without the test article)
7. Add 50 μL of diluted *E. coli* suspension (from step 3) to the wells in column 1-11.
8. Incubate the plate at 37° C. with 200 rpm shaking overnight
9. The MIC was determined by measured absorbance at 600 nm. Column 11 is used as the control (bacteria without test article) and column 12 is the blank (no bacteria or test article). The lowest concentration that was found to show less than 10% relative growth was determined as MIC.

Cell Viability Experimental Protocol—Cytotoxicity

Further cytotoxicity studies were run as described below utilizing a different method, and the results are shown in Table 6.

Mammalian Cell Culture Conditions:

Before removing the frozen cell stocks from liquid nitrogen, culture medium was pre-warmed to 37° C. The frozen tube was then removed from liquid nitrogen and placed into a 37° C. water bath and shaken gently to thaw the cell stock as quickly as possible. A small portion of the pre-warmed culture medium was added to the cell solution. The cell suspension was then centrifuged at 1000 r/min for 3 minutes. The supernatant was discarded and the cells were resuspended in fresh culture medium.

NIH 3T3 (ATCC CRL-1658) and Hep G2 (ATCC HB-8065) cells were cultured with DMEM+10% FBS in 100 mm dishes. Cells were lifted for subculture or testing when confluence reached ~60% by treating with 1× trypsin (incubated for 3 min at 37° C.). J774 (ATCC TIB-67) cells were cultured with DMEM+10% FBS in 100 mm dishes. Cells were lifted for subculture or testing when confluence reached ~80% using a cell scraper. RAW264.7 (ATCC TIB-71) cells were cultured with DMEM+10% heat-inactivated FBS+1% pen/strep in T75 flasks. Cells were lifted for subculture or testing when confluence reached ~80% using a cell scraper.

MTT Assay Method:

1. Cells were lifted and resuspended in culture medium. The number of cells in the cell suspension was determined using an auto-cell counter: 10 μL of the cell suspension was mixed with 10 μL 1× trypan blue (filtered with 0.2 μm PES filter) and the mixture was loaded onto a cell counting slide. Based on the concentration of viable cells, the cell suspension was further diluted to achieve the desired density.
2. Cells were seeded in 96 well plates by adding 100 μL final cell suspension column-by-column using a multichannel pipette (5000 cells/well for NIH 3T3, 10000 cells/well for Hep G2, J774 and RAW264.7). The outer wells were block with PBS to reduce the effects of evaporation. One column was filled with only culture medium as a blank. Cells were incubated overnight before adding the test articles.
3. Test articles were dissolved in 1×PBS (or DMSO) to obtain stocks solution. Stock solutions were pre-warmed before use. Concentrated stock solutions were diluted to achieve 10× stocks of highest drug concentration (e.g., 1.28 mg/mL where 128 μg/mL is the desired highest test concentration). Serial dilutions (2-fold) of the 10× solutions were made in sterile culture tubes by diluting in 1×PBS (8 dilutions to yield 9 test concentrations). 900 μL of culture media was added to each tube to obtain final drug solution containing 10% PBS (or less than 1% DMSO) for each experimental group.
4. The original culture medium was gently removed from the 96-well plates using a pipette. 100 μL of the test article solutions prepared in Step 3 were added to rows 2-7 of each column to obtain six replicates for each concentration. Plates were then incubated for 24 hours.
5. MTT solutions were prepared by dissolving commercial MTT powder in 1×PBS to a concentration of 5 mg/mL. After passing through a 0.22 μm PES filter, the MTT solution was divided into 1 mL portions in sterile centrifuge tubes and stored at −20° C.
6. MTT stock solutions were removed from the freezer to thaw at room temperature. Before adding MTT solutions, cell cultures were visually inspected and imaged using a microscope (to use as a comparison with MTT results). 10 μL of the 5 mg/mL MTT solution was added to each well and the plate was incubated for 4 hours.
7. After 4 h incubation, the culture medium/MT solution was removed gently using a pipette. 100 μL of DMSO was added to each well using a multichannel pipette. The 96-well plates were analyzed in a plate reader using the following method: shake for 5 minutes, wait for 30 seconds, and measure absorbance at 570 nm.
8. Data processing: The average of background $A_{bg}$ was calculated from the blank column. All other data was first treated by subtracting $A_{bg}$. The average A. and standard deviation $S_e$ of each experimental group and the average $A_c$ and standard deviation $S_c$ for control group (with pure culture medium incubation) were then calculated. The cell viability was determined as $A_e/A_c \times 100\%$ and corresponding error as $S_e/A_e \times 100\%$. Significant outliers in any experimental or control group were removed.

Hemolytic Activity Experimental Protocol

CD-1 mouse red blood cells (IC05-3054, Innovative Research, Inc.) were stored at 4° C.

The cells were centrifuged at 500 g for 5 min. The supernatant was aspirated and the resulting pellets were resuspended in 1×PBS. A second identical wash was performed. Resulting solutions were centrifuged at 800 g for 5 min and the cells were resuspended in IX PBS to yield a 5% volume/volume suspension.

COE stock solutions were prepared in 1×PBS at 1.28 mg/m. 160 µL of COE stock solutions were added to 96-well (conical) plates and serially diluted (2-fold). A 40 µL portion of 5% red blood cell solution was added to each well. The final concentrations of each COE were 16 µg/mL to 1024 µg/mL and the final concentration of the red blood cell was 1%. Blank PBS was used as a negative control and 1% Triton X-100 as a positive control.

The plate was incubated with gentle shaking for 1 hour at 37° C. and subsequently centrifuged for 5 min at 800 g at room temperature. A 100 µL portion of the resulting supernatant was transferred to a flat-bottomed 96-well plate. Absorbance at 450 nm was measured on a plate reader. Percent hemolysis was determined by dividing background-corrected absorbance measurements by back-ground corrected measurements for 1% Triton X-100 (positive control for 100% hemolysis).

TABLE 3

MIC Data

| | MIC (µg/mL) | | |
|---|---|---|---|
| | K. aerogenes (−) | S. epidermidis (+) | E. coli K12(−) |
| Formula E | 8 | 4 | 4 |
| Formula J | 16 | 1 | 4 |
| Formula K | | 0.5 | 4 |
| Formula N | | 2 | 128 |
| Formula L | | | 4 |
| Formula M | | | 4 |
| Formula T | 8 | 1 | 4 (8) |
| Formula S | 8 | 2 | 4 |
| Formula R | | 1 | 4 |
| Formula Q | | | 8 |
| Formula P | | | 16 |
| Formula F | 32 | 2 | 32 |
| Formula W | | | 4 |
| Formula V | | | 4 |
| Formula U | | | 4 |
| Formula MM | | | 32 |
| Formula RR | | | 8 |
| Formula GG | | | 32 |
| Formula EH | | | 128 |
| Formula II | | | >128 |
| Formula JJ | | | 16 |
| Formula KK | | | 16 |
| Formula LL | | | 64 |
| Formula BB | | | 8 |
| Formula AA | | 2 | 4 |
| Formula Z | | 16 | 8 |
| Formula Y | | | 32 |
| Formula X | | | 64 |
| Formula NN | | 64 | >128 |
| Formula OO | | >64 | >128 |
| Formula PP | | 16 | 32 |
| Formula QQ | | 32 | |
| Formula SS | | >64 | |
| Formula DD | | 16 | 64 |
| Formula EE | | | 128 |
| Formula G | | | 4 |
| Formula H | | | 4 |
| Formula WW | | 2 | 16 |
| Formula XX | | | 8 |

TABLE 3-continued

MIC Data

| | MIC (µg/mL) | | |
|---|---|---|---|
| | K. aerogenes (−) | S. epidermidis (+) | E. coli K12(−) |
| Formula TT | >128 | 4 | >256 |
| Colistin | 2 | >64 | 1 |
| Cefpirome | 0.25 | 1 | 0.0625 |
| Daptomycin | | | >128 |

TABLE 4

Panel of Pathogens

| | Antimicrobial Class (MIC µg/mL) | |
|---|---|---|
| Pathogen | Standard (AZT) | Formula E |
| S. Typhimurium | 4 | 2 |
| E. coli | 4 | 2 |
| P. aeruginosa | 128 | 8 |
| K pneumoniae* | 256 | 4 |
| S. flexneri | 2 | 2 |
| Y. pseudotuberculosis | 8 | 1 |
| N. gonorrhoeae | 0.03 | 0.5 |
| A. baumannii | 64 | 4 |
| S. aureus (MRSA)* | 128 | 1 |
| S. aureus (MSSA) | >512 | 1 |
| S. pneumoniae D39 | 0.03125 | 4 |
| S. pneumoniae Daw 1 | 8 | 8 |

*Denotes clinical isolates obtained from Cottage Hospital in Santa Barbara, CA.

Formulae UU and O OCOEs are also active against both S. aureus (MRSA) and S. aureus (MSSA). As shown in Tables 5a-5d, several COEs described herein demonstrated efficacy against both Gram-negative and Gram-positive bacteria.

TABLE 5a

| Species | Isolate ID | Phenotype | Formula E (n = 3) MIC (µg/mL) | Formula K (n = 3) MIC (µg/mL) | Formula T (n = 3) MIC (µg/mL) |
|---|---|---|---|---|---|
| E. faecium | 1674620 | VRE | 0.25 | 0.5 | 0.25 |
| S. aureus | ATCC 33591 | MRSA | 0.5 | 0.5 | 0.5 |
| | ATCC BAA-1717 | MRSA | 0.5 | 0.5 | 1 |
| K. pneumoniae | ATCC BAA-2473 | MDR | 2 | 16 | 4 |
| | CDC0010 | MDR | 4 | 32 | 4 |
| A. baumannii | 1674627 | MDR | 4 | >64 | 2 |
| | CDC0290 | MDR | 4 | >64 | 4 |
| P. aeruginosa | 1674623 | MDR | 8 | >64 | 16 |
| | CDC0248 | MDR | 8 | >64 | 32 |
| E. cloacae | 1744299 | ESBL | 2 | 16 | 2 |
| E. coli | ATCC25922 | WT | 1 | 4 | 2 |

TABLE 5b

| Species | Isolate ID | Phenotype | Formula R (n = 3) MIC (µg/mL) | Formula W (n = 3) MIC (µg/mL) | Formula Q (n = 3) MIC (µg/mL) |
|---|---|---|---|---|---|
| E. faecium | 1674620 | VRE | 0.5 | 1 | 1 |
| S. aureus | ATCC 33591 | MRSA | 0.5 | 1 | 1 |
| | ATCC BAA-1717 | MRSA | 1 | 1 | 1 |
| K. pneumonia | ATCC BAA-2473 | MDR | 8 | 8 | 8 |
| | CDC0010 | MDR | 16 | 16 | 32 |
| A. baumannii | 1674627 | MDR | 32 | 32 | 64 |
| | CDCO290 | MDR | 32 | 32 | 64 |
| P. aeruginosa | 1674623 | MDR | 64 | >64 | >64 |
| | CDCO248 | MDR | 64 | >64 | >64 |
| E. cloacae | 1744299 | ESBL | 8 | 4 | 4 |
| E. coli | ATCC25922 | WT | 4 | 2 | 4 |

TABLE 5c

| Species | Isolate ID | Phenotype | Formula P (n = 3) MIC (µg/mL) | Formula F (n = 3) MIC (µg/mL) | Formula RR (n = 3) MIC (µg/mL) |
|---|---|---|---|---|---|
| E. faecium | 1674620 | VRE | 4 | 8 | 0.25 |
| S. aureus | ATCC 33591 | MRSA | 1 | 2 | 4 |
| | ATCC BAA-1717 | MRSA | 2 | 2 | 2 |
| K. pneumonia | ATCC BAA-2473 | MDR | 16 | 32 | 16 |
| | CDC0010 | MDR | 32 | 64 | 16 |
| A. baumannii | 1674627 | MDR | 64 | 64 | 16 |
| | CDCO290 | MDR | 64 | 64 | 16 |
| P. aeruginosa | 1674623 | MDR | >64 | >64 | >64 |
| | CDCO248 | MDR | >64 | >64 | >64 |
| E. cloacae | 1744299 | ESBL | 8 | 8 | 32 |
| E. coli | ATCC25922 | WT | 8 | 8 | 4 |

TABLE 5d

| Species | Isolate ID | Phenotype | Formula BB (n = 3) MIC (µg/mL) | Formula AA (n = 3) MIC (µg/mL) | Formula G (n = 3) MIC (µg/mL) |
|---|---|---|---|---|---|
| E. faecium | 1674620 | VRE | 0.25 | 0.25 | 1 |
| S. aureus | ATCC 33591 | MRSA | 2 | 0.5 | 1 |
| | ATCC BAA-1717 | MRSA | 1 | 4 | 2 |
| K. pneumonia | ATCC BAA-2473 | MDR | 2 | 4 | 4 |
| | CDC0010 | MDR | 2 | 16 | 16 |
| A. baumannii | 1674627 | MDR | 2 | 16 | 32 |
| | CDCO290 | MDR | 2 | 16 | 32 |
| P. aeruginosa | 1674623 | MDR | 16 | 64 | 64 |
| | CDCO248 | MDR | 32 | 32 | 64 |
| E. cloacae | 1744299 | ESBL | 2 | 4 | 4 |
| E. coli | ATCC25922 | WT | 2 | 1 | 1 |

TABLE 6

| Compound | Hep G2 | NIH 3T3 | J774 | RAW 264.7 | **Hep G2 | **Primary Human Hepatocytes | **HRPTEpiC |
|---|---|---|---|---|---|---|---|
| | \*IC$_{50}$ (µg/mL) | | | | | | |
| Formula E | 7.3 | 10.4 | 2.5 | 3.76 | 5.6 | 13.2 | 2.6 |
| Formula J | 41.3 | 26.7 | 7.5 | | | | |
| Formula L | | 6.4 | | | | | |
| Formula M | | 57 | | | | | |
| Formula K | >128 (57%) | 102.2 | 68.5 | | 73.6 | 273.1 | 44.9 |
| Formula N | | 124.4 | | | | | |
| Formula A | >128 (68%) | | | | | | |
| Formula B | 9.9 | | | | | | |
| Formula C | 29.7 | | | | | | |
| Formula D | 20.7 | | | | | | |
| Formula T | 15.3 | 12.4 | 4.6 | | 11.6 | 31.8 | 2.8 |
| Formula S | >128 (52%) | 42.3 | 22.6 | | | | |
| Formula R | >1024 (85%) | 120.5 | | | 333 | 324 | 68 |
| Formula Q | >128 (91%) | | | | | | |
| Formula P | | | | | | | |
| Formula F | >1024 (100%) | >128 (56.2%) | >128 (51%) | | >324 (70%) | >324 (79%) | 79.2 |
| Formula W | 473.6 | | | | >324 (80%) | >324 (81%) | 113.8 |
| Formula RR | 56.7 | | | | | | |

TABLE 6-continued

| Compound | Hep G2 | NIH 3T3 | J774 | RAW 264.7 | **Hep G2 | **Primary Human Hepatocytes | **HRPTEpiC |
|---|---|---|---|---|---|---|---|
| | *IC$_{50}$ (μg/mL) | | | | | | |
| Formula MM | | 3.6 | | | | | |
| Formula GG | | 77.8 | | | | | |
| Formula II | | >256 (78%) | | | | | |
| Formula JJ | | <32 (0.2%) | | | | | |
| Formula LL | | <32 (18.7%) | | | | | |
| Formula BB | 15.1 | | | | | | |
| Formula AA | 637.3 | | | | | | |
| Formula Z | >128 (87%) | | | | | | |
| Formula Y | >1024 (61%) | | | | | | |
| Formula X | >1024 (73%) | | | | | | |
| Formula DD | >128 (85%) | | | | | | |
| Formula OO | >1024 (61%) | | | | | | |
| Formula H | 13 | | | | | | |
| Formula G | 888.6 | | | | | | |
| Formula EE | >128 (85%) | | | | | | |
| Formula O | >128 (71%) | | | | | | |
| Formula CC | 22.3 | | | | | | |
| Formula FF | 34.2 | | | | | | |
| Formula TT | >128 (70%) | 69.3 | | | 94.6 | 102 | 6.3 |
| Formula WW | 45.4 | 30.9 | | | | | |
| Formula XX | >128 (85%) | | | | | | |
| Formula UU | 43.7 | | | | | | |
| Formula VV | >128 (64%) | | | | | | |
| Cefpirome | >128 (101%) | >128 (81%) | >128 (107%) | | | | |
| Meropenem | >128 (96%) | | | | | | |
| Colistin | | >128 (104%) | >128 (115%) | >20 (109%) | >324 (100%) | >324 (101%) | 215 |

Figure 13A:
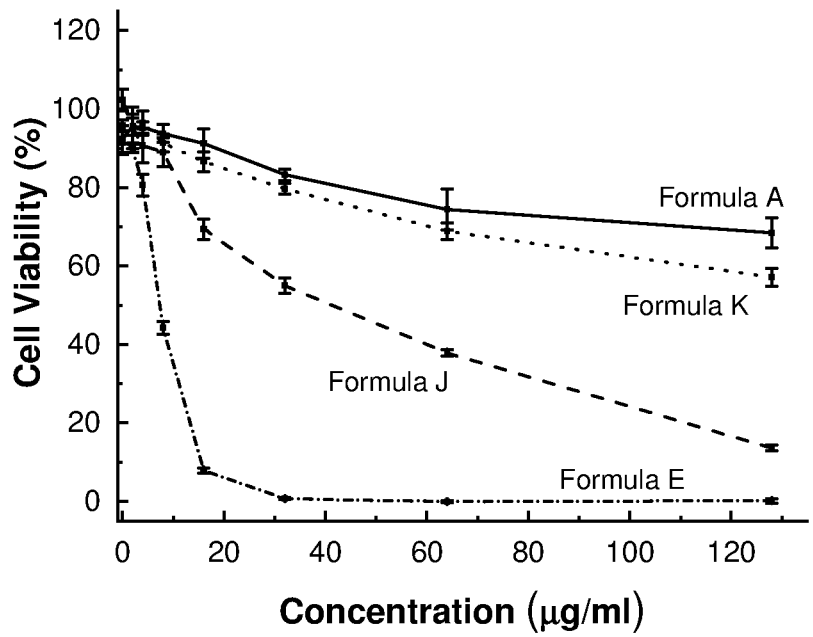
FIGS. 13A-H depict the cytotoxicity of selected Formulae against Hep G2 cells.
Figure 13B:
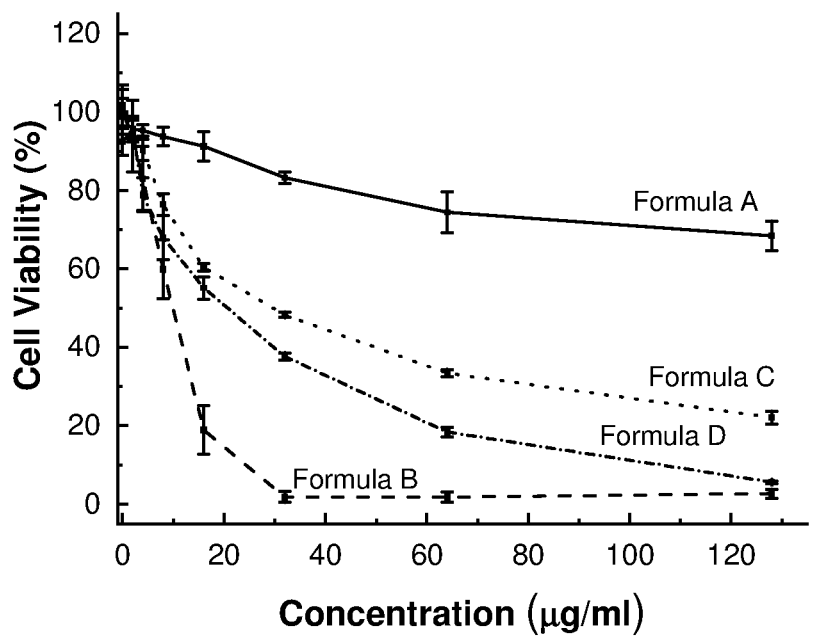
Figure 13C:
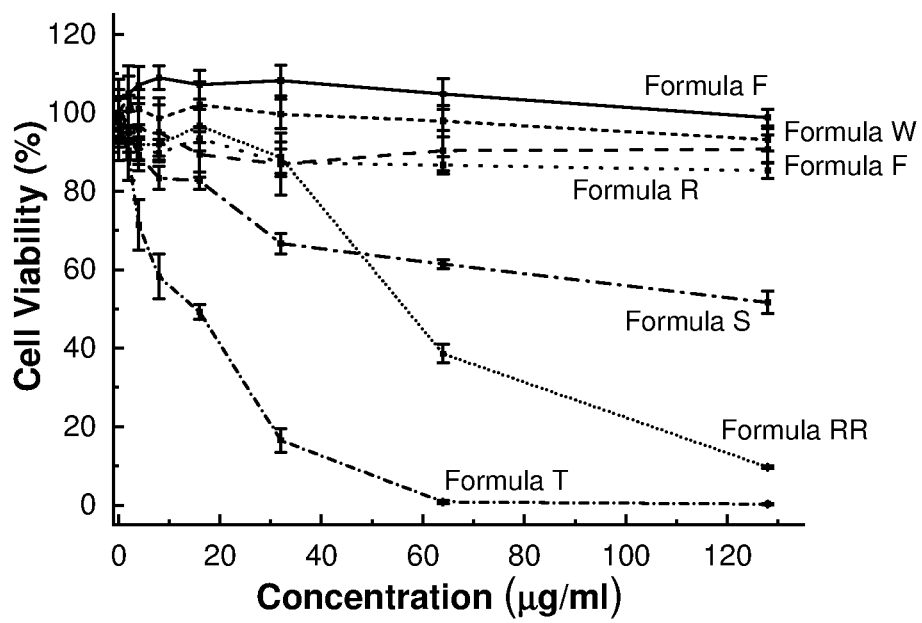
Figure 13D:
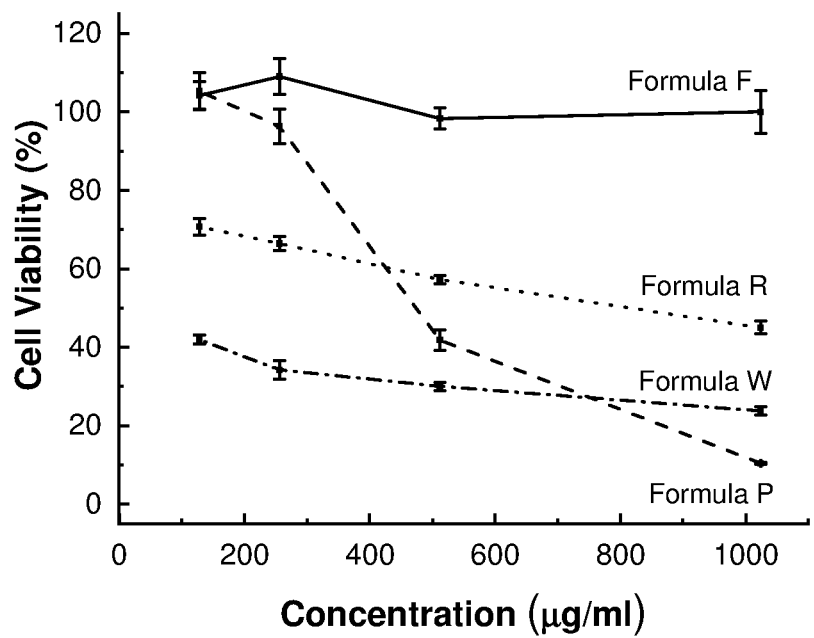
Figure 14A:
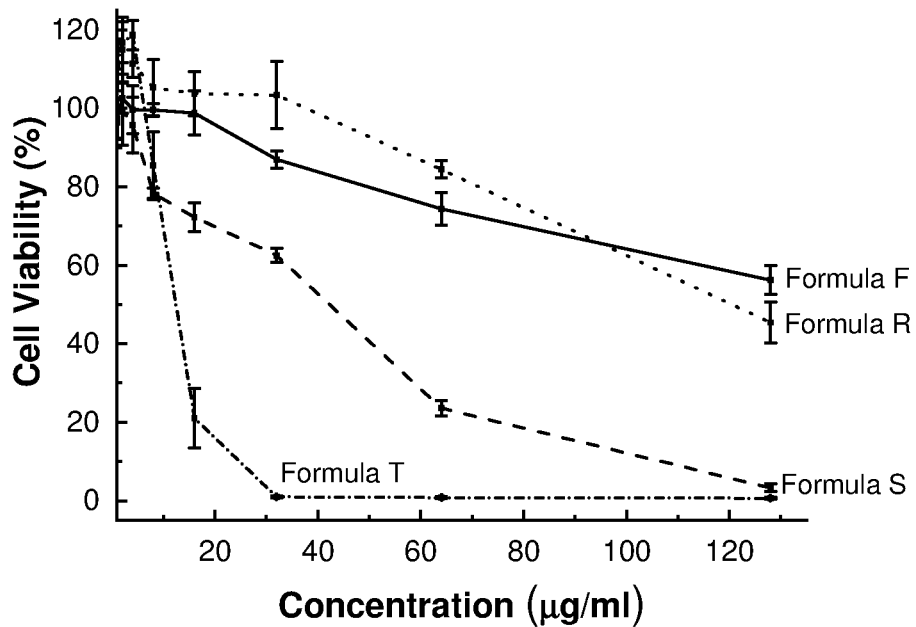
FIGS. 14A-C depict the cytotoxicity of selected Formulae against NIH 3T3 cells.
Figure 14B:
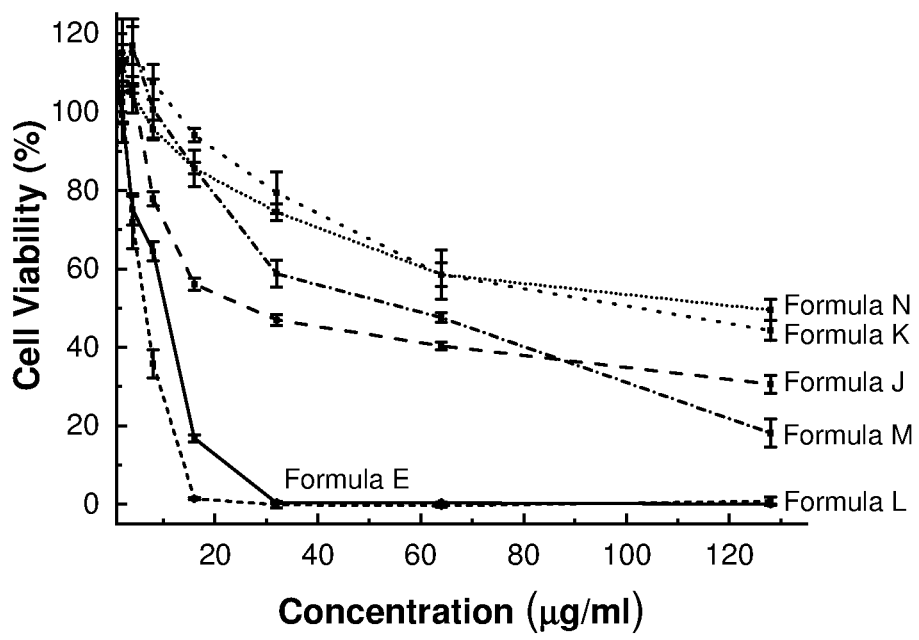
Figure 14C:
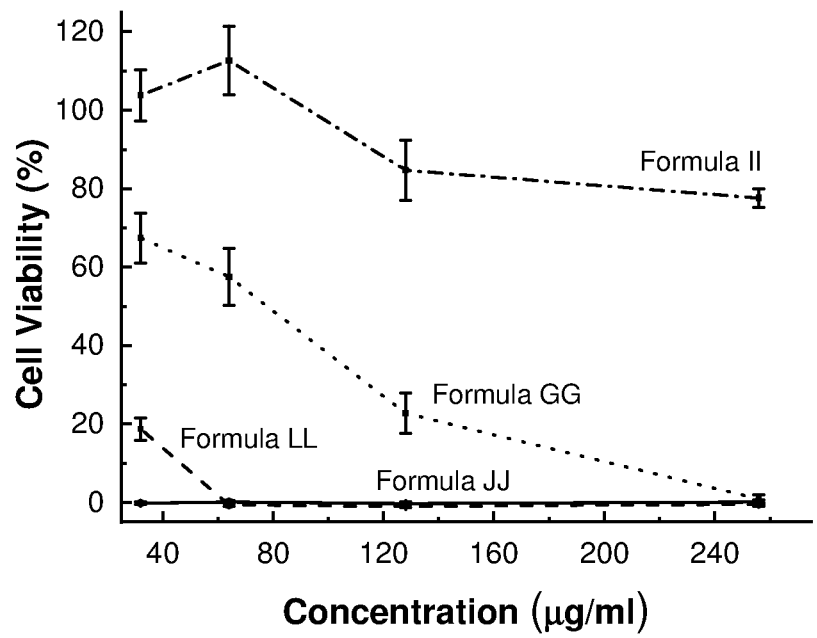
Figure 15A:
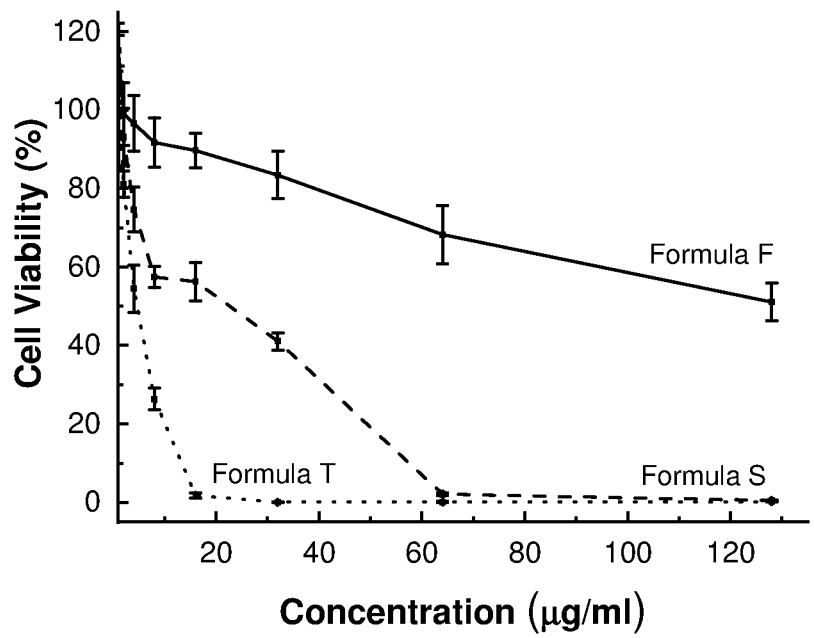
FIGS. 15A-B depict the cytotoxicity of selected Formulae against J774 cells.
Figure 15B:
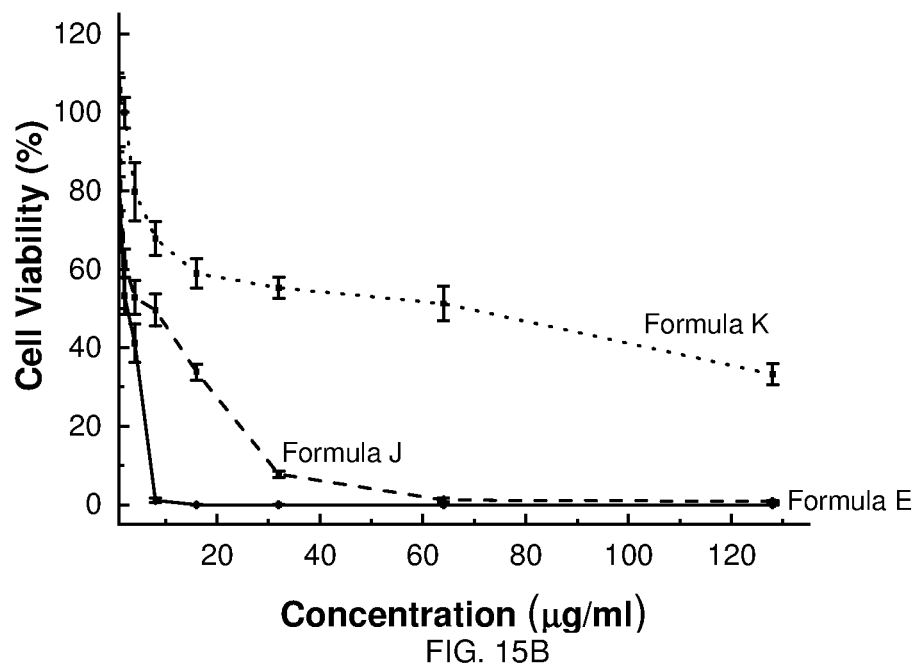
Figure 16A:
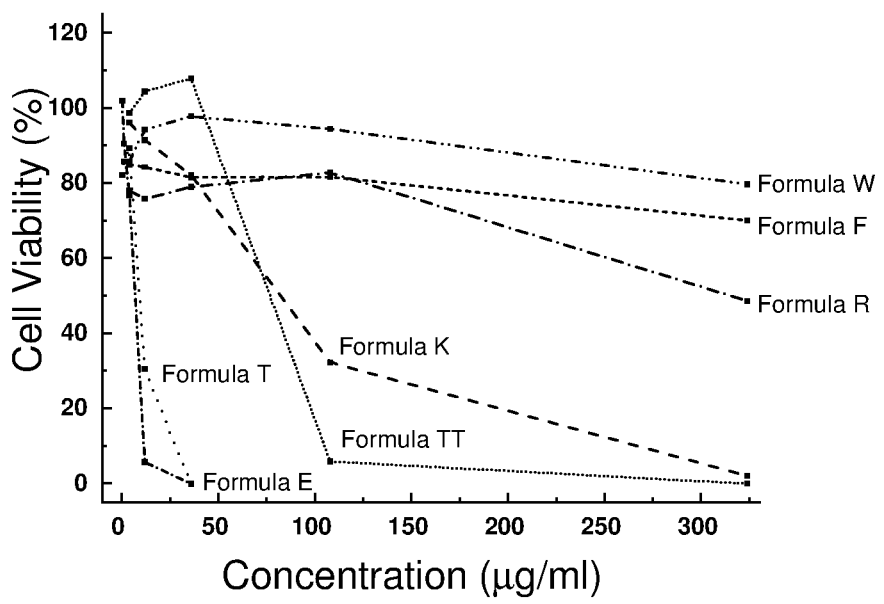
FIGS. 16A-C depict the cytotoxicity of selected Formulae tested by Eurofins Pharma Discovery Services against Hep G2 cells (FIG. 16A), primary human hepatocytes (FIG. 16B), and HRPTEpiC (FIG. 16C).
Figure 16B:
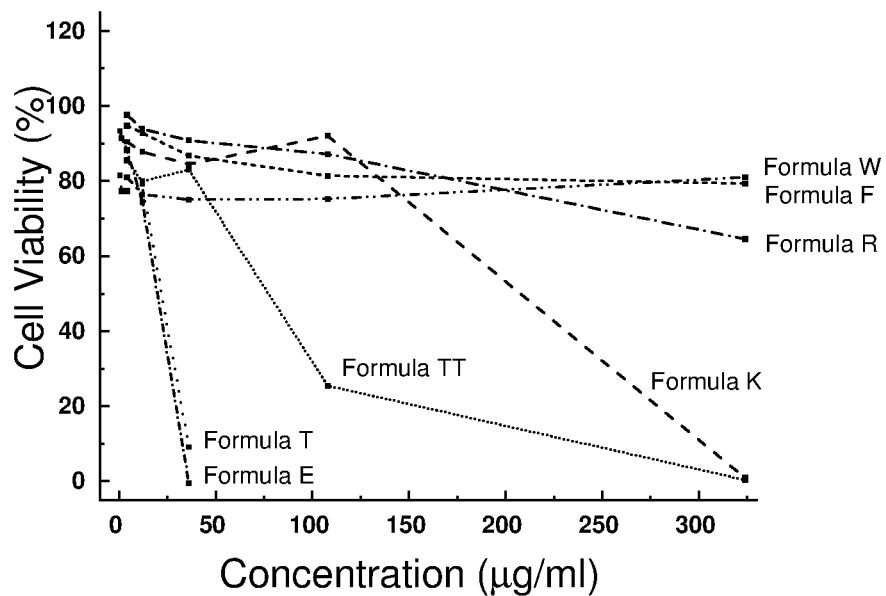
Figure 16C:
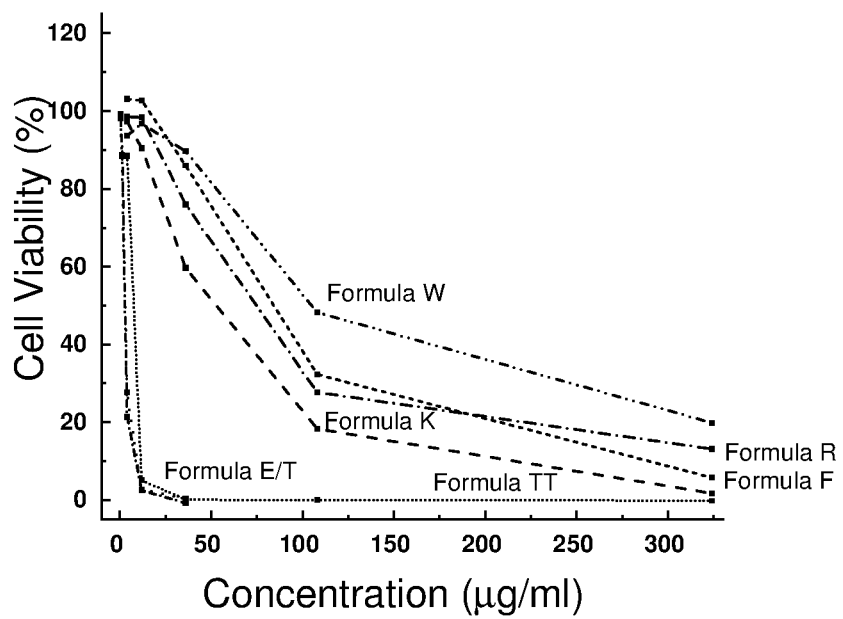

*cell viability at the highest or lowest test concentration is shown in parentheses for IC$_{50}$ > highest test concentration or < lowest test concentration
**Data provided by Eurofins As shown herein, several COEs have biological activity against various bacteria, both Gram-positive and Gram-negative. When the trimethylammonium group (—N(CH$_3$)$_3$$^+$) is modified to increase its hydrophobic character; for example, by exchanging a methyl group for a longer alkyl chain, the antimicrobial activity of the compound can be optimized. Variation of cytotoxicity is evident as the structure of the hydrophobic group is modified. Specifically, FIG. 13A shows the results of replacing one of the methyl groups (—N(CH$_3$)$_3$$^+$) of Formula A with hexyl (Formula E), pentyl (Formula J) and butyl (Formula K) against Hep G2 cells. This result is also observed for other cell lines in FIG. 14B (NIH 3T3) and FIG. 15B (J774), and Table 6. Functional groups beyond linear alkyl have been explored, including, but not limited to branched and substituted alkyls, heterocyclyls and short ethylene oxide chains. By varying the groups present on the charged nitrogen(s), one has the opportunity to optimize cell interactive and cytotoxic properties while also maintaining significant antibacterial activity, as the examples provided herein demonstrate.

Without wishing to be bound by theory, Applicants believe the unique cytotoxicity profiles resultant from the cationic group modification can be analyzed together with MIC data for biological targets of interest, as described herein, to identify compounds of Formula 1, Formula 2, Formula 3, Formula 4, Formula 5, Formula 6, Formula 7, Formula (I), Formula (II), Formula (III), Formula (IV) and/or Formula (V), or a pharmaceutically acceptable isomer, racemate, hydrate, solvate, isotope, or salt of any of the foregoing, as potential new drug leads, wherein Formula (I), Formula (II), Formula (III), Formula (IV) and Formula (V), or a pharmaceutically acceptable isomer, racemate, hydrate, solvate, isotope, or salt of any of the foregoing, are as provided in the section entitled "Further Formulae." As shown by the data in Table 2, this data indicates that compounds described have sufficiently low cytotoxicity at MIC concentrations.

As shown in the tables (such as Tables 3 and 5a-5d) provided herein, several COEs described herein, including Formula E, exhibited low MIC values for both Gram-positive and Gram-negative bacteria.

Formula E was more effective than Formula A, which highlights the important and surprising role of a substitution of methyl for hexyl in the quaternary ammonium groups responsible for controlling water solubility. Without wishing to be bound by theory, Applicant believes that the methyl for hexyl substitution fine-tunes drug association with the cell wall and/or membrane, thereby enhancing efficacy. Additional, considerations, with respect to solubility and efficacy, arise when comparing Formula C with Formula D; as the efficacy of Formula D could not be detected because of its low solubility. Thus, there appears to exist a balance between the propensity of a compound, such as a COE described herein, associating with the cells, and their solubility in aqueous media: e.g., COEs with the same charged groups and internal structure have sufficient propensity for cells, likely mediated via hydrophobic interactions, and their solubility in aqueous media, which was improved through minimizing the hydrophobic content.

Tables 5a-5d provide additional MIC data for compounds of described herein against a broader panel of bacterial species. This data further demonstrates the surprising biological activity resulting from the introduction of a larger alkyl group in place of a methyl on the trimethylammonium cationic group. For example, comparing the data for Formula T and Formula F clearly demonstrates the improved performance of the former against this panel of bacteria; whereby Formula T demonstrates lower MIC values against each species tested relative to Formula F.

Further, data from Tables 5a-5d demonstrates an ability to modulate the efficacy of the compounds by changing the structure of the non-methyl group on the cationic moiety. For example, in Panel B, Formula R, Formula W and Formula Q are ethyl, propyl and butyl replacements, respectively on Formula F. As it was for Formula T, Formula R, Formula W and Formula Q also demonstrate improvements in efficacy across the panel tested, particularly the more lipophilic butyl derivative, Formula Q. Collectively, Formula R, Formula W and Formula Q show increasing efficacy as chain length increases, particularly against Efaecium.

Figure 13E:
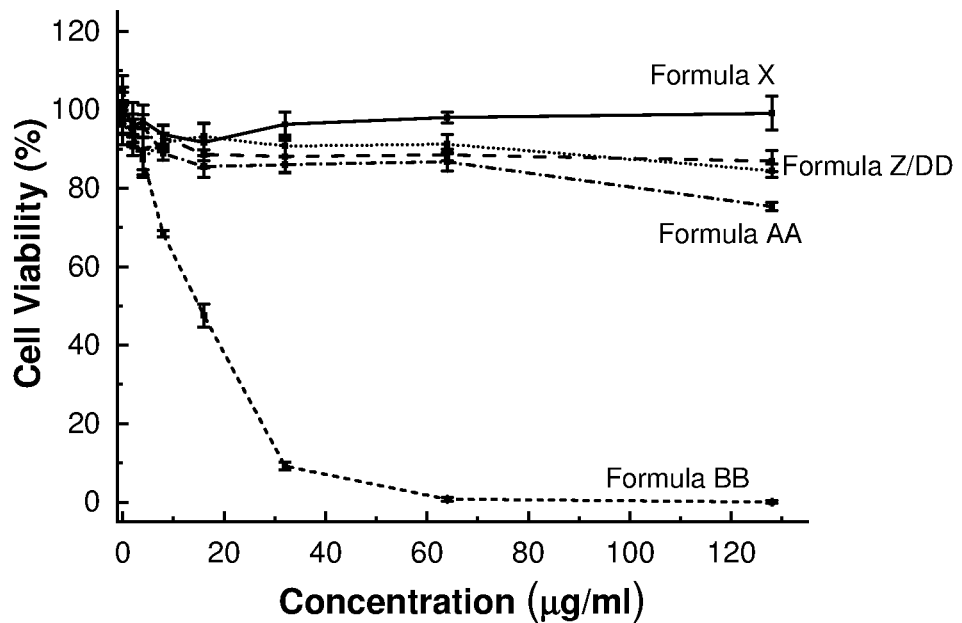
Figure 13F:
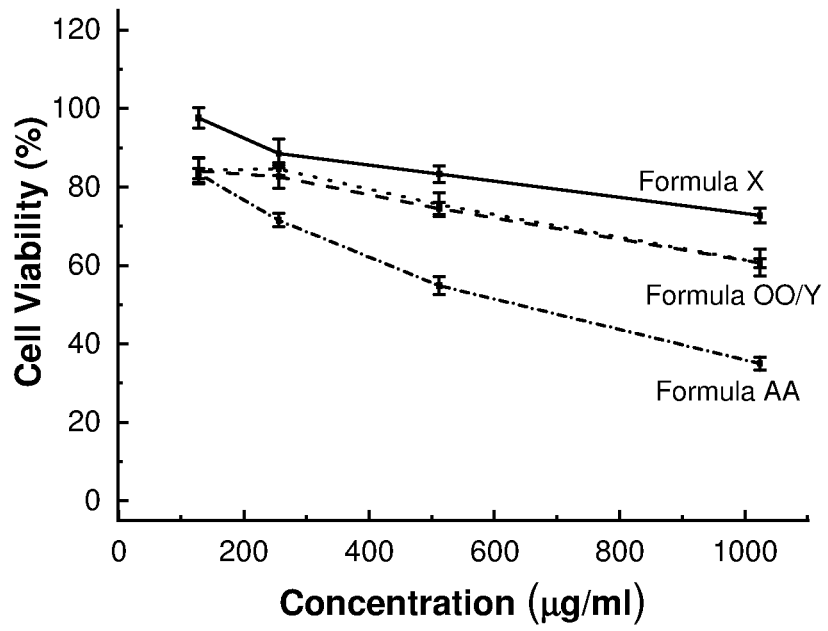
Figure 13G:
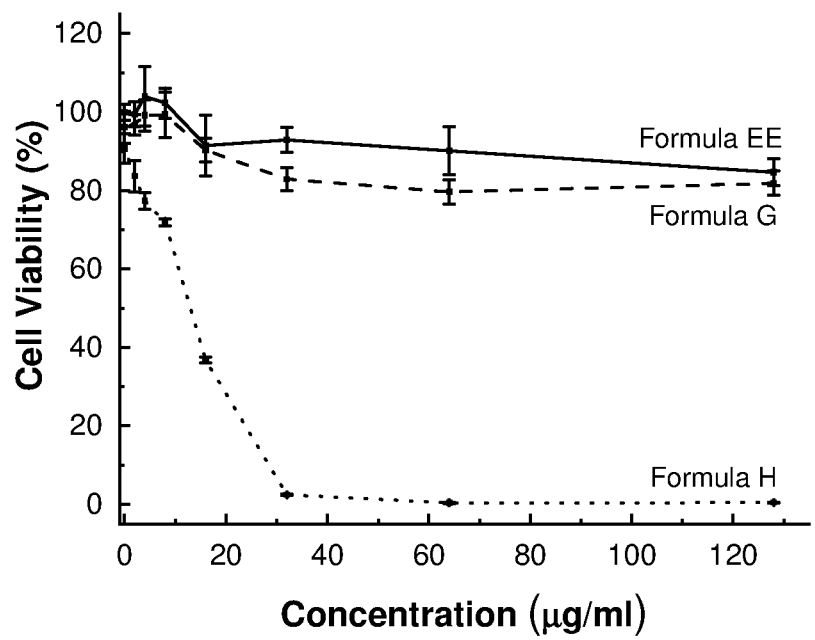
Figure 13H:
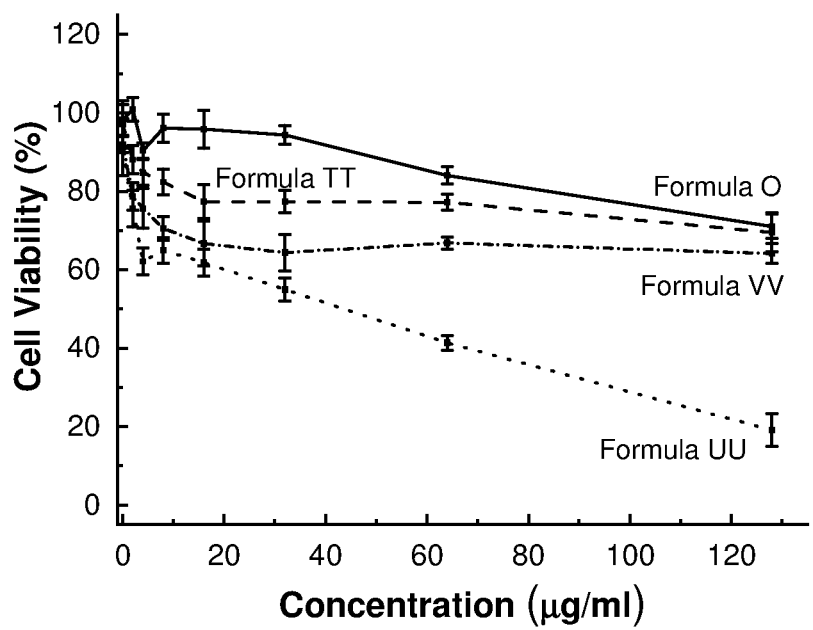

An additional comparison can be made between Formula BB and Formula AA, wherein the hexyl derivative (Formula BB) demonstrates increased efficacy relative to the butyl (Formula AA). These same two compounds had their cytotoxicity evaluated against the Hep G2 cell line (FIG. 13E) and the differences here should also be noted. While Formula AA demonstrated low cytotoxicity as shown by its $IC_{50}$ of 637 µg/mL, Formula BB demonstrated high cytotoxicity as shown by its $IC_{50}$ of 15 µg/mL. However, at concentrations that proved efficacious against bacterial species (0.25-4 µg/mL), Formula BB demonstrated cell viability of ~90%.

Figure 17A:
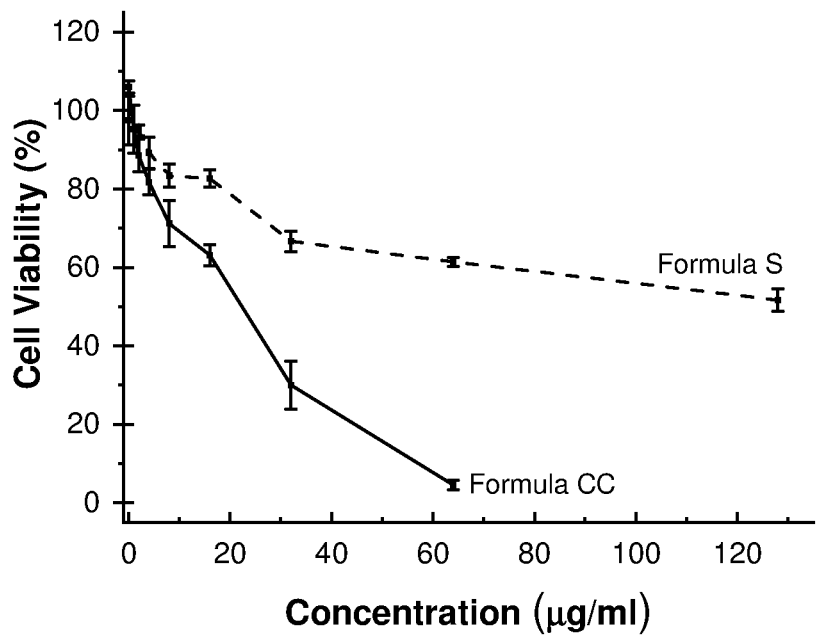
Figure 17B:
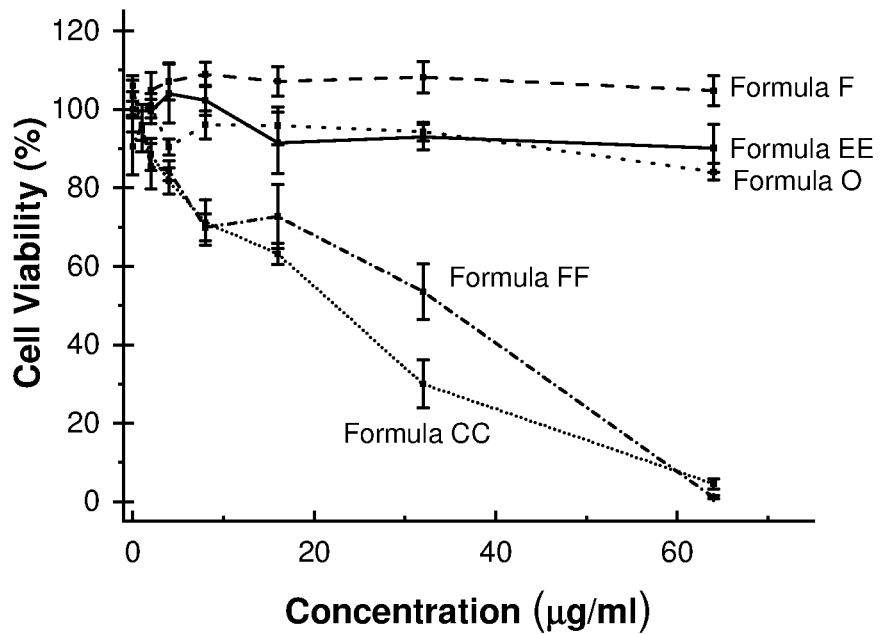

Collectively, the ability to impart dramatic change in cytotoxicity with only a minor drop in efficacy, presents a powerful method for optimizing and selecting compounds with good therapeutic potential. The present application allows for this optimization due to the novel, methyl-replacement component of compound design. FIGS. 17A-C demonstrate how the introduction of the pendant, hydrophobic group, and shortening the linker between the conjugated interior and the cationic moiety can provide incremental opportunity to optimize biological activity by identifying linker lengths that provide desired outcomes against species of concern. These examples describe significant improvements to efficacy with concurrent reductions in cytotoxicity.

Table 4 summarizes, by way of comparison, Formula E's (methyl for hexyl alkyl substitution) consistently low (single digit) MIC values relative to a known antibiotic (AZT) and two trimethylammonium type COE compounds.

In Vivo Experiment

Gram-Negative Bacteria:

*Klebsiella pneumoniae* is streaked from frozen stocks onto Luria-Bertani (LB) agar plates and incubated overnight at 37° C. Single colonies are inoculated into LB broth and incubated overnight with shaking at 37° C. Bacteria are pelleted by centrifugation, washed, and suspended in sterile PBS. Intravenous (i.v.) injection into the retroorbital sinus of 1 to $2\times10^8$ cells (at least $20\times LD_{50}$) is done in 100 µL volume. A dose of $20\times LD_{50}$ ensures that virtually all infected animals will undergo sepsis.

Gram-Positive Bacteria:

*Staphylococcus aureus* is streaked from frozen stocks onto Tryptic Soy (TS) agar plates and incubated overnight at 37° C. Single colonies are inoculated into TS broth and incubated overnight with shaking at 37° C. After overnight incubation, bacteria are re-inoculated as a 1:100 sub-culture into fresh TS broth and cultured to mid-log phase ($A_{600}$=0.4), centrifuged at 1500 g for 5 min, washed, and suspended in PBS. Intravenous (i.v.) injection into the retroorbital sinus of 1 to $2\times10^8$ cells (at least $20\times LD_{50}$) is done in 100 µL volume. A dose of $20\times LD_{50}$ ensures that virtually all infected animals will undergo sepsis.

In Vivo Drug Efficacy Testing:

Following the infection protocols for Gram-negative and Gram-positive pathogens in the mouse model as described above, drug efficacy would be assessed as reduced morbidity/mortality compared to vehicle control following drug delivery beginning 2 h post-infection, and continued throughout course of infection. As shown by the results in Table 7, subjects treated with a COE described herein resulted in the survival of all, or nearly all, 10 subjects when the subject was infected with a Gram-negative or Gram-positive bacteria.

TABLE 7

| In Vivo Results | | | |
|---|---|---|---|
| Species | Phenotype | Treated Survivors | Untreated survivors |
| S. aureus | MRSA | 10/10 | 0/10 |
| S. aureus | MRSA | 9/10 | 0/10 |
| K. pneumoniae | XDR | 9/10 | 0/10 |

Furthermore, although the foregoing has been described in some detail by way of illustrations and examples for purposes of clarity and understanding, it will be understood by those of skill in the art that numerous and various modifications can be made without departing from the spirit of the present disclosure. The various embodiments described above can be combined to provide further embodiments. These and other changes can be made to the embodiments in light of the above-detailed description. Therefore, it should be clearly understood that the forms disclosed herein are illustrative only and are not intended to limit the scope of the present disclosure, but rather to also cover all modification and alternatives coming with the true scope and spirit of the invention. In general, in the following claims, the terms used should not be construed to limit the claims to the specific embodiments disclosed in the specification and the claims, but should be construed to include all possible embodiments along with the full scope of equivalents to which such claims are entitled.

We claim:

1. A conjugated oligoelectrolyte (COE) having a structural Formula 5:

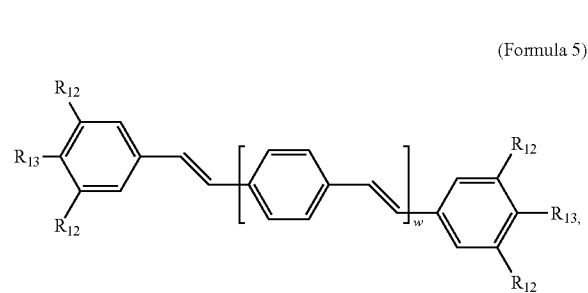

(Formula 5)

or a pharmaceutically acceptable salt thereof, wherein $R_{12}$ is $-O-R_{14}-N(R_{15})_3$ or $-O-R_{14}-R_{17}$; $R_{13}$ is H; $R_{14}$ is $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$ or $-(CH_2)_{10}-$; a $R_{15}$ is methyl; a $R_{15}$ a is methyl or $C_2$-$C_{10}$ alkyl; and a $R_{15}$ is $C_2$-$C_{10}$ alkyl, hydroxyalkyl, aminoalkyl, $$\text{-------}(C_{1-4}\text{ alkyl})-\overset{O}{\underset{O^-}{\overset{\|}{S}}}=O$$

or $-((CH_2)_2-O)_{1-4}-CH_3$; or two $R_{15}$ are taken together with the nitrogen to which they are attached to form a monocyclic N-linked heterocyclyl; and the remaining $R_{15}$ is $C_1$-$C_{10}$ alkyl; $R_{17}$ is NH—(=NH)NH$_2$; w is 0, 1 or 2; and the counter ions include I$^-$, Br$^-$, Cl$^-$, F$^-$, organic anion, BIm$_4^-$ or B(ArF)$_4^-$.

2. The COE of claim 1, wherein the monocyclic N-linked heterocyclyl is 5-membered or a 6-membered monocyclic N-linked heterocyclyl.

3. A COE having a structure selected from the group consisting of:

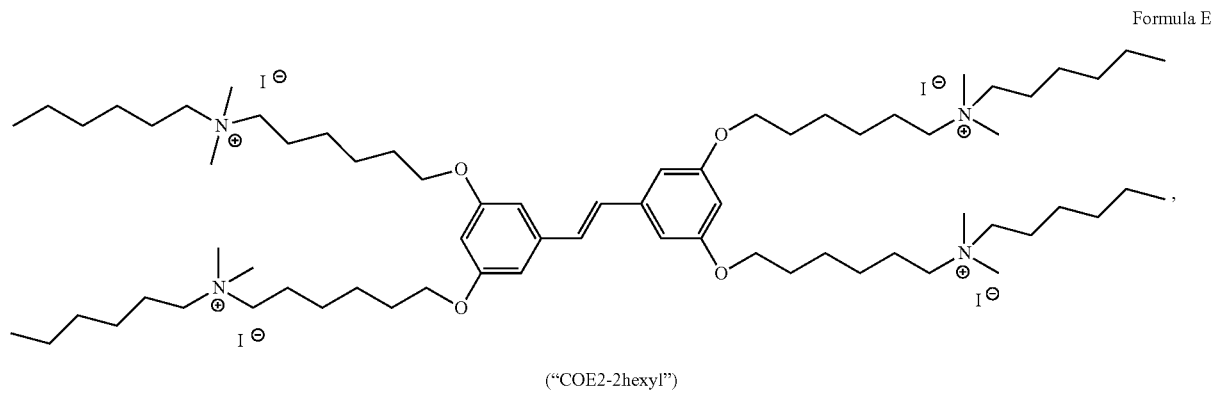

("COE2-2hexyl")

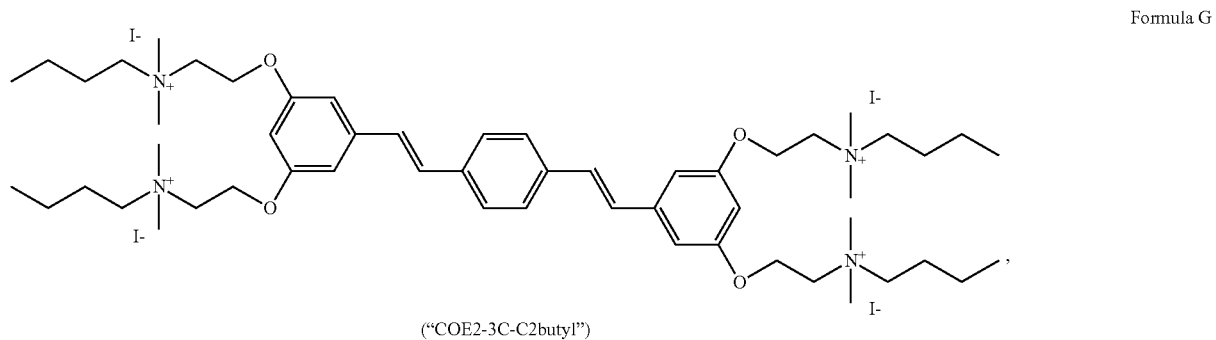

("COE2-3C-C2butyl")

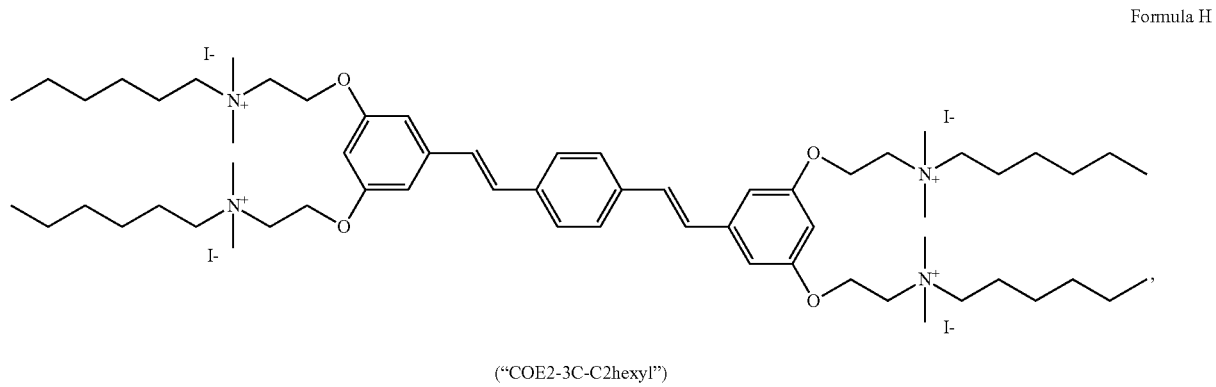

("COE2-3C-C2hexyl")

-continued
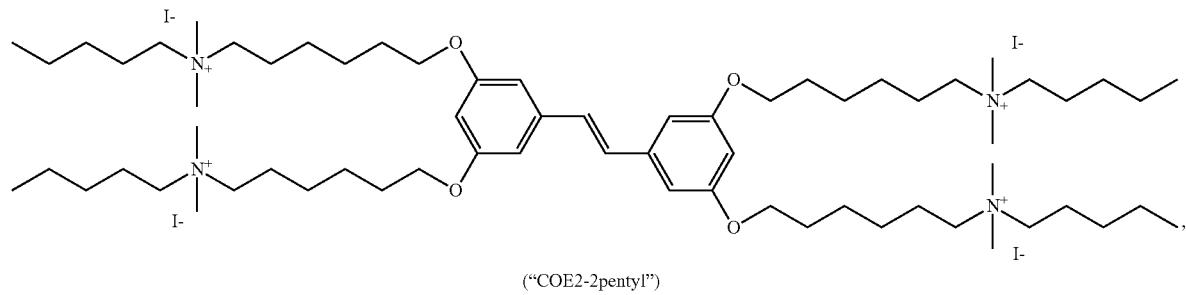
("COE2-2pentyl"), Formula J
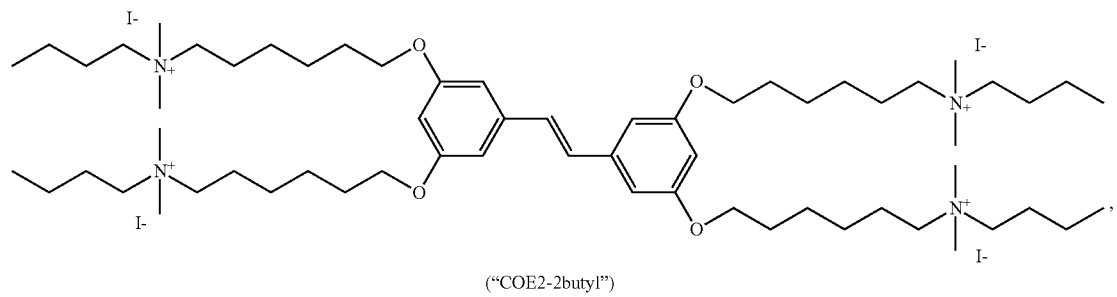
("COE2-2butyl"), Formula K
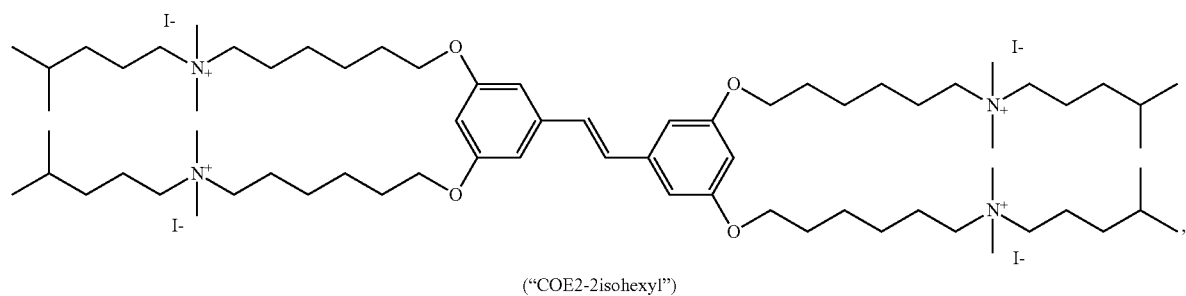
("COE2-2isohexyl"), Formula L
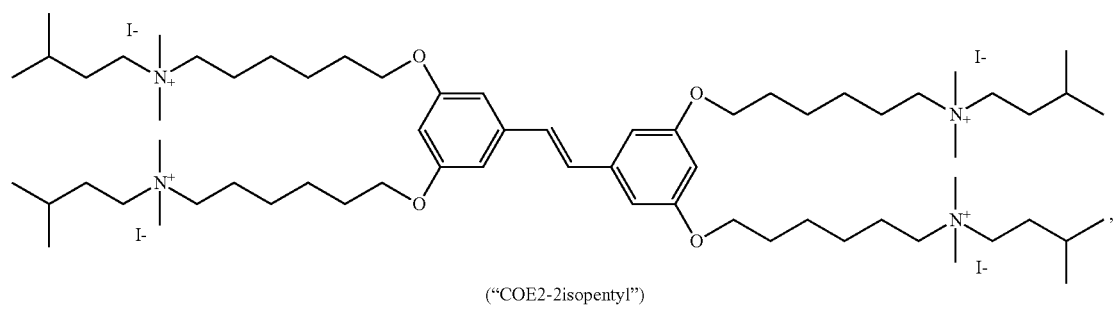
("COE2-2isopentyl"), Formula M
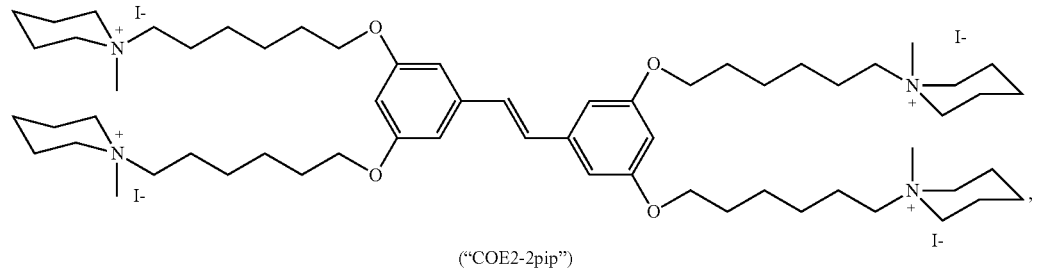
("COE2-2pip"), Formula N -continued
Formula P
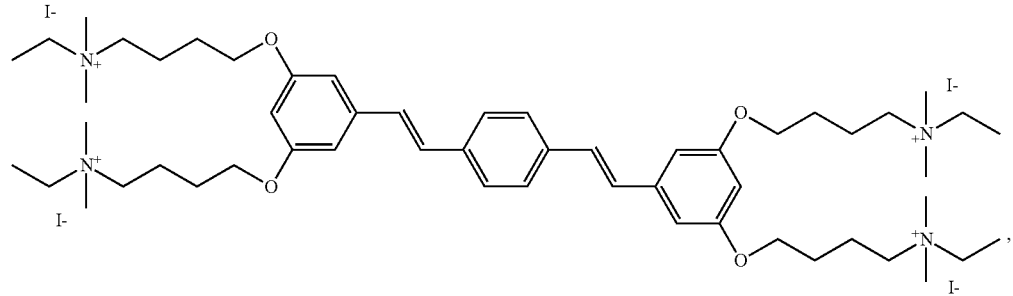
("COE2-3C-C4ethyl")
Formula Q
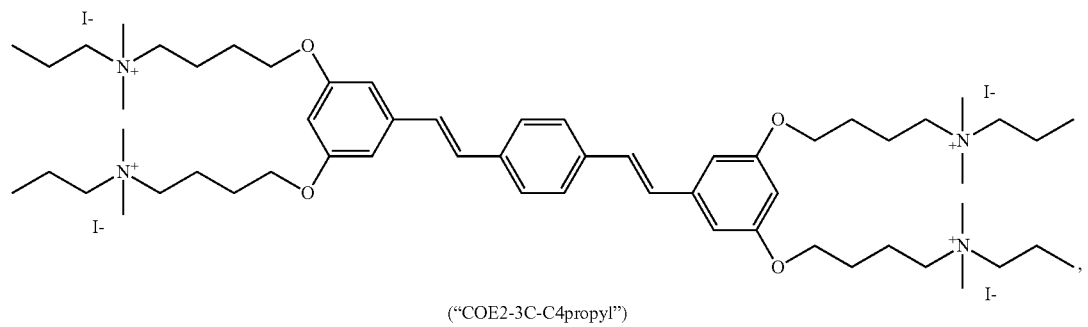
("COE2-3C-C4propyl")
Formula R
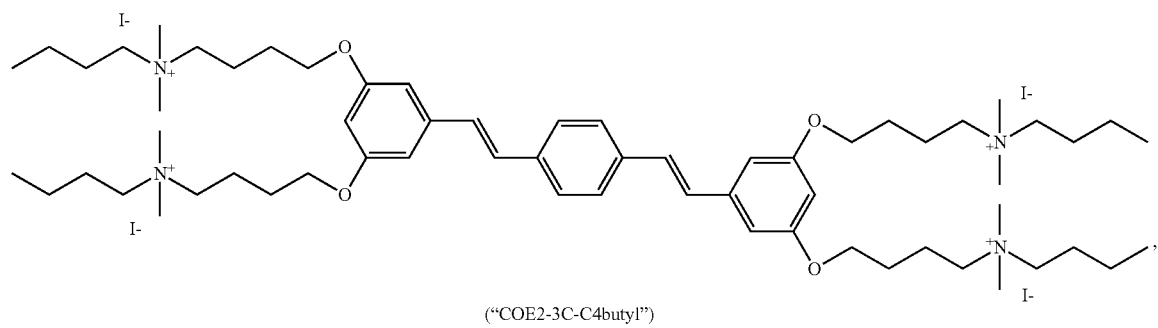
("COE2-3C-C4butyl")
Formula S
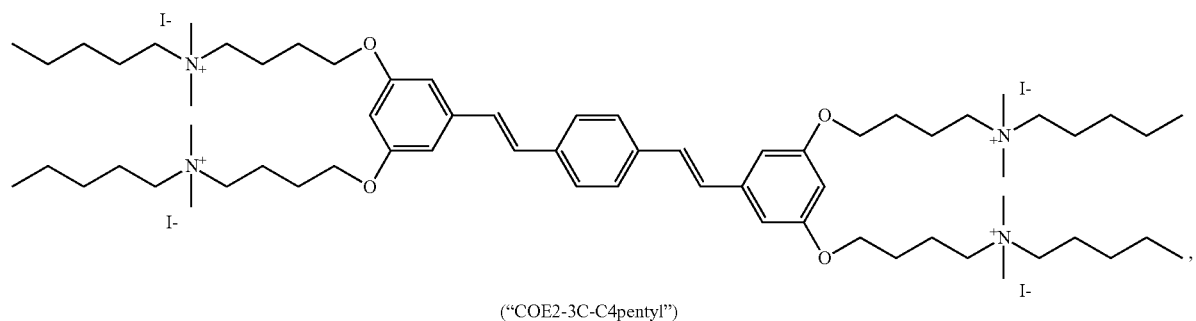
("COE2-3C-C4pentyl")

-continued
Formula T
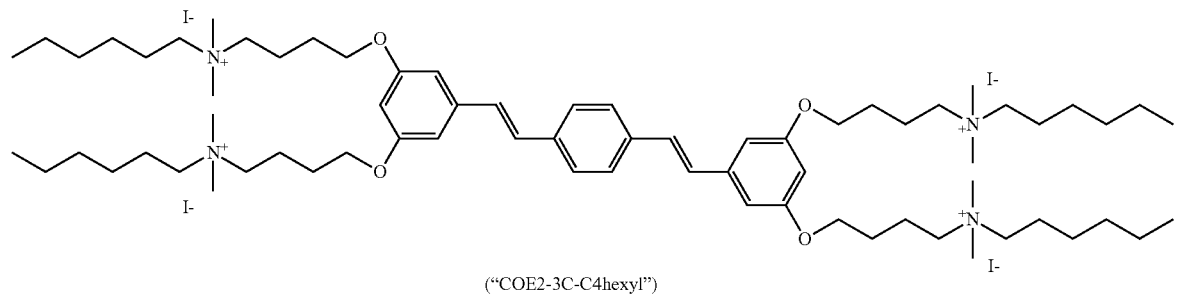
("COE2-3C-C4hexyl")
Formula U
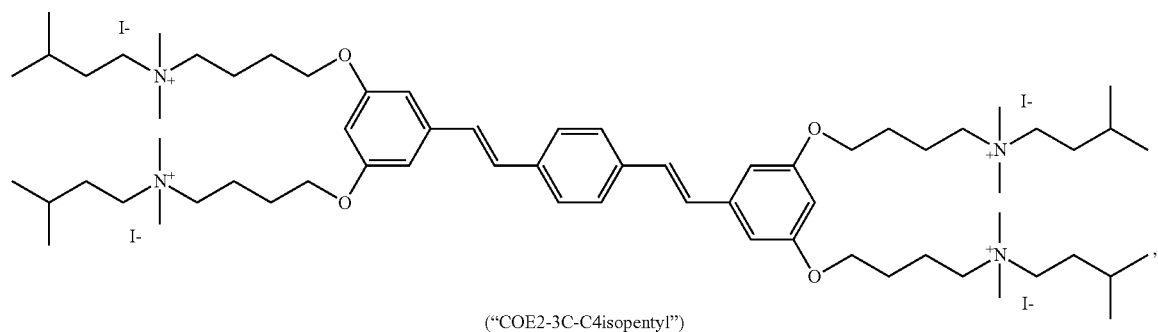
("COE2-3C-C4isopentyl")
Formula V
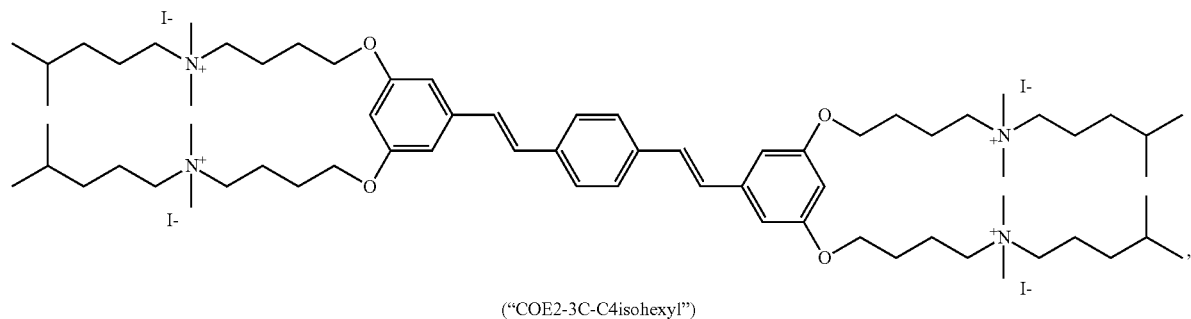
("COE2-3C-C4isohexyl")
Formula W
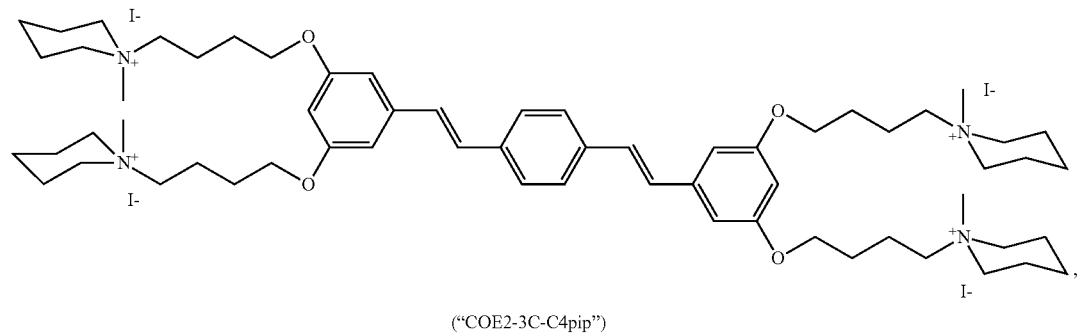
("COE2-3C-C4pip")

-continued
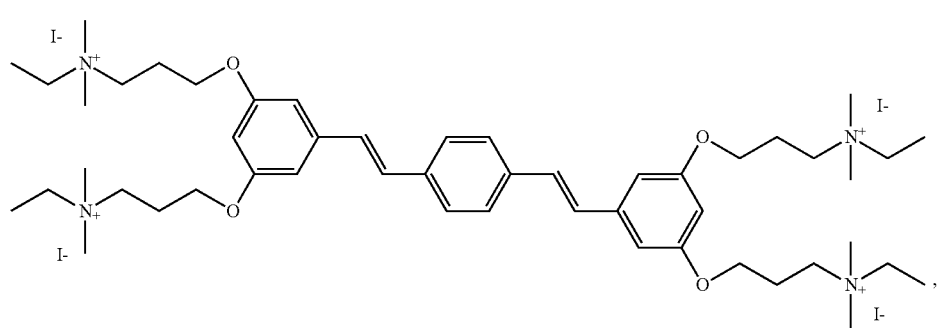
Formula Y
("COE2-3C-C3ethyl")
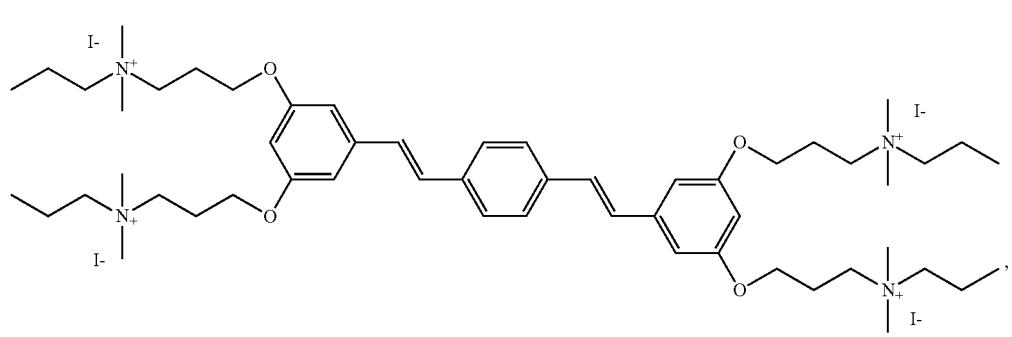
Formula Z
("COE2-3C-C3propyl")
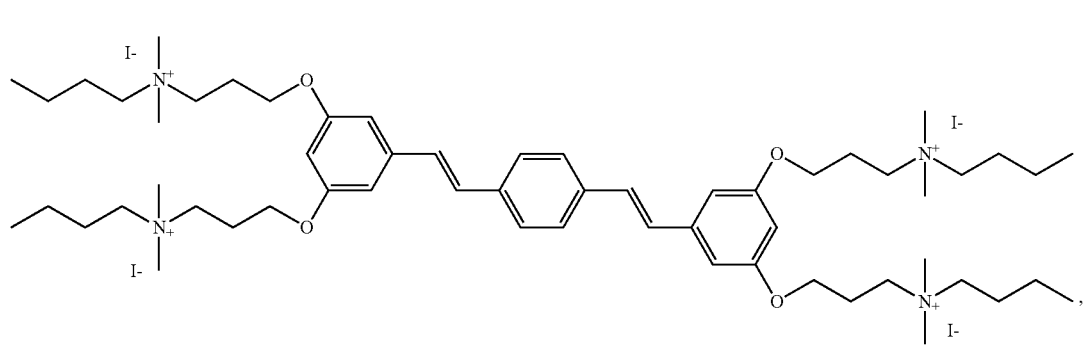
Formula AA
("COE2-3C-C3butyl")
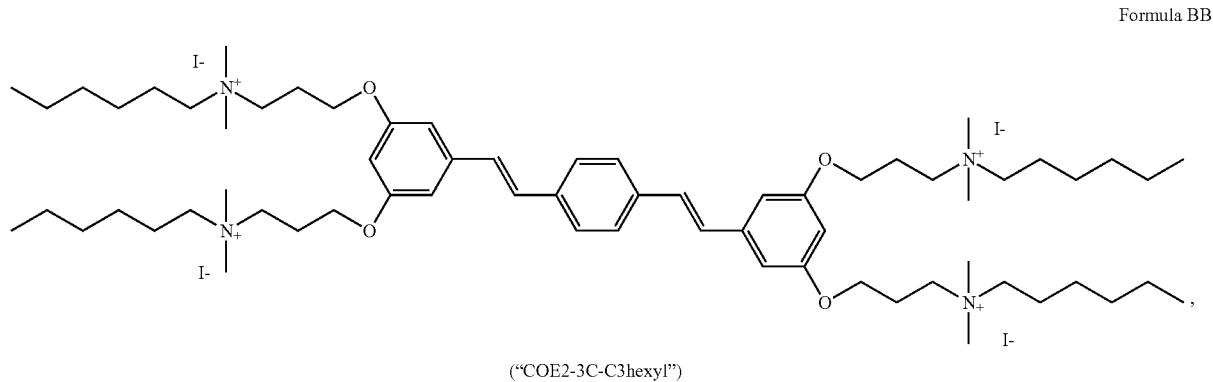
Formula BB
("COE2-3C-C3hexyl")

-continued
Formula DD
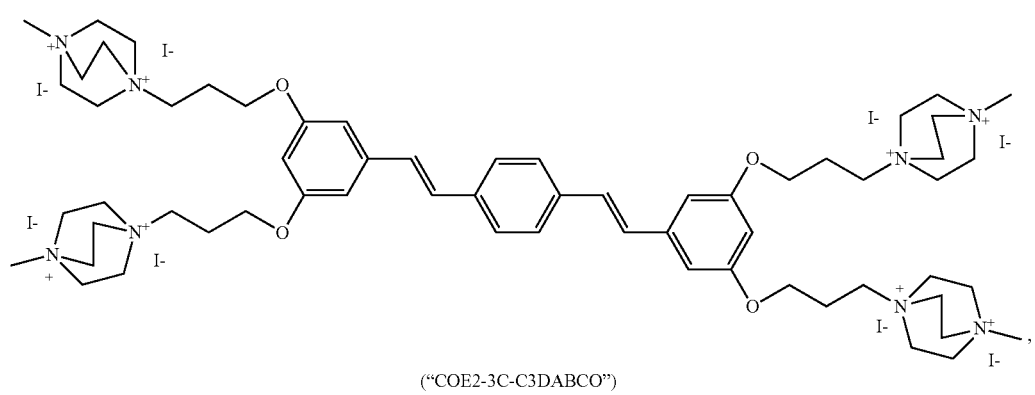
("COE2-3C-C3DABCO")
Formula GG
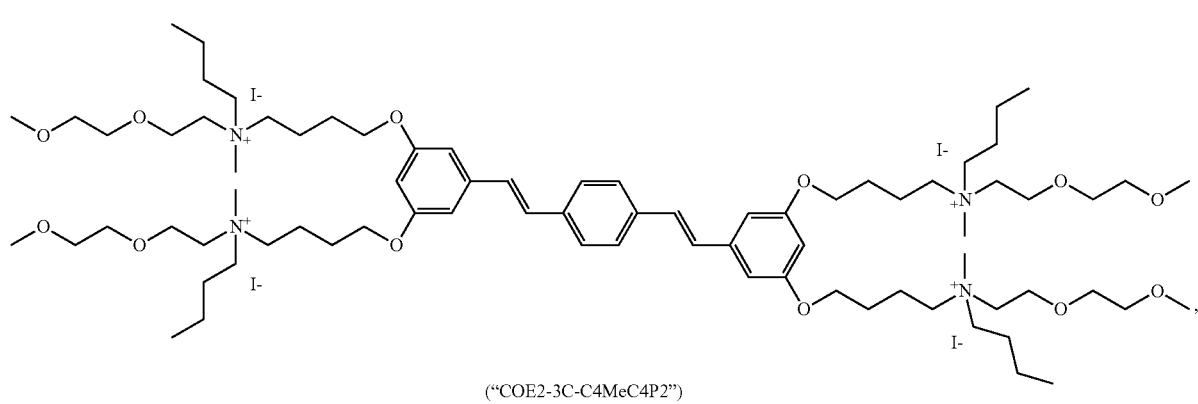
("COE2-3C-C4MeC4P2")
Formula HH
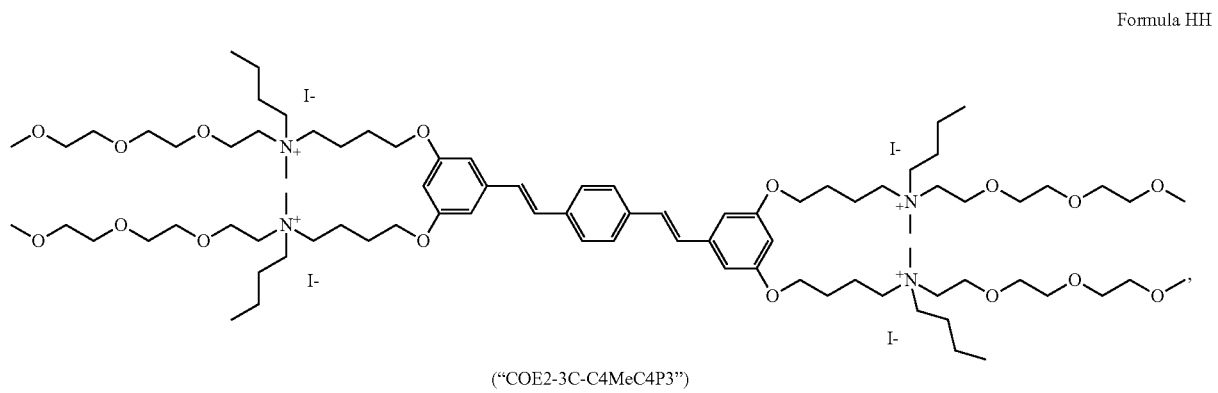
("COE2-3C-C4MeC4P3")
Formula II
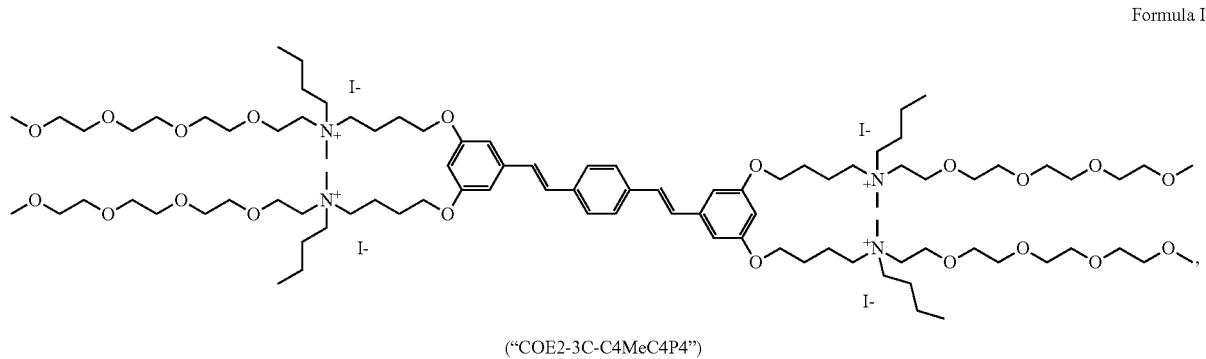
("COE2-3C-C4MeC4P4")

Formula JJ
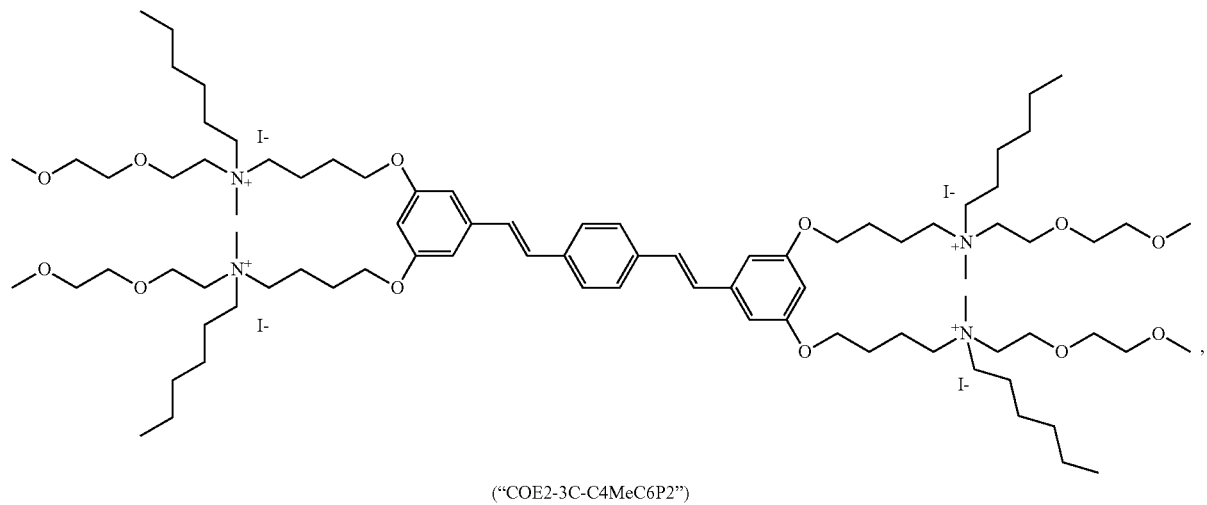
("COE2-3C-C4MeC6P2")
Formula KK
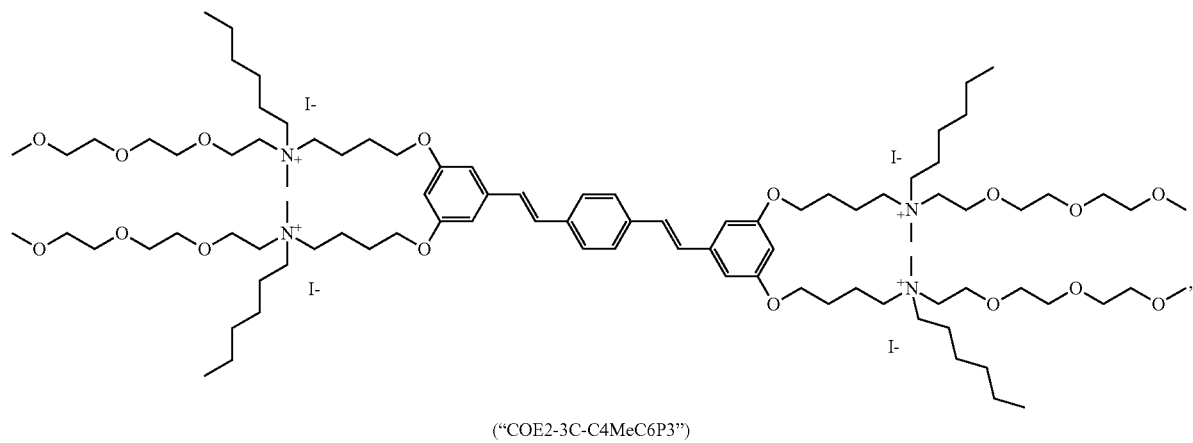
("COE2-3C-C4MeC6P3")
Formula LL
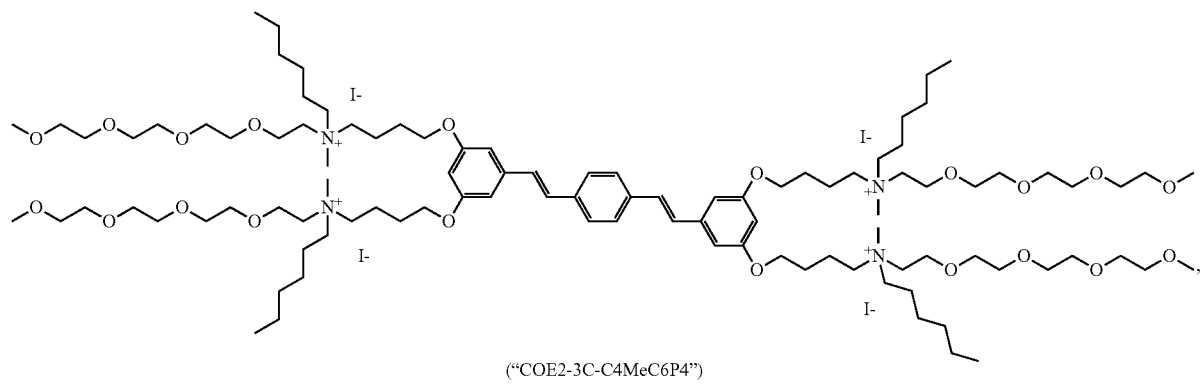
("COE2-3C-C4MeC6P4")

-continued
Formula MM
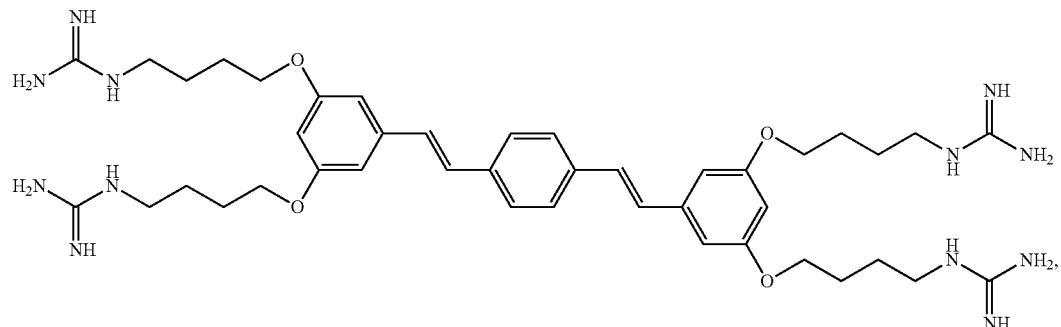
("COE 2-3C-C4guanidine")
Formula NN
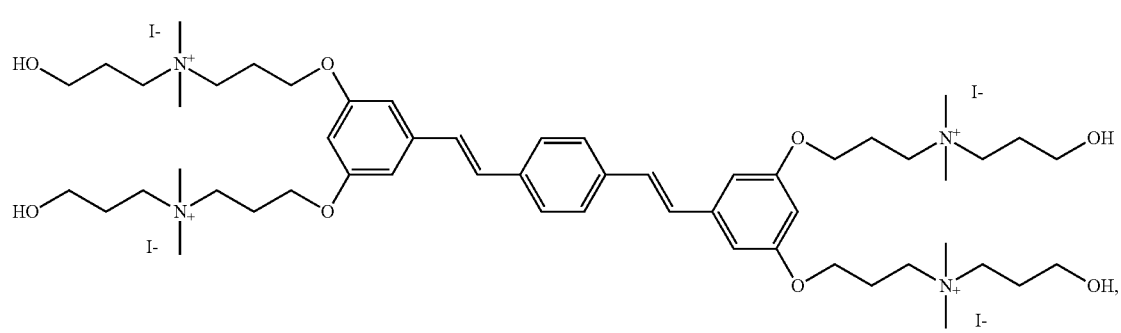
("COE2-3C-C3propyl-OH")
Formula OO
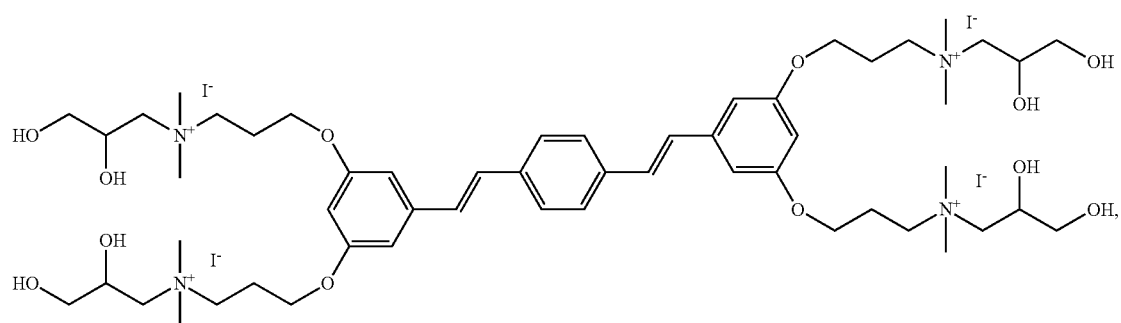
("COE2-3C-C3glycerol")
Formula PP
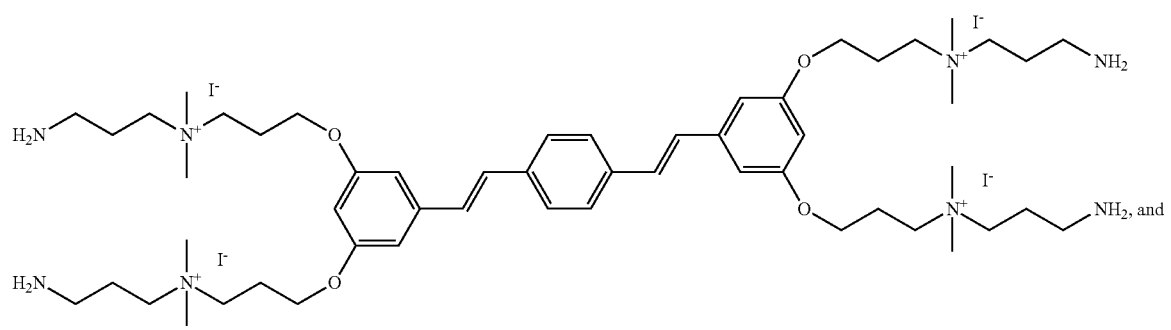
("COE2-3C-C3propyl-NH2")

Formula SS

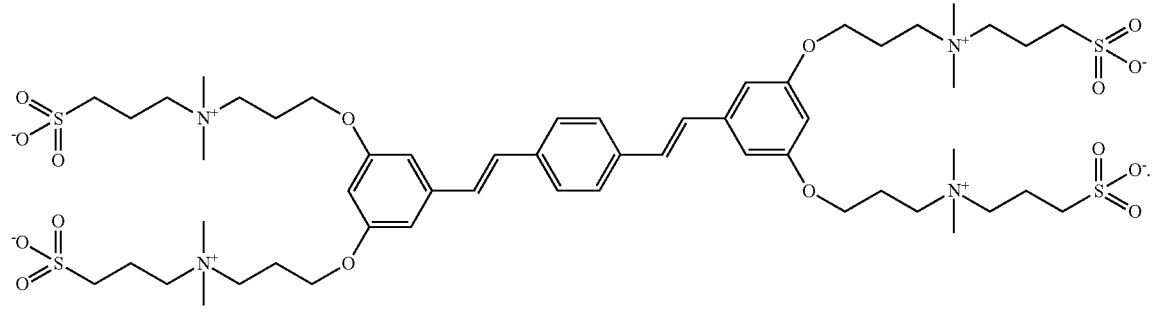

("COE2-3C-C3propyl-SO3")

4. The COE of claim 3, having a minimum inhibition concentration (MIC) of no greater than 1 μg/mL, between 1-5 μg/mL, or between 5-15 μg/mL against one or more bacteria selected from the group consisting of ST ATCC 14028, EC ATCC 25922, PA ATCC 10145, KPN ATCC13883, MRSA USA300, MSSA Newman, MRSA MT3302, MRSA MT3315, and MSSA MT3305 as determined according to Clinical and Laboratory Standards Institute (CLSI) guidelines by broth dilution.

5. A pharmaceutical composition comprising an effective amount of the COE of claim 1; and a pharmaceutically acceptable excipient.

6. A method of treating, reducing the severity of and/or slowing the progression of a bacterial infection in a mammalian subject comprising administering an effective amount of a conjugated oligoelectrolyte (COE) of claim 1.

7. The method of claim 6, wherein the bacterial infection is due to a bacteria selected from the group consisting of *Salmonella enterica Typhimurium, E. coli, Pseudomonas aeruginosa, Klebsiella pneumoniae*, methicillin-resistant *S. aureus*, methicillin-sensitive *S. aureus, E. faecium, A. baumannil, E. cloacae, S. epidermidis, K. aerogenes, S. flexneri, E pseudotuberculosis, N. gonorrhoeae*, and *S. pneumoniae.*

* * * * *